US008795664B2

(12) United States Patent
Bayer et al.

(10) Patent No.: US 8,795,664 B2
(45) Date of Patent: Aug. 5, 2014

(54) MONOCLONAL ANTIBODIES TARGETING AMYLOID BETA OLIGOMERS

(75) Inventors: Thomas Bayer, Göttingen (DE); Oliver Wirths, Friedland (DE); Henrik Martens, Kassel (DE); Christian Erck, Vordorf (DE)

(73) Assignees: Georg-August-Universität Göttingen Stiftung Öffentlichen Rechts, Universitätsmedizin, Göttingen (DE); Synaptic Systems Gesellschaft für Neurobiologische Forschung, Entwicklung und Produktion mbH, Göttingen (DE)

( * ) Notice: Subject to any disclaimer, the term of this patent is extended or adjusted under 35 U.S.C. 154(b) by 0 days.

(21) Appl. No.: 13/701,758

(22) PCT Filed: Jun. 3, 2011

(86) PCT No.: PCT/EP2011/002739
§ 371 (c)(1),
(2), (4) Date: Feb. 21, 2013

(87) PCT Pub. No.: WO2011/151076
PCT Pub. Date: Dec. 8, 2011

(65) Prior Publication Data
US 2013/0295095 A1 Nov. 7, 2013

Related U.S. Application Data

(60) Provisional application No. 61/382,640, filed on Sep. 14, 2010, provisional application No. 61/354,539, filed on Jun. 14, 2010.

(30) Foreign Application Priority Data

Jun. 4, 2010 (EP) .................................... 10165026

(51) Int. Cl.
*A61K 39/395* (2006.01)
*C07K 16/18* (2006.01)
*C12N 5/20* (2006.01)

(52) U.S. Cl.
USPC .................. 424/141.1; 424/139.1; 424/133.1; 424/135.1; 424/136.1; 530/387.9; 530/387.3; 530/388.25; 435/331

(58) Field of Classification Search
None
See application file for complete search history.

(56) References Cited

U.S. PATENT DOCUMENTS

| | | |
|---|---|---|
| 4,711,955 A | 12/1987 | Ward et al. |
| 4,816,567 A | 3/1989 | Cabilly et al. |
| 5,525,711 A | 6/1996 | Hawkins et al. |
| 5,792,608 A | 8/1998 | Swaminathan et al. |
| 2009/0258009 A1 | 10/2009 | Gellerfors et al. |
| 2010/0021478 A1 | 1/2010 | Demuth et al. |
| 2010/0028357 A1* | 2/2010 | Matsubara et al. ......... 424/139.1 |
| 2012/0082667 A1* | 4/2012 | Yokoseki et al. .......... 424/133.1 |

FOREIGN PATENT DOCUMENTS

| | | |
|---|---|---|
| EP | 302175 A2 | 2/1989 |
| EP | 1994937 A2 | 11/2008 |
| WO | 2006014478 A1 | 2/2006 |
| WO | 2009149486 A2 | 12/2009 |

OTHER PUBLICATIONS

Paul WE, editor. Fundamental Immunology, Third Edition. Raven Press, New York, 1993, pp. 292-295.*
Rudikoff S et al. (1982) Single amino acid substitution altering antigen-binding specificity. Proc. Natl. Acad. Sci. USA, 79:1979-1983.*
Goldsby et al. Immunology. Fifth Edition. New York: W.H. Freeman, 2003.
Ormerod, Michael G. Flow Cytometry; A Practical Approach. 2nd Edition. New York: IRL Press at Oxford University Press, 1994.
Rose et al. Methods in Yeast Genetics: A Laboratory Course Manual. Cold Spring Harbor, NY: Cold Spring Harbor Laboratory Press. 1990.
Sambrook et al. Molecular Cloning: A Laboratory Manual. 3rd Edition. Cold Spring Harbor, NY: Cold Spring Harbor Laboratory Press, 2001.
Spector et al. Cells: A Laboratory Manual. Plainview, NY: Cold Spring Harbor Laboratory Press, 1998.
Schilling et al. "Glutaminyl Cyclase Inhibition Attenuates Pyroglutamate Aβ and Alzheimer's Disease-Like Pathology". Nature Medicine, vol. 14, No. 10. Oct. 2008.

(Continued)

*Primary Examiner* — Kimberly A Ballard
(74) *Attorney, Agent, or Firm* — Lando & Anastasi, LLP

(57) ABSTRACT

The invention relates to binding molecules capable of specifically recognizing soluble oligomers of N-terminal truncated Aβ starting with pyroglutamate (AβpE), pharmaceutical compositions comprising same, and their respective therapeutic uses. Particularly, the invention relates to an antibody molecule capable of specifically recognizing Aβ oligomers, wherein said antibody binds and/or detects an epitope as bound and/or detected by antibody PG3-38 9D5H6 as deposited under DSM AC-C3056. Further, the invention provides a method of inhibiting the formation or the seeding effect of said AβpE oligomers, and a method for identifying agents useful in the treatment and/or prevention of an amyloid-related disorder as well as methods of diagnosing a subject suspected of suffering from a disease associated with amyloidogenesis and/or amyloid plaque formation and to methods of monitoring the efficacy of a treatment of a disease associated with amyloidogenesis and/or amyloid-plaque formation characterized by the presence of Aβ oligomers in a subject.

39 Claims, 16 Drawing Sheets

(56) References Cited

OTHER PUBLICATIONS

Schlenzig et al. "Pyroglutamate Formation Influences Solubility and Amyloidogenicity of Amyloid Peptides". Biochemistry, vol. 48, pp. 7072-7078. 2009.

Schägger et al. "Blue Native Electrophoresis for Isolation of Membrane Protein Complexes in Enzymatically Active Form". Analytical Biochemistry, vol. 199, pp. 223-231. 1991.

Selkoe et al. "Alzheimer's Disease: Genes, Proteins, and Therapy". Physiological Reviews, vol. 81, No. 2. Apr. 2001.

Sung et al. "Short Homopeptide Leader Sequences Enhanced Production of Human Proinsulin in *Escherichia coli*". Methods in Enzymology, vol. 153. 1987.

Takahashi et al. "Oligomerization of Alzheimer's β-Amyloid within Processes and Synapses of Cultured Neurons and Brain". The Journal of Neuroscience vol. 24, No. 14, pp. 3592-3599. Apr. 7, 2004.

Tanaka et al. "Eastern Blotting and Immunoaffinity Concentration Using Monoclonal Antibody for Ginseng Saponins in the Field of Traditional Chinese Medicines". Journal of Agricultural and Food Chemistry. vol. 55, pp. 3783-3787. 2007.

Tomiyama et al. "A Mouse Model of Amyloid β Oligomers: Their Contribution to Synaptic Alteration, Abnormal Tau Phosphorylation, Glial Activation, and Neuronal Loss In Vivo". The Journal of Neuroscience. vol. 30, No. 14, pp. 4845-4856. Apr. 7, 2010.

Towbin et al. "Electrophoretic Transfer of Proteins from Polyacrylamide Gels to Nitrocellulose Sheets: Procedure and Some Applications". Proc. Natl. Acad. Sci. vol. 76, No. 9, pp. 4350-4354. Sep. 1979.

Walsh et al. "Naturally Secreted Oligomers Amyloid β Protein Potently Inhibit Hippocampal Long-Term Potentiation in Vivo". Letters to Nature, vol. 416. Apr. 2002.

Walsh et al. "The Oligomerization of Amyloid β-Protein Begins Intracellularly in Cells Derived from Human Brain". Biochemistry, vol. 39, pp. 10831-10839. 2000.

Wirths et al. "Age-Dependent Axonal Degeneration in an Alzheimer Mouse Model". Neurobiology of Aging, vol. 28, pp. 1689-1699. 2007.

Wirths et al. "Deficits in Working Memory and Motor Performance in the APP/PS1ki Mouse Model for Alzheimer's Diease". Neurobiology of Aging, vol. 29, pp. 891-901. 2008.

Wirths et al. "Identification of Low Molecular Weight Pyroglutamate Aβ Oligomers in Alzheimer Diease—A Novel Tool for Therapy and Diagnosis". The Journal of Biological Chemistry. vol. 285, No. 53, pp. 41517-41524. Dec. 31, 2010.

Wirths et al. "Intraneuronal Pyroglutamate-Abeta 3-42 Triggers Neurodegeneration and Lethal Neurological Deficits in a Transgenic Mouse Model". Acta Neuropathol. vol. 118, pp. 487-496. 2009.

Wirths et al. "Pyroglutamate Abeta Pathology in APP/PS1KI Mice, Sporadic and Familial Alzheimer's Disease Cases". J. Neural. Transm. vol. 117, pp. 85-96. 2010.

Acero et al. "Immunodominant Epitope and Properties of Pyroglutamate-Modified Aβ-Specific Antibodies Produced in Rabbits". Journal of Neuroimmunology. vol. 213, pp. 39-46. Aug. 18, 2009.

Aoki et al. "Amyloid β-Peptide Levels in Laser Capture Microdissected Cornu Ammonis I Pyramidal Neurons of Alzheimer's Brain". NeuroReport. No. 19, vol. 11, pp. 1085-1089. Jul. 16, 2008.

Billings et al. "ELKS1 and Ca2+ Channel Subunit β4 Interact and Colocalize at Cerebellar Synapses". NeuroReport. vol. 23, No. 1, pp. 49-54. 2012.

Billman-Jacobe et al. "Expression in Bacteria other than *Escherichia coli*". Current Opinion in Biotechnology. No. 7, pp. 500-504. 1996.

Bitter et al. "Expression and Secretion of Vectors for Yeast". Methods in Enzymology. vol. 153, pp. 516-544. 1987.

Boche et al. "Neuropathology After Active Aβ42 Immunotherapy: Implications for Alzheimer's Disease Pathogenesis". Acta Neuropathol. vol. 120, pp. 369-384. 2010.

Bosman et al. "Some Recent Developments in Immunocytochemistry". Histochemical Journal. vol. 15, pp. 189-200. 1983.

Breyhan et al. "APP/PS1KI Bigenic Mice Develop Early Synaptic Deficits and Hippocampus Atrophy". Acta Neuropathol. vol. 117, pp. 677-685. Apr. 2009.

Burnette et al. "Western Blotting: Electrophoretic Transfer of Proteins from Sodium Dodecyl Sulfate—Polyacrylamide Gels to Unmodified Nitrocellulose and Radiographic Detection with Antibody and Radioiodinated Protien A". Analytical Biochemistry. vol. 112, pp. 195-203. 1981.

Busciglio et al. "Altered Metabolism of the Amyloid β Precursor Protein is Associated with Mitochondrial Dysfunction in Down's Syndrome". Neuron. vol. 33, pp. 677-688. Feb. 28, 2002.

Butler et al. "The Immunochemistry of Sandwich ELISAs—I. The Binding Characteristics of Immunoglobulins to Monoclonal and Polyclonal Capture Antibodies Absorbed on Plastic and Their Detection by Symmetrical and Asymmetrical Antibody-Enzyme Conjugates". Molecular Immunology. vol. 23, No. 9, pp. 971-982. 1986.

Casas et al. Massive CA1/2 Neuronal Loss with Intraneuronal and N-Terminal Truncated Aβ42 Accumulation in a Novel Alzheimer Transgenic Model. American Journal of Pathology. vol. 165, No. 4. Oct. 2004.

Chauhan et al. "Effect of Age on the Duration and Extent of Amyloid Plaque Reduction and Microglial Activation After Injection of Anti-Aβ Antibody into the Third Ventricle of TgCRND8 Mice". Journal of Neuroscience Research, vol. 78. pp. 732-741. Dec. 1, 2004.

Christensen et al. "Intracellular Aβ Triggers Neuron Loss in the Cholinergic System of the APP/PS1KI Mouse Model of Alzheimers Disease". Neurobiology of Aging. vol. 31, pp. 1153-1163. 2010.

Christensen et al. "Transient Intraneuronal Aβ rather than Extracellular Plaque Pathology Correlates with Neuron Loss in the Frontal Cortex of APP/PS1KI Mice". Acta Neuropathol. vol. 116, pp. 647-655. Oct. 2008.

Coloma et al. "Novel Vectors for the Expression of Antibody Molecules Using Variable Regions Generated by Polymerase Chain Reaction". Journal of Immunological Methods. vol. 152, pp. 89-104. 1992.

D'Andrea et al. Evidence That Neurones Accumulating Amyloid Can Undergo Lysis to Form Amyloid Plaques in Alzheimer's Disease. Histopathology. vol. 38, pp. 120-134. 2001.

D'Andrea et al. "Lipofuscin and Aβ42 Exhibit Distinct Distribution Patterns in Normal and Alzheimer's Disease Brains". Neuroscience Letters. vol. 323, pp. 45-49. 2002.

Engvall et al. "Enzyme-Linked Immunosorbent Assay (ELISA) Quantitative Assay of Immunoglobulin G". Immunochemistry. vol. 8, pp. 871-874. 1971.

Fernandez-Vizarra et al. "Intra- and Extracellular Aβ and PHF in Clinically Evaluated Cases of Alzheimer's Disease". Histology and Histopathology, Cellular and Molecular Biology. vol. 19, pp. 823-844. 2004.

Gersten et al. "A Rapid, Novel Method for the Solid-Phase Derivatization of IgG Antibodies for Immune-Affinity Chromatography". Journal of Immunological Methods. vol. 24, pp. 305-309. 1978.

Griffiths et al. "Production of Heterologous Proteins Using the Baculovirus/Insect Expression System". Methods in Molecular Biology. vol. 75, pp. 427-440. 1997.

Gurtu et al. "IRES Bicistronic Expression Vectors for Efficient Creation of Stable Mammalian Cell Lines". Biochemical and Biophysical Research Communications, vol. 229, pp. 295-298. 1996.

Gyure et al. "Intraneuronal Aβ-Amyloid Precedes Development of Amyloid Plaques in Down Syndrome". Arch Pathol Lab Med. vol. 25, pp. 489-492. Apr. 2001.

Harmeier et al. "Role of Amyloid-β Glycine 33 in Oligomerization, Toxicity and Neuronal Plasticity". The Journal of Neuroscience, vol. 29, No. 23, pp. 7582-7590. Jun. 10, 2009.

Hashimoto et al. "Analysis of Microdissected Human Neurons by a Sensitive ELISA Reveals a Correlation Between Elevated Intracellular Concentrations of Aβ42 and Alzheimer's Disease Neuropathology". Acta Neuropathol, vol. 119, pp. 543-554. Mar. 2010.

He et al. "The Aβ 3-Pyroglutamyl and 11-Pyroglutamyl Peptides Found in Senile Plaque Have Greater β-Sheet Forming and Aggregation Propensities in Vitro than Full-Length Aβ". Biochemistry, vol. 38, No. 33, pp. 10871-10877. Aug. 1999.

(56) References Cited

OTHER PUBLICATIONS

Hockney et al. "Recent Developments in Heterologous Protein Production in *Escherichia coli*". Trends in Biotechnology, vol. 12. Nov. 1994.

Holcomb et al. "Behavioral Changes in Transgenic Mice Expressing Both Amyloid Precursor Protein and Presenilin-1 Mutations: Lack of Association with Amyloid Deposits". Behavior Genetics, vol. 29, No. 3, pp. 177-185. 1999.

Jawhar et al. "Motor Deficits, Neuron Loss, and Reduced Anxiety Coinciding with Axonal Degeneration and Intraneuronal Aβ Aggregation in the 5XFAD Mouse Model of Alzheimer's Disease". Neurobiology of Aging, vol. 33. 2010.

Karl et al. "Behavioral Phenotyping of Mice in Pharmacological and Toxicological Research". Exp Toxic Pathol, vol. 55, pp. 69-83. 2003.

Kessler, Steven W. Rapid Isolation of Antigens from Cells with a Staphylococcal Protein A-Antibody Adsorbent: Parameters of the Interaction of Antibody-Antigen Complexes with Protein A. The Journal of Immunology. vol. 115, No. 6. Dec. 1975.

Klein et al. "Aβ Toxicity in Alzheimer's Disease: Globular Oligomers (ADDLs) as New Vaccine and Drug Targets". Neurochemistry International, vol. 41, pp. 345-352. 2002.

Kohler et al. "Continuous Cultures of Fused Cells Secreting Antibody of Predefined Specificity". Nature, vol. 256. Aug. 7, 1975.

Lambert et al. "Diffusible, Nonfibrillar Ligands Derived from A 1-42 are Potent Central Nervous System Neurotoxins". Proc. Natl. Acad. Sci. vol. 95, pp. 6448-6453. May 1998.

Lesné et al. "A Specific Amyloid-β Protein Assembly in the Brain Impairs Memory". Letters to Nature, vol. 440. Mar. 16, 2006.

Lord et al. "Amyloid-β Protofibril Levels Correlate with Spatial Learning in Arctic Alzheimer's Disease Transgenic Mice". FEBS Journal, vol. 276, pp. 995-1006. 2009.

Lord et al. "The Arctic Mutation Facilitates Early Intraneuronal Aβ Aggregation and Senile Plaque Formation in Transgenic Mice". Neurobiology of Aging, vol. 27, p. 67-77. 2006.

Matutes et al. "The Fine Structure of Normal Lymphocyte Subpopulations—A Study with Monclonal Antibodies and the Immunogold Technique". Clin. Exp. Immunol. vol. 50, pp. 416-425. 1982.

McLean et al. "Soluble Pool of Aβ Amyloid as a Determinant of Severity of Neurodegeneration in Alzheimer's Disease". Annals of Neurology, vol. 46, No. 6. Dec. 1999.

Mochizuki et al. "Aβ 42-Positive Non-Pyramidal Neurons Around Amyloid Plaques in Alzheimer's Disease". The Lancet. vol. 355. Jan. 1, 2000.

Mori et al. "Intraneuronal Aβ42 Accumulation in Down Syndrome Brain". Amyloid: J. Protein Folding Disord. vol. 9, pp. 88-102. 2002.

Mori et al. "Mass Spectrometry of Purified Amyloid β Protein in Alzheimer's Disease". The Journal of Biological Chemistry. vol. 267, No. 24, pp. 17082-17086. Aug. 25, 1992.

Nebe-Von-Caron et al. "Analysis of Bacterial Function by Multi-Colour Fluorescence Flow Cytometry and Single Cell Sorting". Journal of Microbiological Methods, vol. 42, pp. 97-114. 2000.

Näslund et al. "Correlation Between Elevated Levels of Amyloid β-Peptide in the Brain and Cognitive Decline". JAMA, vol. 283, No. 12. Mar. 2000.

Ono et al. "Structure-Neurotoxicity Relationships of Amyloid β-Protein Oligomers". PNAS. vol. 106, No. 35, pp. 14745-14750. Sep. 1, 2009.

Renart et al. "Transfer of Proteins from Gels to Diazobenzyloxymethyl-Paper and Detection with Antisera: A Method for Studying Antibody Specificity and Antigen Structure". Proc. Natl. Acad. Sci. vol. 76, No. 7, pp. 3116-3120. Jul. 1979.

Rohrer et al. "Genetically Modified PC12 Brain Grafts: Survivability and Inducible Nerve Growth Factor Expression". Cell Transplantation. vol. 5, No. 1, pp. 57-68. 1996.

Saido et al. "Dominant and Differential Deposition of Distinct β-Amyloid Peptide Species, Aβn3(pE), in Senile Plaques". Neuron, vol. 14, pp. 457-466. Feb. 1995.

Sawers et al. "Alternative Regulation Principles for the Production of Recombinant Proteins in *E Scherichia coli*". Appl Microbiol Biotechnol. vol. 46, pp. 1-9. 1996.

Castillo, Michelle. "Poor Results Halt Production, Studies on Promising Alzheimer's Drug Bapineuzumab". CBS Interactive Inc. Retrieved from the Internet www.cbsnews.com/8301-504763162-57488206-10391704/poor-results-halt-production-studies-onpromising-alzheimers-drug-bapineuzumab/> Retrieved Aug. 7, 2012.

Johnson & Johnson. "Johnson & Johnson Announces Discontinuation of Phase 3 Development of Bapineuzumab Intravenous (IV) in Mild-to-Moderate Alzheimer's Disease". Retrieved from the Internet www.jnj.com/news/product/johnson-and-johnson-announces-discontinuation-of-phase-3-development-ofbapineuzumab-intravenous-iv-in-mild-to-moderate-alzheimers-disease> Retrieved on Apr. 9, 2013.

Kambhampaty, Anusha. "Roche's Gantenerumab Could Face Silimar Fate as Failed Drug Bapineuzumab in Alzheimer's, Experts Say". The Financial Times LTD. Retrieved from the Internet www.ft.com/cms/s/2/2a16570a-e585-11e2-ad1a-00144feabdcO.html#axzz2gZ86EQ9p> Retrieved Sep. 26, 2013.

Miles et al. "Bapineuzumab Captures the N-Terminus of the Alzheimer's Disease Amyloid-Beta Peptide in a Helical Conformation". Scientific Reports, 3:1302. Feb. 18, 2013.

Sussex Drug Discovery. "Bexarotene in Alzheimer's Disease: A Case of Lack of Replication, Lack of Replication, Lack of Replication". Retrieved from the Internet sussexdrugdiscovery.wordpress.com/tag/bapineuzumab/> Retreived Sep. 27, 2013.

\* cited by examiner

MONOCLONAL ANTIBODIES TARGETING AMYLOID BETA OLIGOMERS

The present invention relates to binding molecules capable of specifically recognizing soluble oligomers of N-terminal truncated Aβ starting with pyroglutamate (AβpE), pharmaceutical compositions comprising same, and their respective therapeutic uses. Particularly, the present invention relates to an antibody molecule capable of specifically recognizing Aβ oligomers, wherein said antibody binds and/or detects an epitope as bound and/or detected by antibody PG3-38 9D5H6 as deposited under DSM ACC3056. Further, the invention provides a method of inhibiting the formation or the seeding effect of said AβpE oligomers, and a method for identifying agents useful in the treatment and/or prevention of an amyloid-related disorder as well as methods of diagnosing a subject suspected of suffering from a disease associated with amyloidogenesis and/or amyloid plaque formation and to methods of monitoring the efficacy of a treatment of a disease associated with amyloidogenesis and/or amyloid-plaque formation characterized by the presence of Aβ oligomers in a subject.

BACKGROUND OF THE INVENTION

Alzheimer disease (AD) is a progressive neurodegenerative disorder characterized by the presence of extracellular amyloid plaques composed of amyloid-β (Aβ) surrounded by dystrophic neurites and neurofibrillary tangles. The discovery that certain early-onset familial forms of AD may be caused by an enhanced production of Aβ peptides have led to the hypothesis that amyloidogenic Aβ is intimately involved in the AD pathogenic process. Besides Aβ peptides starting with an aspartate at position 1, a variety of different N-truncated Aβ peptides have been identified in AD brains. Ragged peptides with a major species including those beginning with phenylalanine at position 4 of Aβ have been reported. In contrast, no N-terminal sequence could be obtained from cores purified in a sodium dodecyl sulfate-containing buffer, which led to the assumption that the N-terminus could be blocked. The presence of AβpE (N-terminal truncated Aβ starting with pyroglutamate) in AD brain was subsequently shown using mass spectrometry of purified Aβ peptides, explaining at least partially initial difficulties in sequencing Aβ peptides purified from human brain tissue (Mori (1992) J Biol Chem 267: 17082-17086). It was reported that only 10-15% of the total Aβ isolated by this method begins at position 3 with AβpE3. It was also shown that AβpE3 represents a dominant fraction of Aβ peptides in senile plaques of AD brains (Saido (1995) Neuron 14: 457-466). This was later confirmed by other reports investigating AD and Down's syndrome post-mortem brain tissue.

In general, N-terminal deletions enhance aggregation of β-amyloid peptides in vitro. Importantly, AβpE3 has a higher aggregation propensity (He (1999) Biochem 38: 10871-10877). Under in vivo conditions, truncated Aβ oligomers appeared to be generated by hydrolysis at multiple sites rather than by post-mortem N-terminal degradation. Recently, it has been demonstrated that the N-terminal pE-formation can be catalyzed by glutaminyl cyclase (QC) which pharmacologically is interfered by a QC inhibitor, both in vitro. QC expression was found up-regulated in the cortex of patients with AD and correlated with the appearance of pE-modified Aβ. Oral application of a glutaminyl cyclase inhibitor resulted in reduced AβpE3-42 burden in two different transgenic mouse models of AD and in a new *Drosophila* model. Interestingly, treatment of these mice was accompanied by reductions in Aβx-40/42, diminished plaque formation and gliosis, as well as improved performance in context memory and spatial learning tests (Schilling (2008), Nat. Med 14:1106-1111). However, such a therapeutic approach has the disadvantage that it may also interfere with the non-pathologic function of QC, as it is also expressed in other tissues.

A promising experimental approach to unravel the role of Aβ in AD pathology has been the generation of transgenic mice overexpressing the amyloid precursor protein (APP). They mimic the typical AD-like pathological deficits in synaptic transmission, changes in behavior, differential glutamate responses and deficits in long-term potentiation. These characteristics are generally attributed to the overexpression of full-length amyloid precursor protein (APP). Although learning deficits were evident in various APP models, the extent of β-amyloid deposition did not correlate with the behavioral phenotype (Holcomb (1999) Behav Genet 29: 177-185). Previously, it has been reported that intraneuronal Aβ rather than extracellular plaque pathology correlates with neuron loss in the hippocampus (Casas (2004) Am J Pathol 165: 1289-1300), the frontal cortex (Christensen (2008) Acta Neuropathol 116: 647-655) and the cholinergic system (Christensen (2008) Neurobiol Aging 31: 1153-1163) of APP/PS1KI mice expressing transgenic human mutant APP751 including the Swedish and London mutations on a murine knock-in (KI) Presenilin 1 (PS1) background with two FAD-linked mutations (PS1 M233T and PS1 L235P). The APP/PS1KI mice exhibit robust learning deficits at the age of 6 months (Wirths (2008) Neurbiol Aging 29: 891-901), age-dependent axonopathy (Wirths (2007) Neurobiol Aging 28: 1689-1699), neuron loss in hippocampus CA1 together with synaptic deficits, and hippocampus atrophy coinciding with intraneuronal aggregation of N-terminal modified Aβ variants (Breyhan (2009) Acta Neuropathol 117: 677-685). Notably, the APP/PS1 KI mouse model exhibits a large heterogeneity of N-truncated Aβx-42 variants accumulating in an age-dependent manner (Casas (2004), Am. J. Pathol. 165: 1289-1300). A mouse model expressing only N-truncated AβpE3-42 in neurons has been generated and it was shown that this peptide is neurotoxic in vivo inducing neuron loss and an associated neurological phenotype (Wirths (2009) Acta Neuropathol 118: 487-496).

In the past, extracellular Aβ has been regarded as the causative agent, whereas more recent evidence also relates toxic effects of Aβ to events in intracellular compartments. In addition, another concept proposing that the soluble oligomers and the β-sheet containing amyloid fibrils are the toxic forms of Aβ (Selkoe (2001) Physiol Rev 81: 741-766; Klein (2002) Neurochem Int 41: 345-352; Harmeier (2009) J Neurosci 29: 7582-7590).

In this context, US 2009/0258009 A1 describes a high affinity antibody selective for amyloid beta protein (non-modified protein) in its protofibril conformation.

It has further been demonstrated that soluble oligomeric Aβ42, but not plaque-associated Aβ, correlates best with cognitive dysfunction in AD. Oligomers are formed preferentially intracellularly within neuronal processes and synapses rather than extracellularyl. In this context, it was also reported that the disintegration of Aβ plaques may give rise to pathological side effects (Boche et al., Acta Neuropathol 120: 369-384 (2010)). Therefore, plaques may represent safe deposition sites of Aβ-peptides, which should not be disintegrated again.

However, it is still hardly possible to distinguish individuals not actually suffering from amyloid or Aβ-related dementia from patients suffering from such a disorder, e.g. from Alzheimer disease. Moreover, there is still a need for medicaments for use in the treatment of patients suffering from amyloid or Aβ-related dementia, e.g. from Alzheimer Disease.

SUMMARY OF THE INVENTION

This technical problem has been solved by the embodiments provided herein and the solutions provided in the claims.

The present invention relates to an antibody molecule capable of specifically recognizing Aβ oligomers. It can be shown in context of the invention that oligomeric Aβ versions, in particular oligomeric AβpE3 peptides, can be employed to neuropathologically differentiate healthy controls from patients with sporadic or familial Alzheimer Disease (AD). Accordingly, the present invention provides for means and methods as well as for specific tools, which are capable in differentiating individuals not suffering from an amyloid-related dementia and even healthy controls from patients suffering from Alzheimer Disease. Most importantly, it could be shown herein that such a diagnostic distinction can be successfully carried out on biological samples derived from living individuals.

In context of this invention it was also found that N-terminal truncated Aβ starting with pyroglutamate (AβpE3) can form stable oligomers. Such oligomers are even stable in detergents, in particular in SDS, as shown in the appended examples. In context of this invention, new diagnostic and pharmaceutically useful tools have been generated whereby these tools relate to binding molecules, in particular antibody molecules that are binding to oligomeric forms of Aβ, in particular to oligomeric AβpE3.

Furthermore, antibodies of the present invention are directed against oligomeric forms of Aβ, in particular of AβpE3-42 and show prominent intraneuronal and blood vessel staining in sporadic and familial AD cases. Plaque staining with these antibodies was demonstrated mostly in familial cases with aggressive pathology. Importantly, non-demented control specimen showed no staining with the antibodies of this invention at all, even in cases with abundant plaque load. This makes the antibodies/binding molecules of the invention important novel tools in the diagnosis of dementia and/or amyloid related disorders. In context of this invention, antibodies/binding molecules are provided that are recognizing Aβ oligomers, e.g., oligomeric AβpE3-42. These antibodies can be employed in one embodiment as (a) diagnostic tool(s). The surprising technical contribution to the art is that these antibodies/binding molecules of the invention can also be used in the deduction/evaluation of either pathological samples or of samples derived from non-demented control specimens. The antibodies of this invention are useful, inter alia, in the diagnosis of amyloid-related disorders, like Alzheimer Disease (AD), in in vitro samples, like tissue samples such as brain samples or fluid biological samples derived from subjects in need of such a diagnosis.

Exemplified antibody molecules are antibodies that can be obtained from hybridomas as deposited under DSM ACC3056 (PG3-38 9D5H6, or "9D5H6" or "9D5" herein) or antibodies obtained from hybridomas as deposited at DSMZ on May 27, 2010 under DSM ACC3066 (PG3-38 8C4D2, or "8C4D2" or "8C4" herein). Accordingly, the present invention also relates to a binding molecule or an antibody molecule capable of specifically recognizing Aβ oligomers, wherein said antibody binds and/or detects an epitope as bound and/or detected by antibody "9D5". An example of such a binding molecule/antibody molecule that binds and/or detects an epitope as bound and/or detected by antibody "9D5" as obtainable from a hybridoma as deposited under DSM ACC3056 is antibody "8C4", obtainable from a hybridoma as deposited at DSMZ on May 27, 2010 under DSM ACC3066 (PG3-38 8C4D2) and deposited in the name of Synaptic Systems GmbH and the Georg-August-Universität Göttingen, Stiftung Öffentlichen Rechtes, Universitätsmedizin. In the present work, the inventors studied the potential involvement of oligomeric AβpE3 in vivo using transgenic mouse models as well as human brains from sporadic and familial AD cases. The inventors generated a novel monoclonal antibody (9D5) that selectively recognizes oligomeric assemblies of AβpE3 inhibiting further aggregation. 9D5 also demonstrated abundant intracellular immunostaining in both mouse and human brains of sporadic as well as familial AD cases.

The present invention also relates to a method of diagnosing a subject/patient suspected of suffering from a disease associated with amyloidogenesis and/or amyloid-plaque formation, comprising the steps of (a) determining in a cell or tissue sample obtained from said subject/patient the amount of Aβ oligomers; and (b) comparing the amount of Aβ oligomers determined in a) with a reference amount of Aβ oligomers determined in (a sample from) a control subject/patient (healthy subject), wherein said disease is diagnosed when said amount determined in (a) differs from said reference amount. In one embodiment, these Aβ-oligomers are oligomers of N-terminal truncated Aβ starting with pyroglutamate (AβpE3).

The present invention also relates to a method of monitoring the efficacy of a treatment of a disease associated with amyloidogenesis and/or amyloid-plaque formation characterized by the presence of Aβ oligomers in a subject/patient suffering from said disease or being prone to suffering from said disease comprising the steps:

(a) determining in a biological sample obtained from said subject/patient the amount of Aβ oligomers; and (b) comparing the amount of Aβ oligomers determined in a) with a reference amount of Aβ oligomers determined in (a sample from) a control subject/patient (healthy subject), wherein the extent of the difference between said amount determined in (a) and said reference amount is indicative for said efficacy of a treatment of said disease. In one embodiment, these Aβ-oligomers are oligomers of N-terminal truncated Aβ starting with pyroglutamate (AβpE3).

The present invention also relates to a method of predicting the efficacy of a treatment of a disease associated with amyloidogenesis and/or amyloid-plaque formation for a subject/patient suffering from said disease or being prone to suffering from said disease comprising the steps:

(a) determining in biological sample obtained from said subject/patient the amount of Aβ oligomers; and (b) comparing the amount of Aβ oligomers determined in (a) with a reference amount of Aβ oligomers determined in a cell or tissue sample obtained from a control subject/patient, wherein the extent of the difference between said amount of Aβ oligomers determined in (a) and said reference amount of Aβ oligomers is indicative for the predicted efficacy of a treatment of said disease. In one embodiment, these Aβ-oligomers are oligomers of N-terminal truncated Aβ starting with pyroglutamate (AβpE3).

In addition, as demonstrated by the inventors in the examples, passive immunization of 5XFAD mice with a binding molecule which specifically recognizes N-terminal truncated AβpE3 (9D5) significantly reduced AβpE3 levels as expected, since it inhibits higher oligomerization (see FIG. 12).

Surprisingly, however, passive immunization of 5XFAD mice with 9D5 also significantly reduced the general Aβ-plaque load thereby reducing plaques with varieties of different Aβ fragments. This is even more surprising since 9D5 does not recognise Aβ fragments other than AβpE3 in its oligomeric form. Further, the inventors found that passive immunization of 5XFAD mice with 9D5 normalized behavioral deficits.

From these findings, the inventors are convinced that the key component for the pathogenesis of AD is oligomeric AβpE3, which acts as seed for plaque formation thereby blocking healthy exocytosis and degradation of Aβ and causing toxic effects leading to death of neurons.

Accordingly, the present invention is directed to therapeutic methods and substances reducing oligomeric AβpE3. This can be achieved by inhibiting the oligomerization of AβpE3 through a binding molecule, as has been demonstrated in the 5XFAD mouse model. Alternatively or additionally, this can further be achieved by degradation of already formed oligomeric AβpE3 through normal immunological processes, e.g., initiated by an antibody specific to oligomeric AβpE3 such as 9D5.

The present invention has the further advantage that, in contrast to QC inhibitors, it is highly specific. Moreover, already existing plaques are not disintegrated and it is believed that the binding molecule according to the invention does not give rise to pathologic side effects as reported for antibodies which are directed against non-modified Aβ-peptides or oligomers.

Accordingly, the present invention also relates to a binding molecule capable of specifically recognizing soluble oligomers of N-terminal truncated Aβ starting with pyroglutamate (AβpE3), and capable of inhibiting Aβ-oligomerization for use in a method of treating and/or preventing an amyloid-related disorder; comprising administering said binding molecule to a subject suffering or prone to suffer from said amyloid-related disorder.

Further, the present invention is directed to a pharmaceutical composition comprising a binding molecule as defined in the first aspect and a pharmaceutically acceptable carrier, excipient and/or diluent. Said pharmaceutical composition may be used in the treatment and/or prevention of an amyloid-related disorder in a subject suffering or prone to suffer from said amyloid-related disorder.

The present invention pertains to a method of inhibiting the formation or the seeding effect of oligomers of AβpE3 associated with an amyloid-related disorder in a subject, who has or is prone to form said oligomers, comprising administering a binding molecule capable of specifically recognizing soluble AβpE3 oligomers, and capable of inhibiting Aβ-oligomerization to said subject. Finally, the present invention is directed to a method for identifying agents useful in the treatment and/or prevention of an amyloid-related disorder, comprising the steps of
(i) incubating monomeric AβpE3 with a candidate agent and determining the rate of oligomerization and aggregation; and
(ii) incubating monomeric AβpE3, which has not been incubated with a candidate agent and determining the rate of oligomerization and aggregation;
wherein a decreased rate of aggregation determined in step (i) compared to the rate of aggregation determined in step (ii) is indicative of an agent useful in the treatment and/or prevention of an amyloid-related disorder.

DETAILED DESCRIPTION OF THE PREFERRED EMBODIMENTS

In context of the present invention, exemplarily, antibodies as provided herein ("9D5" and "8C4" as obtainable from hybridomas as deposited with DSMZ, Deutsche Sammlung von Mikroorganismen und Zellkulturen, Germany under DSM ACC3056 and DSM ACC3066, respectively, and as deposited at DSMZ on May 27, 2010) were characterized by immunohistochemistry in APP/PS1KI and 5xFAD mice, sporadic and familial AD cases and healthy controls. While plaques in certain mouse models could be stained using "9D5" or "8C4" antibody, only a fraction of "9D5" or "8C4" plaques were positive in patients with sporadic AD and familial AD including those carrying mutations in APP (arctic and Swedish) and Presenilin-1 (PS1) mutation carriers. However, abundant intraneuronal staining was seen in transgenic models, as well as in all familial Alzheimer Disease (AD) cases and some sporadic AD cases. In addition, strong immunostaining was observed in many human AD cases in blood vessels, e.g., in tissue samples. It was surprisingly found that staining with antibody molecules of the present invention was negligible in healthy control specimens although some of these healthy human controls harboured plaques. In both AD mouse models exemplified herein, intraneuronal staining with antibodies of the invention appeared during aging coinciding with the onset of learning and memory deficits. Furthermore, antibodies provided herein recognize AβpE3-42 oligomers (approximately 10 kDa), but not monomers or dimers as documented by SDS-Western blot and Dot Blot assays. Antibodies of this invention such as "9D5" or "8C4" do also not cross-react with Aβ1-42. The antibodies/binding molecules of this invention are useful in diagnostic assays, e.g., in diagnostic in vitro assays, wherein the sample material is a tissue sample or a biological liquid, like, e.g. a blood sample or a sample of cerebral fluid. For example, using a sandwich ELISA with "9D5" as capturing antibody, the levels of oligomers in plasma samples from patients with AD and healthy controls demonstrate that the mean level of oligomers is significantly decreased in AD patients ($p<0.05$). Overall, antibodies and binding molecules directed against oligomeric AβpE3 peptides and as disclosed herein are unique as they neuropathologically differentiate healthy controls from AD cases and represent therefore also diagnostic tools. Accordingly, the present invention also relates to diagnostic compositions comprising an antibody molecule capable of specifically recognizing Aβ oligomers, like AβpE3 oligomers, wherein said antibody binds and/or detects an epitope as bound and/or detected by antibody 9D5H6.

The present invention also relates to a method of diagnosing a subject/patient suspected of suffering from a disease associated with amyloidogenesis and/or amyloid-plaque formation, comprising the steps of
(a) determining in a cell or tissue sample obtained from said subject/patient the amount of Aβ oligomers; and
(b) comparing the amount of Aβ oligomers determined in a) with a reference amount of Aβ oligomers determined in (a sample from) a control subject/patient (healthy subject),
wherein said disease is diagnosed when said amount determined in (a) differs from said reference amount. In one embodiment, these Aβ-oligomers are oligomers of N-terminal truncated Aβ starting with pyroglutamate (AβpE3). Said "cell or tissue sample" may also be a biological sample, like a blood sample or a cerebral fluid sample, like liquor etc. Said "comparing step (b)" can also comprise the comparison of the amount of Aβ oligomers determined in step (a) with a reference amount of Aβ oligomers determined in a control or reference sample taken at previous time points or after successful treatment from the subject/patient in need of the corresponding diagnosis, i.e. the subject/patient that is suspected of suffering from a disease associated with amyloidogenesis and/or amyloid-plaque formation. In other words, said "control sample" may also be a "control sample" obtained from the subject/patient to be assessed. In context of the methods provided herein the said (above) also applies, i.e. the control samples may be derived or may originate from the same individual of whom the status of (current) disease/disorder is assessed or of whom, for example, the efficacy of a treatment of a disease is to be monitored. A "control sample" as employed in the methods provided herein may also be a sample, like a biological sample, that originates from a plurality of individuals, like (as non-limiting example) a pooled blood sample from healthy individuals or a pooled blood sample from confirmed diseased individuals (as positive control, for example). In context of this invention the subject/individual to be scrutinized is preferably a mammalian in particular a human being.

The present invention also relates to a method of monitoring the efficacy of a treatment of a disease associated with amyloidogenesis and/or amyloid-plaque formation characterized by the presence of Aβ oligomers in a subject/patient suffering from said disease or being prone to suffering from said disease comprising the steps:

(a) determining in a biological sample obtained from said subject/patient the amount of Aβ oligomers; and (b) comparing the amount of Aβ oligomers determined in a) with a reference amount of Aβ oligomers determined in (a sample from) a control subject/patient (healthy subject), wherein the extent of the difference between said amount determined in (a) and said reference amount is indicative for said efficacy of a treatment of said disease. In one embodiment, these Aβ-oligomers are oligomers of N-terminal truncated Aβ starting with pyroglutamate (AβpE3).

The present invention also relates to a method of predicting the efficacy of a treatment of a disease associated with amyloidogenesis and/or amyloid-plaque formation for a subject/patient suffering from said disease or being prone to suffering from said disease comprising the steps:

(a) determining in biological sample obtained from said subject/patient the amount of Aβ oligomers; and (b) comparing the amount of Aβ oligomers determined in (a) with a reference amount of Aβ oligomers determined in a cell or tissue sample obtained from a control subject/patient, wherein the extent of the difference between said amount of Aβ oligomers determined in (a) and said reference amount of Aβ oligomers is indicative for the predicted efficacy of a treatment of said disease.

In one embodiment, these Aβ-oligomers are oligomers of N-terminal truncated Aβ starting with pyroglutamate (AβpE3). Again, in the method provided here, "reference" or "control" sample may be a sample as defined above.

In still another aspect, the present invention relates to a binding molecule capable of specifically recognizing soluble oligomers of N-terminal truncated Aβ starting with pyroglutamate (AβpE3), and capable of inhibiting Aβ-oligomerization for use in the treatment and/or prevention of an amyloid-related disorder.

The term "binding molecule", as used herein, is intended to refer to any kind of molecule that binds with high affinity to soluble oligomers of AβpE3 and in addition alters the properties of said soluble oligomers. Thus, the binding molecule may be any kind of binding molecule, which is capable of specifically recognizing soluble oligomers of AβpE3, and capable of inhibiting A13-oligomerization. For example, the binding molecule may be an antibody molecule, a polypeptide, peptide, peptidomimetic, or a small molecule having a molecular weight in the range of 250-800 Da, preferably in the range of 300 to 750 Da, such as 350 to 700 Da, or 400 to 650 Da.

Accordingly, the binding molecule may be a natural or synthetic peptide. The synthetic peptide or peptidomimetic may comprise natural or synthetic amino acids, such as standard and non-standard amino acids, including their respective D- and L-forms, unnatural amino acids as well as chemically modified amino acids.

A peptidomimetic is a small protein-like chain designed to mimic a peptide. Peptidomimetics may either be derived from modification of an existing peptide, or by designing similar systems that mimic peptides, such as peptoids and β-peptides. Thus, peptidomimetics may include organic compounds comprising a peptide backbone. Irrespective of the approach, the altered chemical structure of a peptidomimetic, such as altered backbones and the incorporation of non-natural amino acids, is designed to advantageously adjust the molecular properties, e.g. the stability or biological activity.

The small molecule may either be isolated from a natural source or developed synthetically, e.g., by combinatorial chemistry. Examples of such a small molecule include, but are not limited to synthetic compounds, as well as modifications of existing compounds. Also encompassed by the term small molecule are saccharide-, lipid-, peptide-, polypeptide- and nucleic acid-based compounds.

The antibody molecules of the present invention may be a polyclonal antibody, a monoclonal antibody, a recombinant full antibody (immunoglobulin), a F(ab)-fragment, a F(ab)2-fragment, F(v)-fragment, a single-chain antibody, a chimeric antibody, a CDR-grafted antibody, a bivalent antibody-construct, a synthetic antibody, a cross-cloned antibody, a fully-human antibody, a humanized antibody, nanobodies, diabodies, peptide aptamers and the like.

Peptide aptamers are proteins that are designed to interfere with other protein interactions inside cells. They consist of a variable peptide loop attached at both ends to a protein scaffold. This double structural constraint greatly increases the binding affinity of the peptide aptamer to levels comparable to an antibody's (nanomolar range).

As shown in the examples, the inventors found that N-terminal truncated Aβ starting with pyroglutamate (AβpE) can form stable oligomers. In the appended examples, the binding molecules according to the present invention are shown to specifically bind AβpE3 oligomers ending at position 38, 40 or 42 in vitro, as demonstrated by size exclusion chromatography and dot blot. However, the binding molecule according to the present invention does preferably not cross react with oligomers derived from full-length Aβ 1-42 peptides. In brain, the inventive antibodies also recognize AβpE oligomers within neurons and blood vessels. Monomeric or dimeric (non-modified) Aβ peptides are easily secreted by neurons and are cleared via the blood brain barrier. Large amounts of monomeric or dimeric Aβ peptides also aggregate in Alzheimer plaques. This is in contrast to AβpE oligomers that do not aggregate in plaques of healthy non-demented individuals and plaques of patients with sporadic Alzheimer disease. These AβpE oligomers, instead, have a tendency to aggregate within neurons or they may aggregate within blood vessels (cerebral amyloid angiopathy), and are no longer cleared via the blood brain barrier. In consequence, neurons degenerate and cerebral amyloid angiopathy (AβpE oligomers aggregate at blood vessels) develops. Without being bound by theory, Alzheimer disease patients have high levels of AβpE oligomers within neurons and low levels in plasma as the clearance of AβpE oligomers from brain parenchyma is reduced. The levels of AβpE oligomers in plasma may, therefore, be reduced in Alzheimer disease patients. In addition, the inventors have previously demonstrated that Aβ accumulating in plaques is not involved in neuron loss. As AβpE oligomers are not found in plaques, they can not be detoxified by plaque accumulation. Treatment with antibodies or other binding molecules as provided herein against soluble AβpE oligomers as provided in the context of this invention may, therefore, be an appropriate way to reduce the levels AβpE oligomers in the brain and other parts of the body of an individual. Thus, in a preferred embodiment, the AβpE may be AβpE3 or AβpE11, preferably AβpE3. More preferably, AβpE3 is AβpE(3-X), wherein X is 42, 40, 38, 41, 39, or 37, preferably X is 42 or 40, most preferably X is 42. More particularly, binding molecules of the present invention are directed against soluble oligomeric forms of AβpE3, in particular of AβpE3-42.

As used herein, the term "soluble oligomer" means a trimer, a tetramer, a pentamer, a hexamer, a heptamer, an octamer, a nonamer or a decamer, up to a 20 mer of AβpE, preferably AβpE3, more preferably AβpE(3-X), wherein X is 42, 40, 38, 41, 39, or 37, even more preferably wherein X is 42 or 40, most preferably wherein X is 42. Monomers and dimers are not considered as oligomeres, as used in the present context.

As used herein, the term "low molecular weight oligomers" refers to such soluble oligomers made up of 3 to 10 AβpE3, preferable made up of 4 to 6 AβpE3. Thus, in a preferred embodiment, the antibody molecule recognizes soluble AβpE3 oligomers not having a high molecular weight (i.e. oligomers consisting of less than 20 AβpE3 peptides), more preferably the Aβ oligomers are low molecular weight oligomers.

The term "specifically recognizing", as used herein, is intended to mean that the binding molecule specifically only binds and/or detects (i.e. recognizes) soluble oligomeric AβpE3, but not Aβ, or monomers or dimers of AβpE, e.g. AβpE3. Accordingly, in one preferred embodiment, the binding molecule recognizes a conformational epitope or a discontinuous epitope formed by at least two AβpE3 peptides forming said soluble AβpE3 oligomers. In this context, "at least two" means three, four, five, six, seven, eight, nine, ten, eleven, twelve, thirteen, fourteen, fifteen, and up to twenty AβpE3 peptides.

The bonding between a target and a binding molecule in general is dependent on hydrogen bonds, hydrophobic bonds, electrostatic forces, and van der Waals forces. These are all bonds of a weak, non-covalent nature, yet some associations between a target and a binding molecule can be quite strong. Accordingly, the affinity constant for binding of a binding molecule to the soluble AβpE oligomer can span a wide range, extending from about $10^5$ mol$^{-1}$ to about $10^{12}$ mol$^{-1}$, preferably from about $10^6$ mol$^{-1}$ to about $10^{11}$ mol$^{-1}$, more preferably from about $10^7$ mol$^{-1}$ to about $10^{10}$ mol$^{-1}$, even more preferably from about $10^8$ mol$^{-1}$ to about $10^9$ mol$^{-1}$.

In case the binding molecule is an antibody molecule, accurate affinity constants can only be determined for monoclonal antibodies (or recombinantly produced antibody fragments) which are genetically identical molecules recognising one single epitope on the antigen whereas for polyclonal antibodies a broad distribution of affinities may contribute to an apparent affinity constant. The apparent affinity constant may also be caused by the fact that polyclonal antibodies may recognise more than one single epitope on the same antigen. Since antibodies normally harbour more than one binding domain per molecule multiple, co-operative bondings may take place between antibody molecules and their antigens; this effect is termed avidity. Affinity constants are affected by temperature, pH and solvent as well as from the valency of the antibody molecule, and may be calculated from the Scatchard equation. The skilled person will know how to determine whether a binding molecule (specifically) recognizes soluble AβpE3 oligomers, for example by determining the affinity constant of said binding molecule.

In addition, the binding molecule is capable of inhibiting Aβ-oligomerization. The capability of inhibiting Aβ-oligomerization may be determined in a thioflavin T aggregation assay as described in example 13. Briefly, AβpE3-42 peptides are solubilized in 10 mM NaOH at a concentration of 1 mg/ml, sonicated for 5 min, frozen in liquid nitrogen, and stored at −80° C. until use. Aggregation of Aβ peptides is investigated online using ThT aggregation assay (Varian fluorescence spectrophotometer) using an excitation wavelength of 446 nm and emission wavelength of 482 nm. Samples contain 55 µM of AβpE3-42, 50 mM sodium phosphate buffer (pH 7.4), 50 mM NaCl, 20 µM ThT and 0.01% sodium azide. The samples are incubated at 37° C. in a peltier adapter with stirring. Data points are recorded every 10 min during the assay and plotted in a diagram time [min] vs. fluorescence [a.u.] (c.f. FIG. 12). If the binding molecule is capable of inhibiting Aβ-oligomerization, the graph will reach a plateau phase, in which the oligomers are "stabilized" by the binding molecule (c.f. FIG. 12, bottom, triangles), so that they cannot continue to oligomerize and aggregate to a non-soluble oligomer (c.f. FIG. 12, bottom, circles). Thus, in the context of the present invention, a binding molecule is capable of inhibiting Aβ-oligomerization, if the resulting graph shows no inflection point after 250 min, preferably after 300 min, more preferably after 350 min, even more preferably after 400 min, such as after 450 min, and most preferably after 500 min incubation time (c.f. FIG. 12, bottom).

However, the skilled person will be aware of further methods on how to determine the binding constant and the capability of inhibiting Aβ-oligomerization. For example, these properties of the binding molecule may be determined by surface plasmon resonance, e.g. by using a Biacore instrument.

As demonstrated by the inventors, said soluble AβpE3 oligomers appear to act as a seed for oligomerization and aggregation of further Aβ peptides, which may not necessarily be AβpE3 peptides. However, in particular AβpE3 oligomers comprising more than 20 AβpE3 peptides have been found to be neurotoxic. Therefore, in a preferred embodiment, the binding molecule inhibits the seeding effect of soluble AβpE3 oligomers.

Whether a binding molecule inhibits the seeding effect of soluble AβpE3 oligomers may be determined in a cell viability assay as follows.

Toxicity of AβpE3 peptides on neuroblastoma cells is verified as previously published (Harmeier (2009) J Neurosci 29: 7582-7590). Briefly, SH-SY5Y neuroblastoma cells are routinely cultured. After 48 h, medium is replaced by medium containing freshly dissolved monomeric peptides, each at 2 µM concentration in the presence or absence of 1 ng/µl 9D5 antibody (or an equimolar amount of a binding molecule) and incubated for 12 h. Cell viability is determined using MTS assay (Promega), according to the manufacturer's instructions compared to vehicle treated control cells. Accordingly, a binding molecule inhibits the seeding effect of soluble AβpE3 oligomers, if the cell viability is increased by at least 20%, at least 30%, at least 40%, at least 50%, at least 60%, at least 70%, at least 80%, at least 90%, at least 100%, at least 200%, at least 300%, at least 400%, at least 500%, at least 600%, at least 700%, at least 800%, at least 900%, or even at least 1000% compared to the vehicle treated control cells cultivated in the presence of the AβpE3 peptides, but in the absence of the binding molecule.

By which exact way the binding molecule according to the invention inhibits the seeding effect is not yet completely understood. However, it is assumed that the binding molecule either stabilizes the soluble oligomers and thus prevents the cell from toxic high molecular weight oligomers, or even promotes the degradation of the soluble AβpE3 oligomers. For example, in case the binding molecule is an antibody, the opsonized soluble AβpE3 oligomer may be ingested by microglia cells and further degraded.

The binding molecules of the present invention have also therapeutic potential (as illustrated in the appended examples) and can therefore be used in the medical intervention of amyloid-related disorders. In the examples, 5xFAD mice were used, which are prone to suffer from an amyloid-related disorder. Administration of the binding molecule resulted in an alleviation of the symptoms or in the development of an amyloid-related disorder. Accordingly, the binding molecule according to the present invention may be used in the treatment and/or prevention of an amyloid-related disorder. In a preferred embodiment, the amyloid-related disorder is selected from Alzheimer disease, cerebral amyloid angiopathy, dementia, motor neuropathy, Down's syndrome, Creutzfeld Jacob disease, transmissible spongiform encephalopathies, hereditary cerebral hemorrhage with amyloidosis Dutch type, Parkinson's disease, HIV-related dementia, fronto-temporal dementia, Lewy body disease, mixed dementias, head trauma, familial Danish Dementia, familial British Dementia, inclusion body myositis (IBM), or neuronal disorder related to aging. In a more preferred embodiment, the Alzheimer disease is sporadic Alzheimer disease. In another more preferred embodiment, the Alzheimer disease is familiar Alzheimer disease. Still in another preferred embodiment, the transmissible spongiform encephalopathy is selected from Gerstmann-Straussler-Scheinker syndrome, fatal familial insomnia and kuru.

In one particularly preferred embodiment, the binding molecule is an antibody molecule, selected from a polyclonal antibody, a monoclonal antibody, a recombinant full antibody (immunoglobulin), a F(ab)-fragment, a F(ab)$_2$-fragment, a F(v)-fragment, a single-chain antibody, a chimeric antibody, a CDR-grafted antibody, a bivalent antibody-construct, a synthetic antibody, a cross-cloned antibody, a fully-human antibody, a humanized antibody, nanobodies, diabodies, and peptide aptamers and therelike.

Antibodies or immunoglobulins are gamma globulin proteins consisting in their natural form of two large heavy chains and two small light chains linked by disulfide bonds (c.f. FIG. 3). There are five types of mammalian Ig heavy chain: α, δ, ε, γ, and μ. The type of heavy chain present defines the class (isotype) of the antibody; these are IgA, IgD, IgE, IgG, and IgM antibodies, respectively. Each heavy chain has two regions, the constant region and the variable region. The constant region is nearly identical in all naturally occurring antibodies of the same isotype of the same species. A light chain also consists of one constant domain and one variable domain. In mammals there are two types of immunoglobulin light chain, lambda (λ) and kappa (κ).

Although the general structure of all antibodies is very similar, the unique property of a given antibody is determined by the variable (V) regions. More specifically, variable loops, three each the light ($V_L$) and three on the heavy ($V_H$) chain, are responsible for binding to the antigen, i.e. for its antigen specificity.

With regard to the term "full antibody", any antibody is meant that has a typical overall domain structure of a naturally occurring antibody (i.e. comprising a heavy chain of three or four constant domains and a light chain of one constant domain as well as the respective variable domains), even though each domain may comprise further modifications, such as mutations, deletions, or insertions, which do not change the overall domain structure.

In addition, the term "antibody" is intended to comprise all above-mentioned immunoglobulin isotypes, i.e. the antibody may be an IgA, IgD, IgE, IgG, or IgM antibody, including any subclass of these isotypes. Preferably, the antibody is an IgG antibody, more preferably an IgG1 or IgG2 antibody. Since the antibody may be expressed and produced recombinantly, the antibody may also comprise two different constant regions of heavy chains, e.g. one IgG1 and one IgG2 heavy chain, or heavy chains from different species. However, the heavy chains are preferably from the same species. Moreover, the antibody may comprise either a lambda or a kappa light chain.

An "antibody fragment" also contains at least one antigen binding fragment as defined above, and exhibits the same function and specificity as the complete antibody of which the fragment is derived from, e.g. said antibody fragment binds and/or detects an epitope as bound and/or detected by antibody "9D5" (see deposition DSM ACC3056). Fab fragments may be generated by using the enzyme papain to cleave an immunoglobulin. The enzyme pepsin cleaves below the hinge region and, thus, below the disulfide bonds, so that an F(ab)$_2$ fragment is formed. Moreover, the variable regions of the heavy and light chains can be fused together to form a single chain variable fragment (scFv). Thus, in the context of the this invention, an antibody does also comprise variable and light regions, F(ab)-, F(ab)$_2$ fragments, CDR-regions, etc. of the antibodies as disclosed herein. Such "fragments" are known in the art and can readily be used in recombinant technologies. The antibodies of the present invention, accordingly, also comprise humanized or CDR-grafted antibodies as well as genetically/recombinantly engineered "full human" antibodies. Such an engineered antibody is for example an antibody, in which at least one region of an immunoglobulin of one species is fused to another region of an immunoglobulin of another species by genetic engineering in order to reduce its immunogenicity. Also provided are derivatives of antibodies, like single-chain antibodies, diabodies, bispecific single chain antibodies, and antibody-like molecules, such as peptide aptamers and the like.

For example, the antibody molecule may be a monoclonal antibody as, inter alia, obtainable from the deposited hybridomas PG3-38 9D5H6 (DSM ACC3056) or PG3-38 8C4D2 (DSM ACC3066).

The term "monoclonal antibody" as used herein refers to an antibody obtained from a population of substantially homogeneous antibodies, i.e. the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" indicates the character of the antibody as being obtained from a substantially homogeneous population of antibodies, and is not to be constructed as requiring production of the antibody by any particular method. The monoclonal antibodies of the present invention may be made by the hybridoma method first described by Kohler, G. et al., Nature 256 (1975) 495, or may be made by recombinant DNA methods (see, e.g., U.S. Pat. No. 4,816, 567).

Accordingly, in a preferred embodiment, the binding molecule is an antibody, which is produced by the hybridoma deposited with the DSMZ under accession number DSM ACC3056 (antibody 9D5H6) or the hybridoma deposited with the DSMZ under accession number DSM ACC3066 (antibody 8C4D2).

Thus, such an antibody according to the present invention may be produced by and is obtainable from hybridoma P3-X63-Ag8 myeloma cell line as deposited under the cell-line name PG3-38 9D5H6 under Budapest Treaty on the International Recognition of the Deposition of Microorganisms for the Purpose of Patent Procedure in the name (depositors) of the Georg-August-Universität Göttingen, Stiftung Öffentlichen Rechts, Universitätsmedizin and Synaptic Systems GmbH with the DSMZ (Deutsche Sammlung von Mikroorganismen und Zellkulturen GmbH, Braunschweig, Germany) on Apr. 8, 2010 and under Accession Number DSM ACC3056. The antibodies/binding molecules as obtainable from DSM ACC3056 are also described herein as "9D5" or "9D5H6".

Likewise, the invention also relates to an antibody that may be produced by and is obtainable by PG3-38 8C4D2 under Budapest Treaty on the International Recognition of the Deposition of Microorganisms for the Purpose of Patent Procedure in the name (depositors) of the Georg-August-Universität Göttingen, Stiftung Öffentlichen Rechts, Universitätsmedizin and Synaptic Systems GmbH with the DSMZ (Deutsche Sammlung von Mikroorganismen und Zellkulturen, GmbH, Braunschweig, Germany) on May 27, 2010 and under Accession number DSM ACC3066. The antibodies/binding molecules as obtainable from DSM ACC3066 are also described herein as "8C4" or "8C4D2".

The antibody molecule or binding molecule may comprise CDRs and/or variable regions encoded by a nucleic acid molecule as provided by any one of the sequences provided herein. Such an antibody/binding molecule that specifically recognizes Aβ oligomers as disclosed herein may comprise a CDR1 (heavy chain) as encoded by SEQ ID NO: 1 or as encoded by SEQ ID NO: 13, a CDR2 (heavy chain) as encoded by SEQ ID NO: 3 or as encoded by SEQ ID NO: 15, a CDR3 (heavy chain) as encoded by SEQ ID NO: 5 or as encoded by SEQ ID NO: 17, a CDR 1 (light chain) as encoded by SEQ ID NO: 7 or as encoded by SEQ ID NO: 19, a CDR2 (light chain) as encoded by SEQ ID NO: 9 or as encoded by SEQ ID NO: 21, a CDR3 (light chain) as encoded by SEQ ID NO: 11 or as encoded by SEQ ID NO: 23. In one embodiment, the antibody or binding molecule may comprise CDR1 (heavy chain) as encoded by SEQ ID NO: 1, a CDR2 (heavy chain) as encoded by SEQ ID NO: 3, a CDR3 (heavy chain) as encoded by SEQ ID NO: 5, a CDR 1 (light chain) as encoded by SEQ ID NO: 7, a CDR2 (light chain) as encoded by SEQ ID NO: 9, a CDR3 (light chain) as encoded by SEQ ID NO: 11. In another embodiment, the antibody or binding molecule may comprise CDR1 (heavy chain) as encoded by SEQ ID NO: 13, a CDR2 (heavy chain) as encoded by SEQ ID NO: 15, a CDR3 (heavy chain) as encoded by SEQ ID NO: 17, a CDR 1 (light chain) as encoded by SEQ ID NO: 19, a CDR2 (light chain) as encoded by SEQ ID NO: 21, a CDR3 (light chain) as encoded by SEQ ID NO: 23. The appended sequences also provide for amino acid sequences that are encoded by said nucleic acid molecules/DNA and that represent the corresponding CDRs.

Also provided herein is an antibody molecule/binding molecule that comprises the CDRs as defined herein above and in the appended sequence listing and wherein said CDRs are encoded by a nucleic acid molecule that is at least 80%, at least 85%, at least 90%, at least 91%, at least 92%, at least 93%, at least 94%, at least 95%, at least 96%, at least 97%, at least 98%, at least 98%, at least 99% identical to the nucleic acid molecules as provided in any of SEQ ID NOs: 1, 13, 3, 15, 5, 17, 7, 19, 9, 21, 11 and 23. The person skilled in the art is readily in a position to verify the sequence identity of sequences, e.g. by simply comparing said sequences over the whole length of the sequence provided herein. Such a comparison may comprise the usage of computer-assisted means and methods.

Also provided herein are binding molecules/antibodies etc. which comprise CDRs as laid down in any of SEQ ID NOs: 2, 14, 4, 16, 6, 18, 8, 20, 10, 22, 12 or 24. In a preferred embodiment of this invention, such a binding molecule/antibody comprises at least one, at least two or three of the CDRs for any individual antibody chain structure, i.e. a variable heavy chain or a variable light chain. Accordingly, if an inventive antibody/binding molecule comprises a heavy and light chain stretch, in particular a variable heavy and light chain stretch, said antibody molecule comprises at least 2 CDRs, at least 4 CDRs or 6 CDRs as defined herein. In one embodiment, the binding molecule/antibody comprises CDRs as laid down in SEQ ID NOs: 2, 4, 6, 8, 10, and 12. In yet another embodiment, the binding molecule/antibody comprises CDRs as laid down in SEQ ID NOs: 14, 16, 18, 20, 22, and 24.

In one embodiment, said antibody/binding molecule comprises the CDRs as comprised in the variable heavy chain encoded by SEQ ID NO: 25 or by SEQ ID NO: 29 or as comprised in the amino acid sequence provided herein under SEQ ID NO: 26 or 30 and/or it comprises the CDRs as comprised in the variable light chain encoded by SEQ ID NO: 27 or SEQ ID NO: 31 or as comprised in the amino acid sequence provided herein under SEQ ID NO: 28 or 32. Also provided are antibody/binding molecules that comprise the herein defined variable regions (heavy and/or light chains) and/or variants of such variable regions, which are still capable of specifically recognizing Ars oligomers and/or of specifically binding to or detecting AβpE3. These variants may be variants that are at least 80%, at least 85%, at least 90%, at least 91%, at least 92%, at least 93%, at least 94%, at least 95%, at least 96%, at least 97%, at least 98%, at least 98%, at least 99% identical to the whole length of the sequence(s) as provided in the appended sequence listing under SEQ ID NOs: 26, 28, 30 and 32 and as encoded by nucleic acid molecules of SEQ ID NOs: 25, 27, 29 and 31, respectively.

The invention also provides for variants of the herein disclosed variable regions, said variants being still capable of specifically recognizing Aβ oligomers and/or of specifically binding to or detecting AβpE3.

Accordingly, the present invention also provides for antibodies/binding molecules (or compositions, like diagnostic or pharmaceutical compositions comprising the same), wherein said antibodies/binding molecules, antibody molecules or a functional fragment or a functional derivative thereof as described herein, wherein said antibody molecule, fragment or derivative thereof comprises at least one variable region selected from the group consisting of (a) a variable region that comprises a H-CDR1, a H-CDR2 and a H-CDR3 as encoded by the nucleic acid sequence as shown in SEQ ID NOs: 1, 3 and 5;

(b) a variable region that comprises a H-CDR1, a H-CDR2 and a H-CDR3 as encoded by the nucleic acid sequence as shown in SEQ ID NOs: 13, 15 and 17;

(c) a variable region that comprises a L-CDR1, a L-CDR2 and a L-CDR3 as encoded by the nucleic acid sequence as shown in SEQ ID NOs: 7, 9 and 11;

(d) a variable region that comprises a L-CDR1, a L-CDR2 and a L-CDR3 as encoded by the nucleic acid sequence as shown in SEQ ID NOs: 19, 21 and 23;

(e) a variable region as encoded by a nucleic acid molecule comprising the nucleic acid molecule of SEQ ID NOs: 25, 27, 29 or 31;

(f) a variable region comprising the amino acid sequence as provided in SEQ ID NOs: 26, 28, 30 or 32;

(g) a variable region comprising an amino acid sequence which is encoded by a nucleic acid sequence that is at least 80% identical to the nucleic acid sequence as shown in SEQ ID NO: 25, 27, 29 or 31; and (h) a functional fragment or a functional derivative of the antibody as defined in at least one of (a) to (g) wherein said functional fragment or functional derivative binds and/or detects an epitope as bound and/or detected by antibody 9D5H6, as deposited under DSM ACC 3056.

Methods for the preparation of an antibody molecule or binding molecule as described herein may comprise culturing a host cell as described herein under conditions allowing synthesis of said antibody molecule and recovering said antibody molecule from said culture. Conditions allowing synthesis of antibody molecules (or fragments thereof, like variable light or heavy chains or CDRs) according to the present invention may differ for each host cell used and are well known in the art.

For example, the present invention relates to a method for the preparation of an antibody molecule (or fragments or derivatives thereof) capable of specifically recognizing Aβ oligomers, in particular AβpE3 oligomers, wherein said antibody molecule binds and/or detects an epitope as bound and/or detected by antibody "9D5", wherein the method comprises culturing the said antibody expressing hybridoma cell line and/or a host cell such as a CHO cell and derivates thereof like DG44, CHO-K1 and/or other cells like AG8 and/or HEK293 cells under conditions allowing synthesis of said antibody molecule and recovering said antibody molecule from said culture. As another example, the present invention relates to a method for the preparation of an antibody molecule capable of specifically recognizing Aβ oligomers, in particular AβpE3 oligomers, wherein said antibody molecule binds and/or detects an epitope as bound and/or detected by antibody "9D5" and is capable of staining blood vessels in a tissue sample, wherein the method comprises culturing a host cell as described herein under conditions allowing synthesis of said antibody molecule and recovering said antibody molecule from said culture. Furthermore, the present invention relates to a hybridoma which produces an antibody molecule provided and described herein. The antibody molecule prepared by the method provided herein may be "9D5" or "8C4", or a fragment or a derivative thereof.

In another preferred embodiment, the binding molecule is an antibody molecule, wherein said antibody molecule recognizes an epitope as recognized by antibody 9D5H6, wherein antibody 9D5H6 is obtainable from the hybridoma deposited with the DSMZ under accession number DSM ACC3056. In other words, the present invention describes and provides an antibody molecule capable of specifically recognizing Aβ oligomers in particular AβpE3 oligomers, wherein said antibody molecule may bind and/or detect an epitope as bound and/or detected by antibody "9D5". In context of the present invention and as further described and exemplified herein, said binding and/or detecting may be verified by immunoblotting analysis and/or immunostaining and/or immunoisolation or also comparative dot-blotting. An example of such an antibody is "8C4" (as deposited on May 27, 2010 with DSMZ, GmbH, Braunschweig, under Accession Nummer DSM ACC3066). As shown in the appended examples, "8C4" recognizes an epitope as recognized by "9D5".

In the context of the present invention, an "antibody fragment" comprises a portion of an intact antibody molecule as described herein and is preferably capable of specifically recognizing an epitope as recognized by antibody "9D5" (see deposition DSM ACC3056).

In the context of the present invention and as further described and exemplified herein, said recognizing of the same epitope may be verified by immunoblotting analysis and/or immunostaining and/or immunoisolation or also comparative dot-blotting. Methods for performing immunoblotting analysis, immunoisolation and immunostaining are well known in the art (Bosman F T. Some recent developments in immunocytochemistry. Histochem J. 1983 March; 15(3):189-200) and are also described and exemplified herein below. Non-limiting examples for immunoblotting are dot blot and/or western blot analysis (Towbin et al. (1979) Proc. Nat. Acad. Sci. 76: 4350-4354). Non-limiting examples for immunostaining are immunohistochemistry, immunocytochemistry (Spector and Goldmann (1998) Cells: A laboratory manual, vol. 2: Light microscopy and cell structure), flow cytometry (Ormerod (2000) Flow Cytometry: A Practical Approach (3rd edition; or Nebe-von-Caron G., Stephens P. J., Hewitt C. J., Powell J. R., Badley R. A.: "Analysis of bacterial function by multi-colour fluorescence flow cytometry and single cell sorting. Journal of Microbiolgical Methods. 2000; 42:97-114), ELISA (Engvall, E. & Perlman, P. (1971): Enzyme-linked immunosorbent assay (ELISA). Quantitative assay of immunoglobulin G. In: Immunochemistry. 8, 871-874; Goldsby, R. A., Kindt, T. J., Osborne, B. A. & Kuby, J. Enzyme-Linked Immunosorbent Assay. In: Immunology, 5th ed., pp. 148-150. W. H. Freeman, New York, 2003) and/or immunoelectron microscopy (Matutes and Catovsky (1982) Clin. Exp. Immunol. 50:416-425). Non-limiting examples for immunoisolation are immunoprecipitation (Kessler (1975) J. Immunol. 115:1617-1623), immunoaffinity purification (Gersten and Marchalonis (1978) J. Immunol. Methods 24:305-309) and/or ELISA (Butler (1986) Mol Immunol. 23:971-982; Tanaka H. et al. (2007): Eastern blotting and immunoaffinity concentration using monoclonal antibody for ginseng saponins in the field of traditional chinese medicines. J Agric Food Chem.; 55(10):3783-7; Renart, J. et al. (1979): Transfer of proteins from gels to diazobenzyloxymethyl-paper and detection with antisera: a method for studying antibody specificity and antigen structure. In: Proc. Natl. Acad. Sci. U.S.A. 76:3116-3120; Towbin, H. et al. (1979): Electrophoretic transfer of proteins from polyacrylamide gels to nitrocellulose sheets: procedure and some applications. In: Proc. Natl. Acad. Sci. U.S.A. 76:4350-4354; Burnette, W. N. (1981): Western blotting: electrophoretic transfer of proteins from sodium dodecyl sulfate-polyacrylamide gels to unmodified nitrocellulose and radiographic detection with antibody and radioiodinated protein A. In: Anal. Biochem. 112: 195-203).

One example of a quantitative immunoisolation may be an ELISA test. Here, as non-limiting example, ninety-six-well plates may be coated overnight with monoclonal antibody 9D5H6 in carbonate buffer pH 9.6 at 4° C. Subsequently, the plates may be washed three times with PBS and blocked for 2 h with PBS containing about 5% w/v milk powder and about 0.05% Tween 20 at room temperature. Plates may then be washed three times with PBS and 0.1% azide in PBS (e.g., 20

μl thereof) may be added for blocking of peroxidases. Samples may then be added and incubated for 1 h at 37° C. The plates may be washed three times with PBS and incubated with biotinylated detection antibody for 1 h at 37° C. Plates may then again be washed three times with PBS and Streptavidin HRP may be added at about 1:4000 dilution in PBS/1% BSA and then incubated for 1 h at 37° C. The plates may again be washed three times with PBS and subsequently developed with peroxidase substrate. In context of the present invention, the immunostaining may be performed with different kinds of biological samples such as cell samples, tissue samples such as brain samples, or blood samples such as serum samples as well as control fluid samples. The biological samples may be in vitro samples. As an example in context of the present invention, the biological sample with which the immunostaining is to be performed, e.g., a brain sample, may be derived from a non-human animal, e.g., a transgenic non-human animal. As another example, the biological sample with which the immunostaining is to be performed may also be a brain sample derived from a human being, e.g., an in vitro brain sample derived from a human being.

In the context of the present invention, exemplarily, antibodies as provided herein ("9D5" and "8C4" as obtainable from hybridomas as deposited with DSMZ, Deutsche Sammlung von Mikroorganismen and Zellkulturen, Germany under DSM ACC3056 and DSM ACC3066, respectively, and as deposited at DSMZ on May 27, 2010) were characterized by immunohistochemistry in APP/PS1KI and 5xFAD mice, sporadic and familial AD cases and healthy controls. While plaques in certain mouse models could be stained using "9D5" or "8C4" antibody, only a fraction of "9D5" or "8C4" plaques were positive in patients with sporadic AD and familial AD including those carrying mutations in APP (arctic and Swedish) and Presenilin-1 (PS1) mutation carriers. However, abundant intraneuronal staining was seen in transgenic models, as well as in all familial Alzheimer Disease (AD) cases and some sporadic AD cases. In addition, strong immunostaining was observed in many human AD cases in blood vessels, e.g., in tissue samples. It was surprisingly found that staining with antibodies of the present invention was negligible in healthy control specimens although some of these healthy human controls harboured many plaques. In both AD mouse models exemplified herein, intraneuronal staining with antibodies of the invention appeared during aging coinciding with the onset of learning and memory deficits.

Thus, the antibody molecules/binding molecules described and provided in context of the present invention may be capable of staining blood vessels and/or cells in a biological sample. Such biological samples may be tissue samples such as brain samples or blood samples such as serum samples. For example, the antibodies described and provided herein may be capable of staining blood vessels in a tissue sample.

The present invention further relates to a composition comprising a binding molecule, preferably an antibody molecule as described herein and/or as prepared by the method as described herein.

In one embodiment, the composition comprising an antibody molecule/binding molecule or a fragment or derivative thereof as described and provided herein and/or as prepared by the method as described and provided herein may be a diagnostic composition.

In another embodiment, said composition may further comprise a pharmaceutically acceptable carrier. Accordingly, in another aspect, the present invention also relates to a pharmaceutical composition comprising a binding molecule as defined above, such as an antibody molecule or a fragment or derivative thereof as described and provided herein and/or as prepared by the method as described herein and further comprising a pharmaceutically acceptable carrier, excipient and/or diluent.

The choice of carrier may depend upon route of administration and concentration of the active agent(s) and the pharmaceutical composition may be in the form of a lyophilised composition or an aqueous solution. Generally, an appropriate amount of a pharmaceutically acceptable salt is used in the carrier to render the composition isotonic. Examples of the carrier include but are not limited to phosphate buffered saline, Ringer's solution, dextrose solution, water, emulsions, such as oil/water emulsions, various types of wetting agents, sterile solutions, etc. Preferably, acceptable excipients, carriers, or stabilisers are non-toxic at the dosages and concentrations employed, including buffers such as citrate, phosphate, and other organic acids; salt-forming counter-ions, e.g. sodium and potassium; low molecular weight (>10 amino acid residues) polypeptides; proteins, e.g. serum albumin, or gelatine; hydrophilic polymers, e.g. polyvinylpyrrolidone; amino acids such as histidine, glutamine, lysine, asparagine, arginine, or glycine; carbohydrates including glucose, mannose, or dextrins; monosaccharides; disaccharides; other sugars, e.g. sucrose, mannitol, trehalose or sorbitol; chelating agents, e.g. EDTA; non-ionic surfactants, e.g. Tween, Pluronics or polyethylene glycol; antioxidants including methionine, ascorbic acid and tocopherol; and/or preservatives, e.g. octadecyldimethylbenzyl ammonium chloride; hexamethonium chloride; benzalkonium chloride, benzethonium chloride; phenol, butyl or benzyl alcohol; alkyl parabens, e.g. methyl or propyl paraben; catechol; resorcinol; cyclohexanol; 3-pentanol; and m-cresol). Suitable carriers and their formulations are described in greater detail in Remington's Pharmaceutical Sciences, 17th ed., 1985, Mack Publishing Co.

Similar to the antibody molecules of the invention, such pharmaceutical compositions can be used in the treatment of an amyloid-related disorder in a subject suffering or prone to suffer from an amyloid-related disorder.

In a preferred embodiment, the amyloid-related disorder is selected from Alzheimer disease, cerebral amyloid angiopathy, dementia, motor neuropathy, Down's syndrome, Creutzfeld Jacob disease, transmissible spongiform encephalopathies, hereditary cerebral hemorrhage with amyloidosis Dutch type, Parkinson's disease, HIV-related dementia, fronto-temporal dementia, Lewy body disease, mixed dementias, head trauma, familial Danish Dementia, familial British Dementia, inclusion body myositis (IBM), or neuronal disorder related to aging. In a more preferred embodiment, the Alzheimer disease is sporadic Alzheimer disease. In another more preferred embodiment, the Alzheimer disease is familiar Alzheimer disease. Still in another preferred embodiment, the transmissible spongiform encephalopathies is selected from Gerstmann-Straussler-Scheinker syndrome, fatal familial insomnia and kuru.

A "subject" as used herein is, may be a non-human animal or a human. Preferably, the subject is a mammal such as a horse, cow, pig, mouse, rat, guinea pig, cat, dog, goat, sheep, non-human primate, or a human. The subject may be a healthy subject, a subject having/suffering from a disease associated with amyloidogenesis and/or amyloid-plaque formation, patients, or subjects showing/having susceptibility for the development of and/or being prone to suffer/develop a disease associated with amyloidogenesis and/or amyloid-plaque formation, i.e. an amyloid-related disorder (e.g. carrying a genomic mutation which correlates with the occurrence of an amyloid-related disorder, such as swedish mutation, arctic mutation, etc.).

The pharmaceutical composition may be administered to the subject at a suitable dose, i.e. about 1 ng/kg body weight to about 100 mg/kg body weight of a subject. In one embodiment of the present invention, the composition comprising an antibody molecule as described and provided herein and/or as prepared by the method as described and provided herein comprises the antibody molecule (or a fragment or a derivative thereof) in an amount of about 10 ng/kg to about 5 mg/kg or to about 10 mg/kg per body weight.

Thus, in a preferred embodiment, the composition is administered to said subject at a dose of about 1 ng/kg body weight to about 100 mg/kg body weight of said subject, preferably at a dose of about 10 ng/kg to about 10 mg/kg, more preferably at a dose of of about 10 ng/kg to about 5 mg/kg per body weight.

Administration of the compositions comprising an antibody molecule as described and provided herein and/or as prepared by the method as described and provided herein may be effected or administered by different ways, e.g., enterally, orally (e.g., pill, tablet (buccal, sublingual, orally, disintegrating, capsule, thin film, liquid solution or suspension, powder, solid crystals or liquid), rectally (e.g., suppository, enema), via injection (e.g., intravenously, subcutaneously, intramuscularly, intraperitoneally, intradermally) via inhalation (e.g., intrabronchially), topically, vaginally, epicutaneously, or intranasally. In a preferred embodiment, the composition is administered via injection, in particular intravenously, subcutaneously, intramuscularly, intraperitoneally, or intradermally; more particular wherein the composition is administered intravenously. In still another more preferred embodiment, the composition is administered directly into cerebral fluid or selected brain regions, i.e. intracranially.

The dosage regimen will be determined by the attending physician and clinical factors. As is well known in the medical arts, dosages for any one patient depends upon many factors, including the patient's size, body surface area, age, the particular compound to be administered, sex, time and route of administration, general health, and other drugs being administered concurrently. The compositions comprising a binding molecule, preferably an antibody molecule as described and provided herein and/or as prepared by the method as described herein may be administered locally or systemically. Administration will preferably be intravenously but may also be an administration that is subcutaneously, intramuscularly, intraperitoneally, intracranially or directly into the cerebral fluid or selected brain regions. The compositions comprising a binding molecule, preferably an antibody molecule or a fragment or derivative thereof as described and provided herein and/or as prepared by the method as described and provided herein may also be administered directly to the target site, e.g., by biolistic delivery to an internal or external target site or by catheter to a site in an artery or a vein.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like. Furthermore, also doses below or above of the exemplary ranges described hereinabove are envisioned, especially considering the aforementioned factors.

In still another aspect, the present invention relates to a method of treating or preventing an amyloid-related disorder, the method comprising administering a binding molecule capable of specifically recognizing soluble oligomers of N-terminal truncated Aβ starting with pyroglutamate (AβpE3), and capable of inhibiting Aβ-oligomerization to a subject suffering or prone to suffer from said amyloid-related disorder.

Preferably, said method comprises the same preferred embodiments as described above with regard to the other aspects, and the same definitions apply accordingly.

Thus, in a preferred embodiment, said AβpE3 is AβpE(3-X), wherein X is 42, 40, 38, 41, 39, or 37, preferably X is 42.

Further, the capability of inhibiting Aβ-oligomerization is preferably determined in a thioflavin T aggregation assay as described in example 13.

In another preferred embodiment, the binding molecule is selected from an antibody molecule, a polypeptide, peptide, peptidomimetic, or a small molecule having a molecular weight in the range of 250-800 Da, as described and defined above.

In still another preferred embodiment, said binding molecule inhibits the seeding effect of AβpE3 oligomers. An assay for determining this property of the binding molecule is exemplified above and also described in the examples.

Preferably, said binding molecule recognizes a conformational epitope formed by at least two Aβ-pE3 peptides forming said soluble AβpE3 oligomers.

Preferably, the amyloid-related disorder is selected from Alzheimer disease, cerebral amyloid angiopathy, dementia, motor neuropathy, Down's syndrome, Creutzfeld Jacob disease, transmissible spongiform encephalopathies, hereditary cerebral hemorrhage with amyloidosis Dutch type, Parkinson's disease, HIV-related dementia, fronto-temporal dementia, Lewy body disease, mixed dementias, head trauma, familial Danish Dementia, familial British Dementia, inclusion body myositis (IBM), or neuronal disorder related to aging. In a more preferred embodiment, the Alzheimer disease is sporadic Alzheimer disease. In another more preferred embodiment, the Alzheimer disease is familiar Alzheimer disease. In still another preferred embodiment, the transmissible spongiform encephalopathies is selected from Gerstmann-Straussler-Scheinker syndrome, fatal familial insomnia and kuru.

In a particularly preferable embodiment, the binding molecule is an antibody molecule, selected from a polyclonal antibody, a monoclonal antibody, a recombinant full antibody (immunoglobulin), a F(ab)-fragment, a F(ab)$_2$-fragment, a F(v)-fragment, a single-chain antibody, a chimeric antibody, a CDR-grafted antibody, a bivalent antibody-construct, a synthetic antibody, a cross-cloned antibody, a fully-human antibody, a humanized antibody, nanobodies, diabodies, and peptide aptamers.

Preferably, said antibody molecule recognizes an epitope as recognized by antibody 9D5H6, wherein antibody 9D5H6 is obtainable from the hybridoma deposited with the DSMZ under accession number DSM ACC3056. Assays for determining whether an antibody molecule recognizes an epitope as recognized by antibody 9D5H6 are described above.

In another preferred embodiment, said antibody molecule is an antibody produced by the hybridoma deposited with the DSMZ under accession number DSM ACC3056 (antibody 9D5H6) or the hybridoma deposited with the DSMZ under accession number under DSM ACC3066 (antibody 8C4D2).

In a more preferred embodiment, the binding molecule is in the form of a pharmaceutical composition, further comprising a pharmaceutically acceptable carrier, excipient and/or diluent.

Said composition is preferably administered to said subject at a dose of about 1 ng/kg body weight to about 100 mg/kg body weight of said subject, preferably at a dose of about 10 ng/kg to about 10 mg/kg, more preferably at a dose of of about 10 ng/kg to about 5 mg/kg per body weight.

Further, said composition is preferably administered via injection, in particular intravenously, subcutaneously, intramuscularly, intraperitoneally, or intradermally; more particular wherein the composition is administered intravenously. In one preferred embodiment, the composition is administered directly into cerebral fluid or selected brain regions.

In another important aspect, the present invention provides a method of inhibiting the formation or the seeding effect of oligomers of AβpE3 associated with an amyloid-related disorder in a subject, who has or is prone to form said oligomers, comprising administering a binding molecule capable of specifically recognizing soluble AβpE3 oligomers, and capable of inhibiting Aβ-oligomerization to said subject.

Generally, the metes and bounds of this aspect are as defined above.

In a preferred embodiment, said AβpE3 is AβpE(3-X), wherein X is 42, 40, 38, 41, 39, or 37, preferably X is 42.

Further, the capability of inhibiting Aβ-oligomerization is determined in a thioflavin T aggregation assay as described in example 13.

The binding molecule may be selected from an antibody molecule, a polypeptide, peptide, peptidomimetic, or a small molecule having a molecular weight in the range of 250-800 Da.

In still another preferred embodiment, said binding molecule inhibits the seeding effect of AβpE3 oligomers. An assay for determining this property of the binding molecule is exemplified above and also described in the examples.

In a particularly preferred embodiment, said binding molecule recognizes a conformational epitope formed by more than one Aβ-pE3 peptide forming said soluble AβpE3 oligomers.

In addition, the amyloid-related disorder is preferably selected from Alzheimer disease, cerebral amyloid angiopathy, dementia, motor neuropathy, Down's syndrome, Creutzfeld Jacob disease, transmissible spongiform encephalopathies, hereditary cerebral hemorrhage with amyloidosis Dutch type, Parkinson's disease, HIV-related dementia, fronto-temporal dementia, Lewy body disease, mixed dementias, head trauma, familial Danish Dementia, familial British Dementia, inclusion body myositis (IBM), or neuronal disorder related to aging. In a more preferred embodiment, the Alzheimer disease is sporadic Alzheimer disease. In another more preferred embodiment, the Alzheimer disease is familiar Alzheimer disease. In still another preferred embodiment, the transmissible spongiform encephalopathies is selected from Gerstmann-Straussler-Scheinker syndrome, fatal familial insomnia and kuru.

Additionally, the binding molecule is an antibody molecule, selected from a polyclonal antibody, a monoclonal antibody, a recombinant full antibody (immunoglobulin), a F(ab)-fragment, a F(ab)$_2$-fragment, a F(v)-fragment, a single-chain antibody, a chimeric antibody, a CDR-grafted antibody, a bivalent antibody-construct, a synthetic antibody, a cross-cloned antibody, a fully-human antibody, a humanized antibody, nanobodies, diabodies, and peptide aptamers.

Preferably, said antibody molecule recognizes an epitope as recognized by antibody 9D5H6, wherein antibody 9D5H6 is obtainable from the hybridoma deposited with the DSMZ under accession number DSM ACC3056. Alternatively, said antibody moleculemay be an antibody produced by the hybridoma deposited with the DSMZ under accession number DSM ACC3056 (antibody 9D5H6) or the hybridoma deposited with the DSMZ under accession number DSM ACC3066 (antibody 8C4D2).

In still a more preferred embodiment, the binding molecule is in the form of a pharmaceutical composition, further comprising a pharmaceutically acceptable carrier, excipient and/or diluent.

In particular, the composition may be administered to said subject at a dose of about 1 ng/kg body weight to about 100 mg/kg body weight of said subject, preferably at a dose of about 10 ng/kg to about 10 mg/kg, more preferably at a dose of about 10 ng/kg to about 5 mg/kg per body weight.

Preferably, the composition is administered via injection, in particular intravenously, subcutaneously, intramuscularly, intraperitoneally, or intradermally; more particular wherein the composition is administered intravenously. In a preferred embodiment, the composition is administered directly into cerebral fluid or selected brain regions.

Further, a binding substance such as an antibody molecule, polypeptide, peptide, peptidomimetic, or a small molecule having a molecular weight in the range of 250-800 Da is contemplated, wherein the binding substance has the following characteristics:

a) being capable of inhibiting the oligomerization of N-terminal truncated Aβ starting with pyroglutamate (AβpE3) by binding to soluble AβpE3, wherein said AβpE3 is AβpE(3-X), wherein X is 42, 40, 38, 41, 39, or 37, preferably X is 42, and b) being capable of inhibiting the seeding effect of AβpE3, and c) having no disintegrating effect on insoluble, aggregated amyloid-plaques, for use in the treatment and/or prevention of an amyloid-related disorder.

In this context, also a method of treating or preventing an amyloid-related disorder is contemplated, the method comprising administering a binding substance such as an antibody molecule, polypeptide, peptide, peptidomimetic, or a small molecule having a molecular weight in the range of 250-800 Da to a subject suffering or prone to suffer from said amyloid-related disorder, and wherein the binding substance has the following characteristics:

a) being capable of inhibiting the oligomerization of N-terminal truncated Aβ starting with pyroglutamate (AβpE3) by binding to soluble AβpE3, wherein said AβpE3 is AβpE(3-X), wherein X is 42, 40, 38, 41, 39, or 37, preferably X is 42, and b) being capable of inhibiting the seeding effect of AβpE3, and c) having no disintegrating effect on insoluble, aggregated amyloid-plaques.

Preferably the binding substance is in the form of a pharmaceutical composition, comprising a pharmaceutically acceptable carrier, excipient and/or diluent.

Inhibition of oligomerization of N-terminal truncated Aβ starting with pyroglutamate (AβpE3) may be determined in a similar fashion as described above, e.g. in the context of "inhibiting Aβ-oligomerization". Whether a binding substance inhibits the seeding effect of soluble AβpE3 may be determined in a cell viability assay as described above. Whether a binding substance has a disintegrating effect on amyloid plaques may be determined in vitro, or more preferably in vivo using a non-human AD model organism, e.g. by determining the alteration in the plaque load of the cortex in a test animal. Such methods are further exemplified in Example 15 and 18 below.

For example, male 5XFAD mice are treated with an amount of the binding substance, equal to 10 mg/kg of an antibody for 4 months (3 to 7 months of age treatment period) by a weekly intraperitoneal injection. Then the animal is sacrificed, and 4 μm paraffin sections are pretreated with 0.3% H202 in PBS to block endogenous peroxidases and antigen retrieval is achieved by boiling sections in 0.01 M citrate buffer pH 6.0, followed by 3 min incubation in 88% formic acid. Primary plaques detecting antibodies are incubated overnight, followed by incubation with biotinylated secondary antibodies before staining is visualized, e.g. using the ABC method with Vectastain kit (Vector Laboratories) and diaminobenzidine as chromogen. Additionally, IBA1 may be used as a marker for microglia cells (IBA1 (rabbit) antisera from Wako Pure Chemicals).

Extracellular Aβ load is then evaluated in cortex using an Olympus BX-51 microscope equipped with an Olympus DP-50 camera and the ImageJ software (V1.41, NIH, USA). Serial images of 40× magnification (hippocampus) and 100× (cortex) are captured on six sections per animal which are 30 μm afar from each other. Using ImageJ the pictures are binarized to 16-bit black and white images and a fixed intensity threshold is applied defining the DAB staining.

In still another aspect, the present invention provides a method for identifying agents useful in the treatment and/or prevention of an amyloid-related disorder, comprising the steps of
  (i) incubating monomeric AβpE3 with a candidate agent and determining the rate of oligomerization and aggregation; and
  (ii) incubating monomeric AβpE3, which has not been incubated with a candidate agent and determining the rate of oligomerization and aggregation;
wherein a decreased rate of oligomerization and aggregation determined in step (i) compared to the rate of oligomerization and aggregation determined in step (ii) is indicative of an agent useful in the treatment and/or prevention of an amyloid-related disorder.

In a preferred embodiment, said AβpE3 is AβpE(3-X), wherein X is 42, 40, 38, 41, 39, or 37, preferably X is 42.

In a particular embodiment, the rate of oligomerization and aggregation is determined in a thioflavin T aggregation assay as described in example 13. The "rate of oligomerization and aggregation" means the rate, in which soluble oligomers (oligomerization) or even non-soluble aggregates (aggregation) are formed. Briefly, AβpE3-42 peptides are solubilized in 10 mM NaOH at a concentration of 1 mg/ml, sonicated for 5 min, frozen in liquid nitrogen, and stored at −80° C. until use. Aggregation of Aβ peptides is investigated online using ThT aggregation assay (Varian fluorescence spectrophotometer) using an excitation wavelength of 446 nm and emission wavelength of 482 nm. Samples contain 55 μM of AβpE3-42, 50 mM sodium phosphate buffer (pH 7.4), 50 mM NaCl, 20 μM ThT and 0.01% sodium azide. The samples are incubated at 37° C. in a peltier adapter with stirring. Data points are recorded every 10 min during the assay and plotted in a diagram time [min] vs. fluorescence [a.u.] (c.f. FIG. 12).

The rate of oligomerization and aggregation may be determined as the gradient of the graph in the interval of 200 to 500 min, preferably 250 to 450 min, more preferably, 300 to 400 min.

In the context of the present invention, a decrease in the rate of oligomerization and aggregation determined in step (i) of at least 10%, at least 20%, preferably at least 30%, such as at least 40%, more preferably at least 50%, such as at least 60%, or at least or at least 70%, even more preferably at least 80%, and most preferably of at least 90%, such as 100%, compared to the rate of oligomerization and aggregation determined in step (ii) (100%) is indicative of an agent useful in the treatment and/or prevention of an amyloid-related disorder.

However, the skilled person will be aware of further methods on how to determine the binding constant and the capability of inhibiting Aβ-oligomerization. For example, these properties of the binding molecule may be determined by surface plasmon resonance, e.g. by using a Biacore instrument.

In one preferred embodiment, an antibody produced by the hybridoma deposited with the DSMZ under accession number DSM ACC3056 (antibody 9D5H6) or the hybridoma deposited with the DSMZ under accession number DSM ACC3066 (antibody 8C4D2) is used as a reference control.

In another preferred embodiment, the candidate agent is an antibody molecule, a polypeptide, peptide, or a peptidomimetic. Alternatively, the candidate agent may be a small molecule, either isolated from natural sources or developed synthetically, e.g., by combinatorial chemistry. Preferably, the small molecule has a molecular weight in the range of 250-800 Da, more preferably in the range of 300 to 750 Da, such as 350 to 700 Da, or 400 to 650 Da. The skilled person in the field of drug discovery and development will understand that the precise source of candidate agents is not critical to the methods of the invention. Accordingly, virtually any number of chemical extracts or compounds can be used in the method described herein. Examples of such candidate agents include, but are not limited to, plant-, fungal-, prokaryotic- or animal-based extracts, fermentation broths, and synthetic compounds, as well as modifications of existing compounds. Also encompassed by the term "candidate agent" are saccharide-, lipid-, peptide-, polypeptide- and nucleic acid-based compounds. Synthetic compound libraries are commercially available, e.g., from Brandon Associates (Merrimack, N.H.) and Aldrich Chemical (Milwaukee, Wis.). Alternatively, libraries of natural compounds in the form of bacterial, fungal, plant, and animal extracts are commercially available from a number of sources, e.g., Biotics (Sussex, UK), Xenova (Slough, UK), Harbor Branch Oceangraphics Institute (Ft. Pierce, Fla.), and PharmaMar, U.S.A. (Cambridge, Mass.). Alternatively, natural and synthetically produced libraries may be generated, according to methods well known in the art.

Alternatively, the candidate agent may be an antibody molecule, selected from a polyclonal antibody, a monoclonal antibody, a recombinant full antibody (immunoglobulin), a F(ab)-fragment, a F(ab)$_2$-fragment, a F(v)-fragment, a single-chain antibody, a chimeric antibody, a CDR-grafted antibody, a bivalent antibody-construct, a synthetic antibody, a cross-cloned antibody, a fully-human antibody, a humanized antibody, nobodies, diabodies, and peptide aptamers.

More specifically, the amyloid-related disorder is selected from Alzheimer disease, cerebral amyloid angiopathy, dementia, motor neuropathy, Down's syndrome, Creutzfeld Jacob disease, transmissible spongiform encephalopathies, hereditary cerebral hemorrhage with amyloidosis Dutch type, Parkinson's disease, HIV-related dementia, fronto-temporal dementia, Lewy body disease, mixed dementias, head trauma, familial Danish Dementia, familial British Dementia, Inclusion body myositis (IBM), or neuronal disorder related to aging. The Alzheimer disease may be sporadic Alzheimer disease. Alternatively, the Alzheimer disease may be familiar Alzheimer disease. In still another preferred embodiment, the transmissible spongiform encephalopathies is selected from Gerstmann-Straussler-Scheinker syndrome, fatal familial insomnia and kuru.

The present invention also relates to nucleic acid molecules encoding the antibody molecules/binding molecules provided and described herein. Furthermore, nucleic acid molecules encoding CDRs and/or variable regions of such inventive antibodies or binding molecules are provided herein. The term "nucleic acid molecule" in the context with the present invention is known in the art and may refer to DNA or RNA, or hybrids thereof or any modification thereof that is known in the art (see, e.g., U.S. Pat. No. 5,525,711, U.S. Pat. No. 4,711,955, U.S. Pat. No. 5,792,608 or EP 302175 for examples of modifications). Nucleic acid residues comprised by the nucleic acid molecules described herein may be naturally occurring nucleic acid residues or artificially produced nucleic acid residues. Examples for nucleic acid residues are adenine (A), guanine (G), cytosine (C), thymine (T), uracil (U), xanthine (X), and hypoxanthine (HX). In context with the present invention, thymine (T) and uracil (U) may be used interchangeably depending on the respective type of polynucleotide. For example, as the skilled person is aware of, a thymine (T) as part of a DNA corresponds to a uracil (U) as part of the corresponding transcribed mRNA. The nucleic acid molecule provided and described in context with the present invention may be single- or double-stranded, linear or circular, natural or synthetic, and without any size limitation.

Corresponding nucleic acid molecules are exemplified in the sequences provided herein, inter alia, in the nucleic acid molecules encoding CDRs as provided in any of SEQ ID NOs: 1, 3, 5, 7, 9, 11, 13, 15, 17, 19, 21 or 23 or encoding variable regions and as provided under SEQ ID NOs: 25, 27, 29 or 31, and variants thereof, as further described above. Also provided herein are nucleic acid molecules encoding CDRs and/or variable regions as comprised in the hybridomas deposited under DSM ACC3056 or under DSM ACC3066 and as provided herein.

The present invention further relates to vectors containing a nucleic acid molecule of the present invention encoding an antibody molecule described herein. The term "vector" as used herein particularly refers to plasmids, cosmids, viruses, bacteriophages and other vectors commonly used in genetic engineering. In a preferred embodiment, the vectors of the invention are suitable for the transformation of cells, like fungal cells, cells of microorganisms such as yeast or prokaryotic cells. Such vectors are suitable for stable transformation of bacterial cells, for example to express the antibodies or binding molecules of the present invention. However, it is also a gist of this invention that such vectors are suitable to express the antibodies/binding molecules of the present invention in eukaryotic cells, like CHO-cells and derivates thereof like DG44, CHO-KI and/or other cells like AG8, HEK293.

Accordingly, the vector as provided may be an expression vector. Generally, expression vectors have been widely described in the literature. These vectors may not only contain a selection marker gene and a replication-origin ensuring replication in the host selected, but also a promoter, and in most cases a termination signal for transcription. Between the promoter and the termination signal there is preferably at least one restriction site or a polylinker which enables the insertion of a nucleic acid sequence/molecule desired to be expressed.

It is to be understood that when the vector described herein is generated by taking advantage of an expression vector known in the prior art that already comprises a promoter suitable to be employed in context of this invention, for example expression of a binding molecule or antibody (or a fragment or derivative thereof) as described herein above, the nucleic acid construct is inserted into that vector in a manner the resulting vector comprises only one promoter suitable to be employed in context of this invention. The skilled person knows how such insertion can be put into practice. For example, the promoter can be excised either from the nucleic acid construct or from the expression vector prior to ligation.

Non-limiting examples of the vectors of the present invention are the plasmid vectors pOptivec and pcDNA3.x series (Invitrogen), pESG-IBA, pCSG-IBA or pYSG-IBA vectors comprising a nucleic acid molecule described in the present invention. Further examples of vectors suitable to comprise a nucleic acid molecule of the present invention to form the vector provided herein are known in the art and are, for example other vectors for, e.g., bacterial expression systems such as vectors of the pET series (Novagen), pQE vectors (Qiagen), or other useful vectors, like pASK-IBA, pASG-IBA, pPSG-IBA vectors (IBA) or pGex vectors (GE-Healthcare).

In an additional embodiment, the present invention relates to a host cell comprising the nucleic acid molecule and/or the vector described above. Preferably, the host cell may be a prokaryotic cell, for example, a bacterial cell. As a non limiting example, the host cell may be a CHO cell and derivates thereof like DG44, CHO-KI and/or other cells like AG8 and/or HEK293 cells. The host cell is intended to be particularly useful for generating the antibody molecules of the present invention.

Generally, the host cell may be a prokaryotic or eukaryotic cell, comprising the nucleic acid molecule or the vector or a cell derived from such a cell and containing the nucleic acid molecule or the vector of the invention. In a preferred embodiment, the host cell comprises, i.e. is genetically modified with, the nucleic acid molecule or the vector in such a way that it contains the nucleic acid molecule integrated into the genome. For example, such host cell, but also the host cell in general, may be a bacterial, yeast, a fungus or a eukaryotic cell.

The host cell is capable to express or expresses an antibody molecule/binding molecule (or a fragment or a derivative thereof) as defined and provided herein. An overview of examples of different corresponding expression systems to be used for generating the host cell, for example this particular one, is for instance contained in Methods in Enzymology 153 (1987), 385-516, in Bitter et al. (Methods in Enzymology 153 (1987), 516-544), in Sawers et al. (Applied Microbiology and Biotechnology 46 (1996), 1-9), Billman-Jacobe (Current Opinion in Biotechnology 7 (1996), 500-4), Hockney (Trends in Biotechnology 12 (1994), 456-463), Griffiths et al., (Methods in Molecular Biology 75 (1997), 427-440), Coloma et al. (1992) J. Imm. Methods 152: 89-104, Gurtu et al. (1996) Biochem. Biophys. Res. Comm. 229: 295-298.

The transformation or genetically engineering of the host cell with a nucleic acid molecule/binding molecules or vector can be carried out by standard methods, as for instance described in Sambrook and Russell (2001), Molecular Cloning: A Laboratory Manual, CSH Press, Cold Spring Harbor, N.Y., USA; Methods in Yeast Genetics, A Laboratory Course Manual, Cold Spring Harbor Laboratory Press, 1990.

As mentioned above and as further described and exemplified herein, the antibody molecules, polynucleotides, vectors, host cells and/or compositions as described and provided in the present invention may be useful for diagnostic purposes, e.g., for diagnosing a disease associated with amyloidogenesis and/or amyloid-plaque formation. Accordingly, the present invention relates to an antibody molecule, a polynucleotide, a vector, a host cell and/or a composition as described and provided in the present invention for use in diagnosis of a disease associated with amyloidogenesis and/or amyloid-plaque formation. Examples for a disease associated with amyloidogenesis and/or amyloid-plaque formation in context of the present invention are Alzheimer disease, e.g., sporadic Alzheimer disease or familial Alzheimer disease, cerebral amyloid angiopathy, dementia, motor neuropathy, Down's syndrome, Creutzfeld Jacob disease and other disorders, like transmissible spongiform encephalopathies (Gerstmann-Strä ussler-Scheinker syndrome, fatal familial insomnia and kuru, hereditary cerebral hemorrhage with amyloidosis Dutch type, Parkinson's disease, HIV-related dementia, Lewy body disease, mixed dementias, head trauma, familial Danish Dementia, familial British Dementia and neuronal disorders related to aging. Accordingly, for example, the present invention relates to an antibody molecule (or a derivative or a fragment thereof) as described and provided herein or a composition as described and provided herein, for use in diagnosing sporadic Alzheimer disease, familial Alzheimer disease, cerebral amyloid angiopathy, dementia, motor neuropathy, Down's syndrome, Creutzfeld Jacob disease and other Prion disorders, hereditary cerebral hemorrhage with amyloidosis Dutch type, Parkinson's disease, HIV-related dementia, Lewy body disease, mixed dementias, head trauma, familial Danish Dementia, familial British Dementia and/or neuronal disorders related to aging. The means and methods provided herein, in particular the antibody molecules (and their derivatives and/or fragments), can also be employed in diagnosis or in therapy of other related disorders, like, e.g. mixed dementias etc.

The present invention relates to an antibody (or fragments or derivatives thereof) as described and provided herein or a composition as described and provided herein for use in the diagnosis of a disease associated with amyloidogenesis and/or amyloid-plaque formation in a patient or for use in the diagnosis of the susceptibility of a patient for the development of a disease associated with amyloidogenesis and/or amyloid-plaque formation. Again, non-limiting examples for a disease associated with amyloidogenesis and/or amyloid-plaque formation in context of the present invention are Alzheimer disease, e.g., sporadic Alzheimer disease or familial Alzheimer disease, cerebral amyloid angiopathy, dementia, motor neuropathy, Down's syndrome, Creutzfeld Jacob disease and other transmissible spongiform encephalopathies (Gerstmann-Strä ussler-Scheinker syndrome, fatal familial insomnia and kuru), hereditary cerebral hemorrhage with amyloidosis Dutch type, Parkinson's disease, HIV-related dementia, Lewy body disease, mixed dementias, head trauma, familial Danish Dementia, familial British Dementia and neuronal disorders related to aging. Accordingly, for example, the present invention relates to an antibody molecule as described and provided herein or a composition as described and provided herein, for use in diagnosing the susceptibility of a patient for the development of sporadic Alzheimer disease, familial Alzheimer disease, cerebral amyloid angiopathy, dementia, motor neuropathy, Down's syndrome, Creutzfeld Jacob disease and other Prion disorders, hereditary cerebral hemorrhage with amyloidosis Dutch type, Parkinson's disease, HIV-related dementia, Lewy body disease, mixed dementias, head trauma, familial Danish Dementia, familial British Dementia and/or neuronal disorders related to aging of a patient. As another example, the present invention relates to an antibody molecule (or fragments or derivatives thereof) as described and provided herein or a composition as described and provided herein, for use in diagnosing sporadic Alzheimer disease, familial Alzheimer disease, cerebral amyloid angiopathy, dementia, motor neuropathy, Down's syndrome, Creutzfeld Jacob disease and other Prion disorders, hereditary cerebral hemorrhage with amyloidosis Dutch type, Parkinson's disease, HIV-related dementia, Lewy body disease, mixed dementias, head trauma, familial Danish Dementia, British Dementia and/or neuronal disorders related to aging in a patient. Again, also other disorders and diseases can be treated and or diagnosed with the means and methods of this invention.

As mentioned above, the present invention relates to methods of diagnosing a subject or patient suspected of suffering from a disease associated with amyloidogenesis and/or amyloid-plaque formation, comprising the steps of (a) determining in a biological sample obtained from said subject/patient the amount of Aβ oligomers; and (b) comparing the amount of Aβ oligomers determined in (a) with a reference amount of Aβ oligomers determined in (a biological sample from) a control subject or patient (healthy subject), wherein said disease is diagnosed when said amount determined in (a) differs from said reference amount. Preferably, said Aβ oligomer is an oligomer of AβpE3. In context of the present invention, non-limiting examples for such biological samples are a cell sample, a tissue sample, a cerebrospinal fluid sample, or a blood sample. All samples may be in vitro samples. The tissue sample may be a brain sample. The blood sample may be a serum sample. Also envisaged is a sample of the cerebral fluid (liquor etc.). In context with the present invention, non-limiting examples for a disease associated with amyloidogenesis and/or amyloid-plaque formation are Alzheimer disease, e.g., sporadic Alzheimer disease or familial Alzheimer disease, cerebral amyloid angiopathy, dementia, motor neuropathy, Down's syndrome, Creutzfeld Jacob disease and other Prion disorders, hereditary cerebral hemorrhage with amyloidosis Dutch type, Parkinson's disease, HIV-related dementia, Lewy body disease, mixed dementias, head trauma, familial Danish Dementia, British Dementia and neuronal disorders related to aging.

The present invention relates to a method of diagnosing a subject or patient suspected of suffering from familial Alzheimer disease, comprising the steps of (a) determining in a serum sample obtained from said subject/patient the amount of Aβ oligomers; and (b) comparing the amount of Aβ oligomers determined in (a) with a reference amount of Aβ oligomers determined in a serum sample from a control subject or patient (healthy subject), wherein said disease is diagnosed when said amount determined in (a) differs from said reference amount. Preferably, said Aβ oligomer is an oligomer of AβpE3.

The present invention relates to a method of diagnosing a subject or patient suspected of suffering from sporadic Alzheimer disease, comprising the steps of (a) determining in a serum sample obtained from said subject/patient the amount of Aβ oligomers; and (b) comparing the amount of Aβ oligomers determined in (a) with a reference amount of Aβ oligomers determined in a serum sample from a control subject or patient (healthy subject), wherein said disease is diagnosed when said amount determined in (a) differs from said reference amount. Preferably, said Aβ oligomer is an oligomer of AβpE3. The present invention relates to a method of diagnosing a subject or patient suspected of suffering from familial Alzheimer disease, comprising the steps of (a) determining in a brain sample obtained from said subject/patient the amount of Aβ oligomers; and (b) comparing the amount of Aβ oligomers determined in (a) with a reference amount of Aβ oligomers determined in a brain sample from a control subject or patient (healthy subject), wherein said disease is diagnosed when said amount determined in (a) differs from said reference amount. The present invention relates to a method of diagnosing a subject or patient suspected of suffering from sporadic Alzheimer disease, comprising the steps of (a) determining in a brain sample obtained from said subject/patient the amount of Aβ oligomers; and (b) comparing the amount of Aβ oligomers determined in (a) with a reference amount of Aβ oligomers determined in a brain sample from a control subject or patient (healthy subject), wherein said disease is diagnosed when said amount determined in (a) differs from said reference amount.

Generally, in context of the present invention, all samples may be in vitro samples. However, it is also envisaged that the antibodies of this invention (or fragments thereof or derivatives thereof, like labeled molecules) are used in in vivo methods, like in molecular imaging methods and in, e.g., diagnostic or scientific scans. As already mentioned, the present invention relates to methods of monitoring the efficacy of a treatment of a disease associated with amyloidogenesis and/or amyloid-plaque formation characterized by the presence of Aβ oligomers in a subject or patient suffering from said disease or being prone to suffering from said disease comprising the steps (a) determining in a biological sample obtained from said subject or patient the amount of Aβ oligomers; and (b) comparing the amount of Aβ oligomers determined in (a) with a reference amount of Aβ oligomers determined in (a biological sample from) a control subject or patient (healthy subject), wherein the extent of the difference between said amount determined in (a) and said reference amount is indicative for said efficacy of a treatment of said disease. In context of the present invention, non-limiting examples for such (biological) samples are a cell sample, a tissue sample, a cerebral sample (like liquor), a cerebrospinal fluid sample, or a blood sample. All samples may be in vitro samples. The tissue sample may be a brain sample. The blood sample may be a serum sample. In context with the present invention, examples for a disease associated with amyloidogenesis and/or amyloid-plaque formation in context of the present invention are Alzheimer disease, e.g., sporadic Alzheimer disease or familial Alzheimer disease, cerebral amyloid angiopathy, dementia, motor neuropathy, Down's syndrome, Creutzfeld Jacob disease and other Prion disorders, hereditary cerebral hemorrhage with amyloidosis Dutch type, Parkinson's disease, HIV-related dementia, Lewy body disease, mixed dementias, head trauma, familial Danish Dementia, British Dementia and neuronal disorders related to aging.

Accordingly, the present invention relates to methods of monitoring the efficacy of a treatment of sporadic Alzheimer disease characterized by the presence of Aβ oligomers in a subject or patient suffering from said disease or being prone to suffering from said disease comprising the steps (a) determining in a brain sample obtained from said subject or patient the amount of Aβ oligomers; and (b) comparing the amount of Aβ oligomers determined in (a) with a reference amount of Aβ oligomers determined in a brain sample from a control subject or patient (healthy subject), wherein the extent of the difference between said amount determined in (a) and said reference amount is indicative for said efficacy of a treatment of said disease. Preferably, said Aβ oligomer is an oligomer of AβpE3.

The present invention also relates to methods of monitoring the efficacy of a treatment of familial Alzheimer disease characterized by the presence of Aβ oligomers in a subject or patient suffering from said disease or being prone to suffering from said disease comprising the steps (a) determining in a brain sample obtained from said subject or patient the amount of Aβ oligomers; and (b) comparing the amount of Aβ oligomers determined in (a) with a reference amount of Aβ oligomers determined in a brain sample from a control subject or patient (healthy subject), wherein the extent of the difference between said amount determined in (a) and said reference amount is indicative for said efficacy of a treatment of said disease. Preferably, said Aβ oligomer is an oligomer of AβpE3.

The present invention furthermore relates to methods of monitoring the efficacy of a treatment of sporadic Alzheimer disease characterized by the presence of Aβ oligomers in a subject or patient suffering from said disease or being prone to suffering from said disease comprising the steps (a) determining in a serum sample obtained from said subject or patient the amount of Aβ oligomers; and (b) comparing the amount of Aβ oligomers determined in (a) with a reference amount of Aβ oligomers determined in a serum sample from a control subject or patient (healthy subject), wherein the extent of the difference between said amount determined in (a) and said reference amount is indicative for said efficacy of a treatment of said disease. Preferably, said Aβ oligomer is an oligomer of AβpE3. The present invention in addition relates to methods of monitoring the efficacy of a treatment of familial Alzheimer disease characterized by the presence of Aβ oligomers in a subject or patient suffering from said disease or being prone to suffering from said disease comprising the steps (a) determining in a serum sample obtained from said subject or patient the amount of Aβ oligomers; and (b) comparing the amount of Aβ oligomers determined in (a) with a reference amount of Aβ oligomers determined in a serum sample from a control subject or patient (healthy subject), wherein the extent of the difference between said amount determined in (a) and said reference amount is indicative for said efficacy of a treatment of said disease. Preferably, said Aβ oligomer is an oligomer of AβpE3.

As already mentioned, the present invention relates to methods of predicting the efficacy of a treatment of a disease associated with amyloidogenesis and/or amyloid-plaque formation for a subject or patient suffering from said disease or being prone to suffering from said disease comprising the steps (a) determining in biological sample obtained from said subject or patient the amount of Aβ oligomers; and (b) comparing the amount of Aβ oligomers determined in (a) with a reference amount of Aβ oligomers determined in (a biological sample from) a control subject or patient, wherein the extent of the difference between said amount of Aβ oligomers determined in (a) and said reference amount of Aβ oligomers is indicative for the predicted efficacy of a treatment of said disease. Preferably, said Aβ oligomer is an oligomer of AβpE3. In context of the present invention, non-limiting examples for such biological samples are a cell sample, a tissue sample, a cerebrospinal fluid sample, or a blood sample. All samples may be in vitro samples. The tissue sample may be a brain sample. The blood sample may be a serum sample. In context with the present invention, examples for a disease associated with amyloidogenesis and/or amyloid-plaque formation are Alzheimer disease, e.g., sporadic Alzheimer disease or familial Alzheimer disease, cerebral amyloid angiopathy, dementia, motor neuropathy, Down's syndrome, Creutzfeld Jacob disease and other Prion disorders, hereditary cerebral hemorrhage with amyloidosis Dutch type, Parkinson's disease, HIV-related dementia, Lewy body disease, mixed dementias, head trauma, familial Danish Dementia, British Dementia and neuronal disorders related to aging.

Accordingly, the present invention relates to methods of predicting the efficacy of a treatment of sporadic Alzheimer disease for a subject or patient suffering from said disease or being prone to suffering from said disease comprising the steps (a) determining in a brain sample obtained from said subject or patient the amount of Aβ oligomers; and (b) comparing the amount of Aβ oligomers determined in (a) with a reference amount of Aβ oligomers determined in a brain sample obtained from a control subject or patient, wherein the extent of the difference between said amount of Aβ oligomers determined in (a) and said reference amount of Aβ oligomers is indicative for the predicted efficacy of a treatment of said disease. Preferably, said Aβ oligomer is an oligomer of AβpE3. The present invention relates to methods of predicting the efficacy of a treatment of familial Alzheimer disease for a subject or patient suffering from said disease or being prone to suffering from said disease comprising the steps (a) determining in a brain sample obtained from said subject or patient the amount of Aβ oligomers; and (b) comparing the amount of Aβ oligomers determined in (a) with a reference amount of Aβ oligomers determined in a brain sample obtained from a control subject or patient, wherein the extent of the difference between said amount of Aβ oligomers determined in (a) and said reference amount of Aβ oligomers is indicative for the predicted efficacy of a treatment of said disease. Preferably, said Aβ oligomer is an oligomer of AβpE3. The present invention relates to methods of predicting the efficacy of a treatment of sporadic Alzheimer disease for a subject or patient suffering from said disease or being prone to suffering from said disease comprising the steps (a) determining in a serum sample obtained from said subject or patient the amount of Aβ oligomers; and (b) comparing the amount of Aβ oligomers determined in (a) with a reference amount of Aβ oligomers determined in a serum sample obtained from a control subject or patient, wherein the extent of the difference between said amount of Aβ oligomers determined in (a) and said reference amount of Aβ oligomers is indicative for the predicted efficacy of a treatment of said disease. Preferably, said Aβ oligomer is an oligomer of AβpE3. The present invention relates to methods of predicting the efficacy of a treatment of familial Alzheimer disease for a subject or patient suffering from said disease or being prone to suffering from said disease comprising the steps (a) determining in a serum sample obtained from said subject or patient the amount of Aβ oligomers; and (b) comparing the amount of Aβ oligomers determined in (a) with a reference amount of Aβ oligomers determined in a serum sample obtained from a control subject or patient, wherein the extent of the difference between said amount of Aβ oligomers determined in (a) and said reference amount of Aβ oligomers is indicative for the predicted efficacy of a treatment of said disease. Preferably, said Aβ oligomer is an oligomer of AβpE3.

In context of the methods provided herein above, the terms "subject" and "sample" and also the terms "reference" and "control samples" are used and defined. The following other additional explanations are provided in context of the herein described means and methods:

The sample may be used without the involvement of any processing step or may also include the possibility that the sample is subjected to one or more processing steps. Suitable processing steps depend on the type of sample used and application, and are, in each case, well known to a person skilled in the art.

It is understood that, after validation, like official validation by health authorities and the like of the developed methodology for the claimed diagnosis and/or prognosis and/or monitoring the efficacy of a treatment and/or predicting the efficacy of a treatment of a disease associated with amyloidogenesis and/or amyloid-plaque formation, a standard guide value could be defined, which might replace the described reference amounts.

The "reference amount" as used herein can and may refer to a control amount of Abeta oligomers (in particular AβpE3 oligomers), with which the amount of Abeta oligomers (or in particular AβpE3 oligomers) in the sample to be tested determined in a method of diagnosis and/or prognosis and/or monitoring the efficacy of a treatment and/or predicting the efficacy of a treatment of a disease associated with amyloidogenesis and/or amyloid-plaque formation according to the invention is compared. The reference amount is for example, determined using a sample derived from a corresponding sample of a healthy subject or of a subject having/suffering a disease associated with amyloidogenesis and/or amyloid-plaque formation characterized by the presence of Abeta oligomers. The reference amount may also be determined using a sample of the same subject that has been obtained at an earlier point in time, particularly at a point in time at which the subject was not affected by a disease associated with amyloidogenesis and/or amyloid-plaque formation as determined by any suitable method according to the prior art, or at a point in time in which the sample of the subject has first or previously, respectively, been examined.

According to the embodiments of the invention and methods provided herein, the amount of the Abeta oligomers, in a sample is compared to the reference amount, wherein (i) in a method of diagnosis the amount of the Abeta oligomers in a sample is significantly altered compared to the reference amount; ii) in a method of prognosis the amount of the Abeta oligomers in a sample is significantly altered compared to the reference amount; iii) in a method of monitoring the efficacy of a treatment the amount of the Abeta oligomers in a sample is significantly increased or decreased compared to the reference amount; iv) in a method of predicting the efficacy of a treatment the amount of the Abeta oligomers in a sample is significantly altered compared to the reference amount. Again, the Aβ/Abeta oligomer(s) to be assessed is (are) in particular an AβpE3 oligomer(s).

The present invention also relates to a kit comprising an antibody molecule/binding molecule as described and provided herein or as prepared by the method as described and provided herein, a composition as described and provided herein, a nucleic acid molecule as described and provided herein, a vector as described and provided herein and/or a host cell as described and provided herein.

The present invention also relates to and provides for the following sequences:

```
Antibody sequences:
9D5 heavy chain CDRs:
CDR1 DNA:
                                          SEQ ID NO: 1.)
GGCTACACATTCAGTAGCTACTGGATAGAG

CDR1 AA:
                                          SEQ ID NO: 2.)
GYTFSSYWIE

CDR2 DNA:
                                          SEQ ID NO: 3.)
GAGATTTTACCTGGACGTGGTAGTACTCACTACAATGAGAAGTTCAAGGGC

CDR2 AA:
                                          SEQ ID NO: 4.)
EILPGRGSTHYNEKFKG

CDR3 DNA:
                                          SEQ ID NO: 5.)
```

TCCCCTATTACTACCTCTGACTAC

CDR3 AA:
SEQ ID NO: 6.)
SPITTSDY

9D5 light chain CDRs:
CDR1 DNA:
SEQ ID NO: 7.)
AGATCTAGTCAGAGCCTTCTCCACAGTAATGGAAACACCTATTTACAT

CDR1 AA:
SEQ ID NO: 8.)
RSSQSLLHSNGNTYLH

CDR2 DNA:
SEQ ID NO: 9.)
AAAGTTTCCAACCGATTTTCT

CDR2 AA:
SEQ ID NO: 10.)
KVSNRFS

CDR3 DNA:
SEQ ID NO: 11.)
TCTCAAAGTACACATGTTCCGCTCACG

CDR3 AA:
SEQ ID NO: 12.)
SQSTHVPLT

9D5 $V_H$:
DNA:
SEQ ID NO: 25
CAGCTGCAGCAGTCTGGAGCTGAGCTGATGAAGCCTGGGGCCTCAGTG

AAGATATCCTGCAAGGCTACTGGCTACACATTCAGTAGCTACTGGATA

GAGTGGGTAAAGCAGAGGCCTGGACATGGCCTTGAGTGGATTGGAGAG

ATTTTACCTGGACGTGGTAGTACTCACTACAATGAGAAGTTCAAGGGC

AAGGCCACATTCACTGCAGATACATCCTCCAACACAGCCTACATGCAA

CTCAGCAGCCTGACATCTGAGGACTCTGCCGTCTATTACTGTGCAAGA

TCCCCTATTACTACCTCTGACTACTGGGGCCAAGGCACCACTCTCACA

GTCTCCTCA

AA:
SEQ ID NO: 26
QLQQSGAELMKPGASVKISCKATGYTFSSYWIEWVKQRPGHGLEWIGE

ILPGRGSTHYNEKFKGKATFTADTSSNTAYMQLSSLTSEDSAVYYCAR

SPITTSDYWGQGTTLTVSS

9D5 $V_L$:
DNA:
SEQ ID NO: 27
GATGTTGTGATGACCCAAACTCCACTCTCCCTGCCTGTCAGTCTTGGA

GATCAAGCCTCCATCTCTTGCAGATCTAGTCAGAGCCTTCTCCACAGT

AATGGAAACACCTATTTACATTGGTACCTGCAGAAGCCAGGCCAGTCT

CCAAAGCTCCTGATCTACAAAGTTTCCAACCGATTTTCTGGGGTCCCA

GACAGGTTCAGTGGCAGTGGATCAGGGACAGATTTCACACTCAAGATC

AGCAGAGTGGAGGCTGAGGATCTGGGAGTTTATTTCTGCTCTCAAAGT

ACACATGTTCCGCTCACGTTCGGTGCTGGGACC

AA:
SEQ ID NO: 28
DVVMTQTPLSLPVSLGDQASISCRSSQSLLHSNGNTYLHWYLQKPGQSP

KLLIYKVSNRFSGVPDRFSGSGSGTDFTLKISRVEAEDLGVYFCSQSTH

VPLTFGAGT

8C4 heavy chain CDRs:
CDR1 DNA:
SEQ ID NO: 13.)
GGGTACACATTCAGAAGCTATTGGATAGAG

CDR1 AA:
SEQ ID NO: 14.)
GYTFRSYWIE

CDR2 DNA:
SEQ ID NO: 15.)
GAGATTTTACCTGGAAGAGGTAGTACTAAGTACAATGAGAAGTTCAAGGGC

CDR2 AA:
SEQ ID NO: 16.)
EILPGRGSTKYNEKFKG

CDR3 DNA:
SEQ ID NO: 17.)
TCCCCTATTACTACCTCTGACTAC

CDR3 AA:
SEQ ID NO: 18.)
SPITTSDY

8C4 light chain CDRs:
CDR1 DNA:
SEQ ID NO: 19.)
AGATCTAGTCAGAGCCTTGTACACAGTAATGGAAACACCTATTTACAT

CDR1 AA:
SEQ ID NO: 20.)
RSSQSLVHSNGNTYLH

CDR2 DNA:
SEQ ID NO: 21)
AAAGTTTCCAACCGATTTTCT

CDR2 AA:
SEQ ID NO: 22.)
KVSNRFS

CDR3 DNA:
SEQ ID NO: 23.)
TCTCAAAGTACACATGTTCCGCTCACG

CDR3 AA:
SEQ ID NO: 24.)
SQSTHVPLT

8C4 $V_H$:
DNA:
SEQ ID NO: 29
GCTGAGCTGAAGAAGCCTGGGGCCTCAGTGAAGATATCCTGCAAGGCT

ACTGGGTACACATTCAGAAGCTATTGGATAGAGTGGGTAAAGCAGAGG

CCTGGACATGGCCTTGAGTGGATAGGAGAGATTTTACCTGGAAGAGGT

AGTACTAAGTACAATGAGAAGTTCAAGGGCAAGGCCACATTCACTGCA

GATACATCCTCCAACACAGCCAACATGCAACTCAGCAGCCTGACATCT

GAGGACTCTGCCGTCTATTACTGTGCAAGATCCCCTATTACTACCTCT

GACTAC

AA:
SEQ ID NO: 30
AELKKPGASVKISCKATGYTFRSYWIEWVKQRPGHGLEWIGEILPGRG

STKYNEKFKGKATFTADTSSNTANMQLSSLTSEDSAVYYCARSPITTS

DY

-continued

8C4 V$_L$:
DNA:

SEQ ID NO: 31:
TCTTGCAGATCTAGTCAGAGCCTTGTACACAGTAATGGAAACACCTAT

TTACATTGGTACCTGCAGAAGCCAGGCCAGTCTCCAAAGCTCCTGATC

TACAAAGTTTCCAACCGATTTTCTGGGGTCCCAGACAGGTTCAGTGGC

AGTGGATCAGGGACAGATTTCACACTCAAGATCAGCAGAGTGGAGGCT

GAGGATCTGGGAGTTTATTTCTGCTCTCAAAGTACACATGTTCCGCTC

ACGTTCGGTGCTGGGACC

AA:

SEQ ID NO: 32:
SCRSSQSLVHSNGNTYLHWYLQKPGQSPKLLIYKVSNRFSGVPDRFSG

SGSGTDFTLKISRVEAEDLGVYFCSQSTHVPLTFGAGT

In the following, the present invention is illustrated by figures and examples which are not intended to limit the scope of the present invention.

b Hippocampus Therapeutic effect of 9D5 passive immunization in 5XFAD mice (hippocampus). Sections were stained against total Aβ (4G8), $Aβ_{X-40}$ (G210), $Aβ_{X-42}$ (G211), AβpE3 (2-48) (see also FIG. 14). A First cohort of immunized mice. Plaque-load quantification showed a significant decrease for total Aβ (4G8), pyroglutamate-modified Aβ (2-48), Aβ40 (G2-10), and Aβ42 (G2-11) in 9D5-injected mice compared to PBS-injected mice. B Second cohort of immunized mice. Immunization with 9D5 proved to reduce plaque load in the cortex of 6-month old 5XFAD mice when compared to age-matched controls. *P<0.05; **P<0.01.

Figure 16:
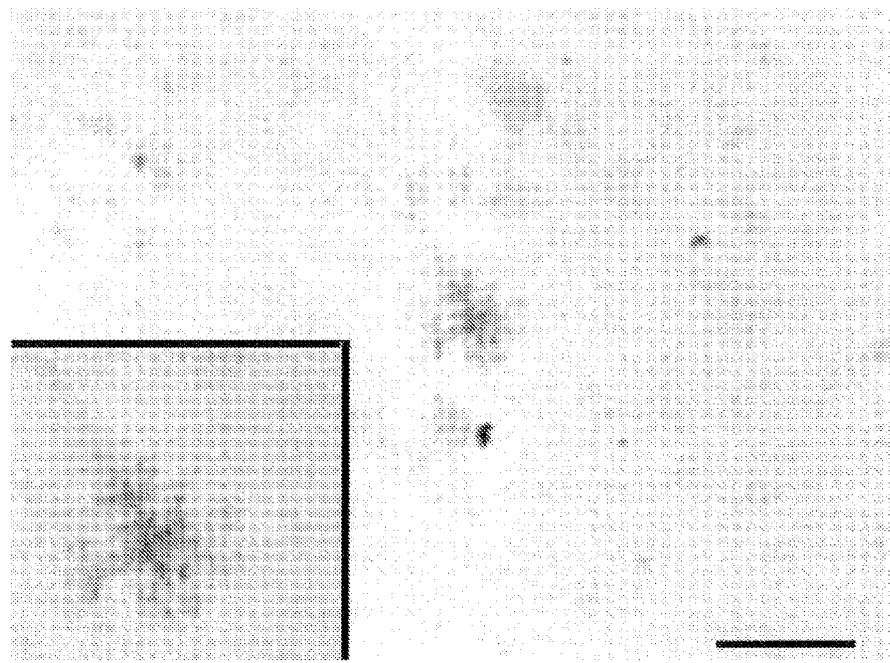

FIG. 16: Microglia cell in Alzheimer brain visualized with 9D5 immunostaining. This observation indicates that low molecular weight AβpE3 oligomers can in principle be phagocytosed by microglia in mouse and man.

Figure 17:
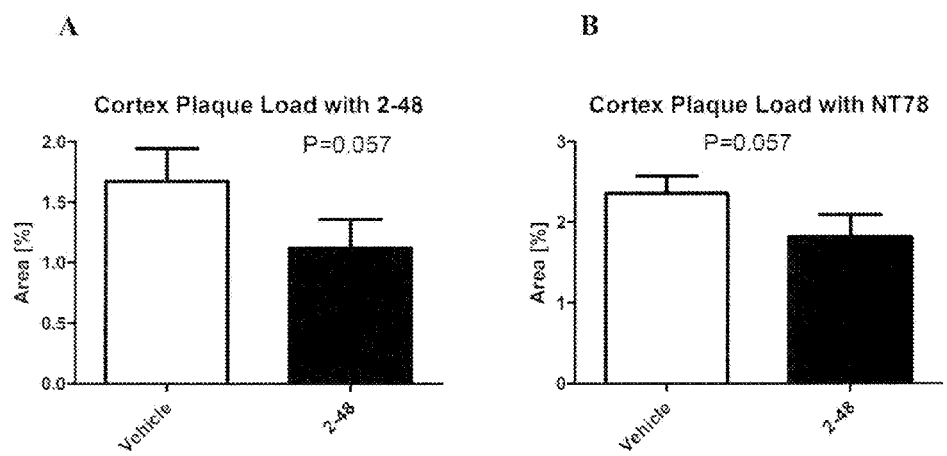

FIG. 17: Passive immunization with N-terminal specific monoclonal antibody 2-48. Passive immunization with a weekly injection of 2-48 antibody revealed a trend in plaque load reduction. Both, staining with the generic Aβ antibody NT78 and AβpE3-specific antibody 2-48 showed a trend in reduced plaque load in cortex of immunized mice.

EXAMPLES

Example 1

Antibodies and Peptides

The AβpE3 oligomere specific antibodies 9D5H6 (IgG2b) and 8C4D2 (IgG1) were generated by immunizing three Balb/c mice with AβpE3-38. After preparation of the lymph nodes cells were fused with the myeloma cell line P3-X63-Ag8. The hybridoma supernatants of mixed clones were screened by ELISA and subcloned. The monoclonal antibodies 9D5 and 8C4 were selected by ELISA against different N-terminal Aβ epitopes. Clones producing signals with AβpE3-38 and AβpE3-42, but no signal with AβpE1-42 were isolated and further characterized. For comparison, Aβ antibodies 4G8 (Aβ epitope 17-24; Covance), W0-2 (Aβ epitope 4-8; The Genetics Company), NT78 (against generic Aβ1-16, Synaptic Systems) and 2-48 (against N-terminal AβpE3, Synaptic Systems; Wirths, O., et al. *J Neural Transm* 117, 85-96 (2010)) were used. GFAP (rabbit) and IBA1 (rabbit) antisera were from Synaptic Systems and Wako Pure Chemicals respectively. Peptides were purchased from PSL (Heidelberg, Germany), reconstituted as indicated below and immediately frozen until further use.

Example 2

Western Blot

For each Western blot, 10 ng of peptide was loaded per lane of a 12% Bis-Tris gel in MES buffer and run at 150 volts for 1 h. The peptides were then transferred to 0.45 μm nitrocellulose for 1 h at 100 mA per membrane using wet transfer in Towbin buffer. Post transfer, membranes were incubated in PBS, pH 9.0 at 95° C. for 5 min, which allows for improved access to the antigen. Membranes were then blocked in 2% NFDM/PBS, pH 9.0 for 1 h at room temperature while gently mixing, before overnight incubation at 4° C. using the primary antibodies W0-2 (1 μg/ml); 9D5H6 (10 μg/ml) and 2-48 (10 μg/ml) in blocking buffer. Membranes were rinsed in PBS/0.05% Tween-20 (pH 9.0) three times for 5 min. Secondary anti-mouse IgG-HRP was applied in blocking conditions at a 1:10,000 dilution for 1 h at room temperature. Membranes were rinsed in PBS/0.05% Tween-20 (pH 9.0) three times for 10 min. The blots were developed using ECL Advance (GE Healthcare) by applying the chemiluminescent reagents for 1 min in reduced light conditions and then imaged on standard film emulsion.

Example 3

Statistical Analysis

All statistical analysis was performed using unpaired t-test with GraphPad Prism version 4.03 for Windows (GraphPad Software, San Diego, Calif., USA). Data were presented as mean±s.e.m.

Example 4

Immunohistochemistry on Paraffin Sections

Human brain samples were obtained from the Netherlands Brain Bank (NBB). Human tissue was post-fixed in 4% buffered formalin at 4° C. for several weeks. Mice were transcardially perfused with 4% PFA in PBS and brains were carefully dissected. Post fixation was carried out in 4% buffered formalin at 4° C. before the tissue was embedded in paraffin. Immunohistochemistry was performed on 4 µm sagital paraffin sections, as described previously (Wirths, O., et al. *J Neural Transm* 117, 85-96 (2010)). In brief, sections were deparaffinized in xylene and rehydrated in a series of ethanol. After treatment with 0.3% $H_2O_2$ in PBS to block endogenous peroxidases, antigen retrieval was achieved by boiling sections in 0.01 M citrate buffer pH 6.0, followed by 3 min incubation in 88% formic acid. Non-specific binding sites were blocked by treatment with skim milk and fetal calf serum in PBS, prior to the addition of the primary antibodies. Primary antibodies 4G8 (1 µg/ml), 9D5H6 (10 µg/ml), 8C4 (cell supernatant) and 2-48 (10 µg/ml) were incubated overnight in a humid chamber at room temperature, followed by incubation with biotinylated secondary antibodies (DAKO, Glostrup, DK) before staining was visualized using the ABC method with Vectastain kit (Vector Laboratories, Burlingame, USA) and diaminobenzidine as chromogen providing a reddish brown color. Counterstaining was carried out with hematoxylin.

Figure 10:
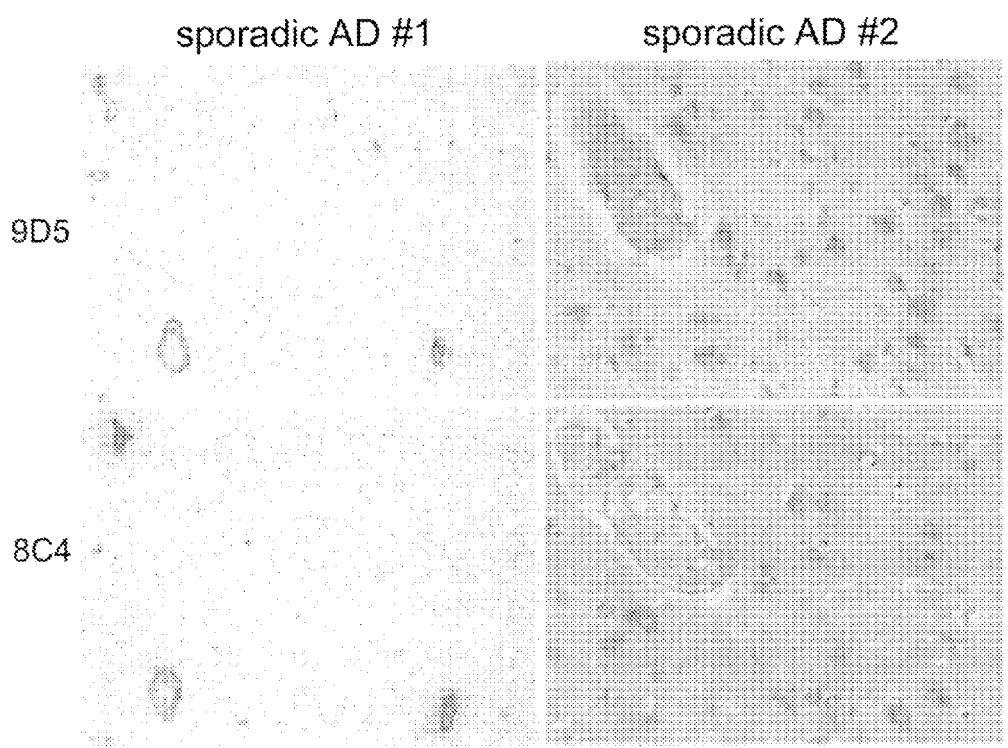
FIG. 10: 9D5 and 8C4 monoclonal antibodies were competing for the same epitope. Parallel sections stained with 9D5 and 8C4 revealed indistinguishable pattern in two cases of sporadic AD showing either prominent blood vessel staining (sporadic case #1) or intraneuronal immunoreactivity (sporadic case #2).

The results for 9D5 and 8C4 are shown in FIG. 10. Human post-mortem brain tissue (frontal cortex) from sporadic AD patients was used to compare the immunohistochemical staining patterns of the monoclonal 9D5 and 8C4 Aβ antibodies. In one of the analyzed cases (#1), a primarily vascular staining pattern was detected, with immunoreactivity in large vessel walls, showing a clear overlap between the two antibodies. Another AD patient (#2) showed a primarily cellular staining pattern, in which strong intraneuronal immunoreactivity but no extracellular plaque pathology could be detected using both antibodies.

Example 5

Dot Blot

Dilutions of each peptide were spotted on a nitrocellulose membrane. After blocking of the membrane by 10% non-fat dry milk TBST solution was applied at 4° C. for one hour. Then, the membrane was washed three times by 1×TBST for 15 minutes. Primary antibodies 4G8 (1 µg/ml), 9D5H6 (10 µg/ml) and 2-48 (10 µg/ml)) were diluted in 5% non-fat dry milk TBST solution and used to cover the membrane with gentle shaking for one hour. After washing the membrane three times by 1×TBST for 15 minutes, secondary antibodies conjugated with horseradish peroxidase were diluted in 5% non-fat dry milk TBST and used to cover the membrane with gentle shaking for one hour. Then the membrane was washed three times by 1×TBST for 15 minutes. Dots were revealed using a chemiluminescence solution, which consisted of 1 ml of BSA (200 ml 0.1 M TRIS-HCL (pH 8.6) and 50 Luminol (Sigma A4685)), 100 µl SB (11 mg para-hydroxycoumaric acid (Sigma C9008) in 10 m DMSO) and 0.3 µl of $H_2O_2$ as substrate. The blots were developed using a Curix60 developing machine (Agfa-Gevaert N.V., Mortsel, Belgium).

Figure 1:
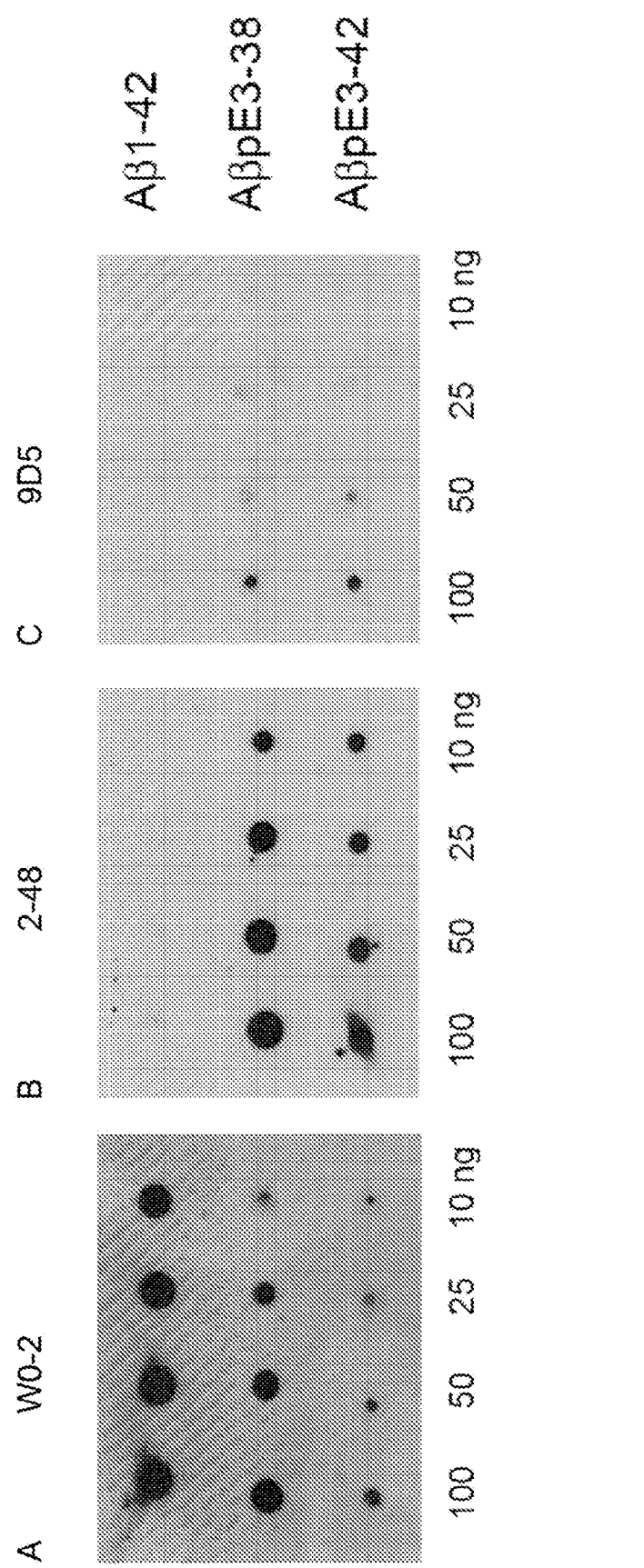
FIG. 1: Antibody 9D5H6/"9D5" recognized AβpE3-42 and Aβ pE3-38, but not Aβ1-42 using Dot blot analysis. Dot blot assay of synthetic Aβ peptides. Peptides were spotted from left to right: 100 ng, 50 ng, 25 ng and 10 ng. (A) W0-2 staining specific for Aβ4-8 recognizing all three peptides. (B) 2-48 (specific for N-terminal AβpE3) and (C) 9D5H6 (1:100) recognized only AβpE3-42 and AβpE3-38.

Dot blot analysis demonstrated that W0-2 (specific for Aβ4-8) recognized all three peptides. 2-48 (specific for N-terminal AβpE3) and 9D5H6/"9D5" recognized AβpE3-42 and AβpE3-38 but not Aβ1-42 (FIG. 1). Although the immunization was carried out with AβpE3-38, the 9D5H6 antibody also reacts with AβpE3-42 indicating that the antibody epitope is shared by both peptides.

Example 6

9D5H6/"9D5" Recognized a Single Oligomeric Form of AβpE3-42 under Reducing Conditions in Western Blot For Western blot analysis of synthetic peptides, 1.5 µg of peptides were loaded on 4-12% vario gels (Anamed), transferred to 0.45 µm nitrocellulose membranes and detected using the primary antibodies W0-2 (1 µg/ml) and 9D5 (10 µg/ml) in blocking buffer. The blots were developed using enhanced chemiluminescence.

Figure 2:
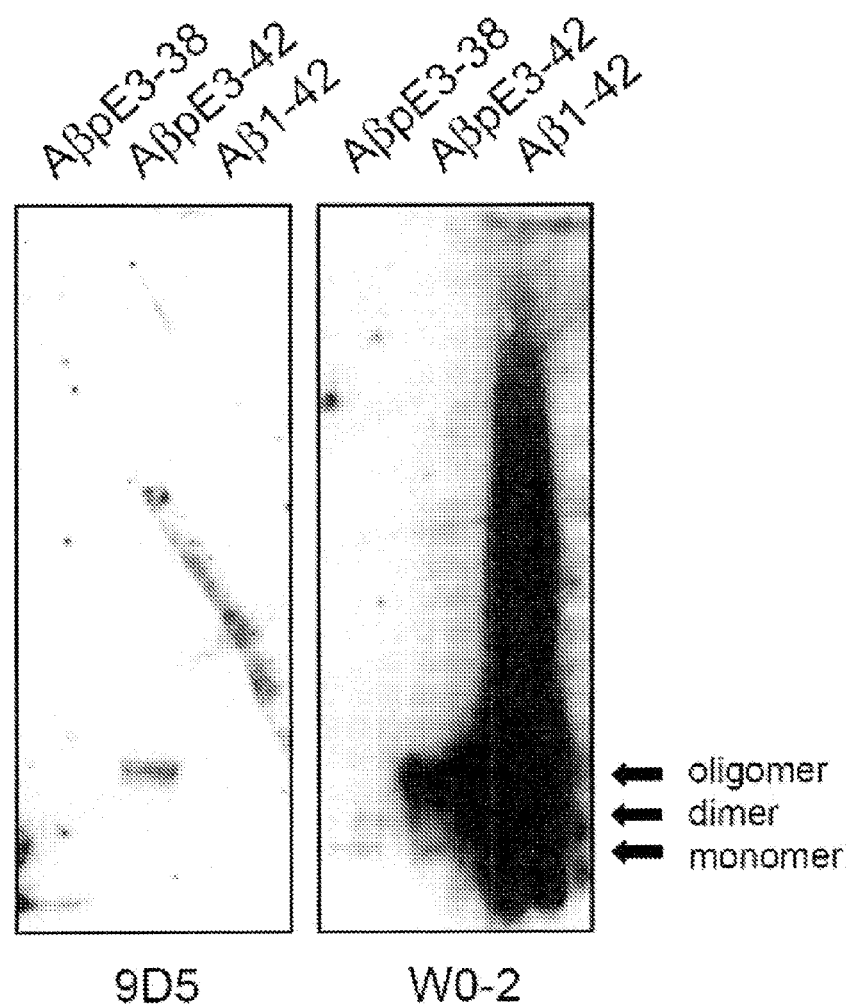
FIG. 2: SDS-Western blot of Aβ peptides. Antibody 9D5H6 recognized a single band of low molecular weight oligomere AβpE3-42 at approximately 10 kDa. No signal was detected with Aβ1-42 or AβpE3-38. Using W0-2 (against Ab 4-8) recognized three bands of AβpE3-42 corresponding to monomeric, dimeric and oligomeric Aβ and two bands of AβpE3-38 corresponding to monomeric and dimeric Aβ. The signal of Aβ1-42 was however much more abundant and demonstrated staining ranging from monomeric to higher molecular weight aggregates. 1.5 μg peptide was applied per lane.

In the presence of SDS and under denaturing conditions, 9D5H6 detected one specific band of AβpE3-42 at approximately 10 kDa without any cross reactivity against Aβ1-42. Under these conditions AβpE3-38 did not form stable oligomers as shown by W0-2 staining. W0-2 detected monomers and dimers of AβpE3-38, monomers, dimers and low molecular weight oligomers of AβpE3-42 and a whole range of aggregation states of Aβ1-42 peptides (FIG. 2).

9D5H6/"9D5" also recognized a single oligomeric form of AβpE3-38 with an estimated size ranging between 10 and 50 kDa under non-reducing conditions in western blot using 4-16% gradient NativePAGE™ NovexR Bis-Tris Gel System von Invitrogen applying the blue native protocol (Schagger and Jagow (1991) Anal. Biochem 199: 223-231).

Example 7

Antibody 9D5H6 Differentiates Between Non-Demented Controls and Alzheimer Disease Patients Human brain samples were obtained from (1) the Netherlands Brain Bank (NBB), Amsterdam, The Netherlands; (2) the APP Swedish and APP arctic FAD brain samples from Upsalla University, and (3) the Presenilin-1 FAD brain samples from the Hopital del la Salpetrière (a generous gift of Prof. Dr. Charles Duyckaerts and Dr. Veronique Sazdovitch) and from Upsalla University. Definite diagnosis was based on established criteria and informed consent was obtained from all subjects.

Figure 3:
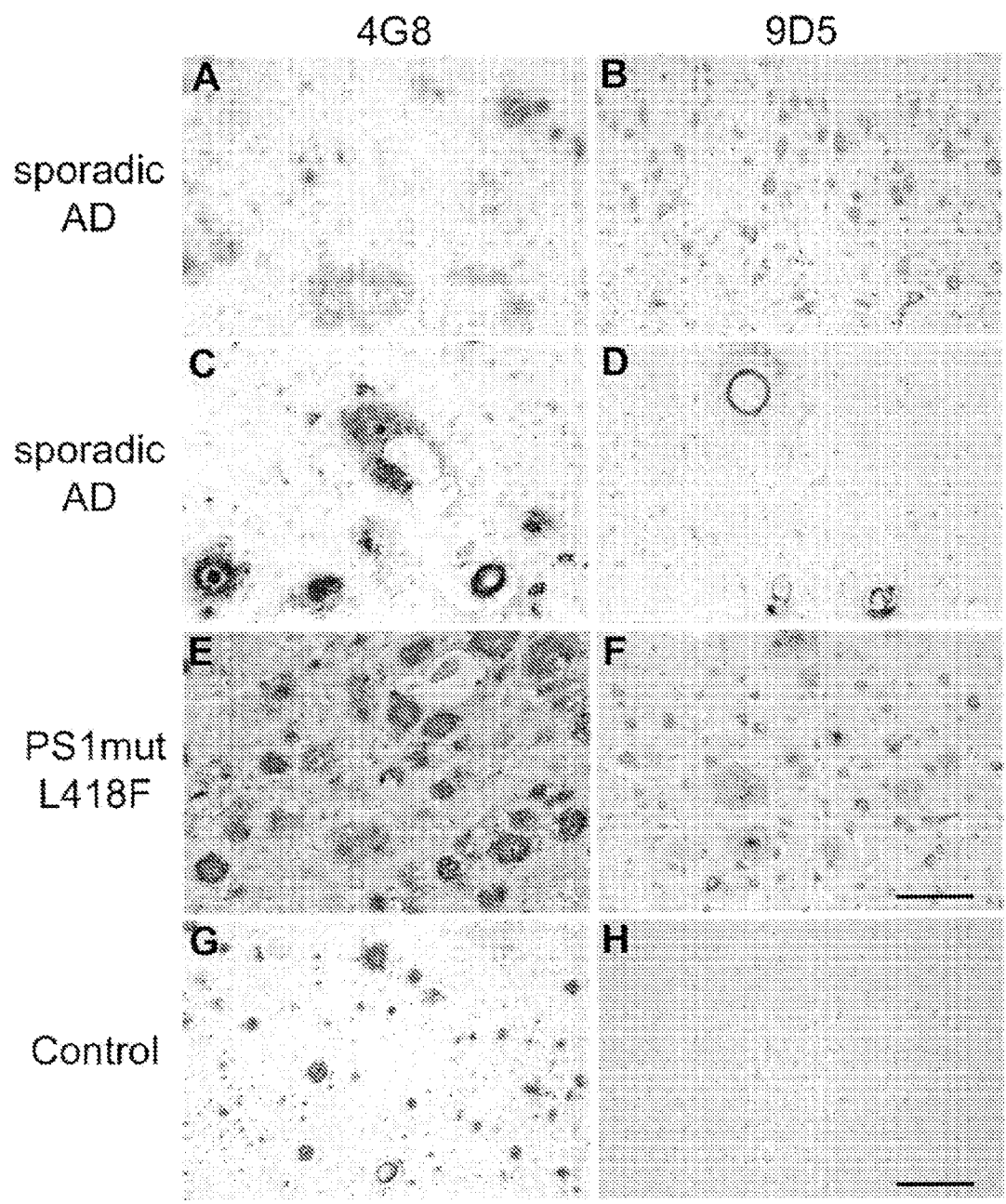
FIG. 3: Staining with the generic Aβ antibody 4G8 detects abundant extracellular plaques in sporadic AD cases (A, C), in a familial AD case harboring the PS1L418F mutation (E), as well as in non-demented controls (G). In addition, vascular Aβ is often detected (C). Staining with antibody 9D5H6 detects either abundant intraneuronal immunoreactivity (B) and/or strong vascular staining (D) in sporadic AD cases, however extracellular plaques are almost absent (B, D). In AD cases harboring the PS1 L418F mutation, a strong intraneuronal and much weaker plaque staining was detected (F). Non-demented control cases were devoid of intraneuronal or extracellular plaque immunoreactivity (H), despite of abundant staining using generic Aβ antibodies (G). Scale bars: A-F: 100 μm, G,H: 200 μm.

Human post-mortem brain tissue (frontal cortex and hippocampus from sporadic AD, FAD and non-demented individuals) was used to compare staining patterns obtained with the 9D5H6 and 4G8 Aβ antibodies (FIG. 3, Table 1). While none of the non-demented controls showed abundant staining with 9D5H6, many plaques were observed using 4G8 in some specimen. This observation demonstrated that plaques in healthy controls do not harbor the 9D5H6 epitope. Most of the sporadic and all of the familial AD (FAD) cases demonstrated high abundance of intraneuronal staining with 9D5H6, but not with 4G8. It is interesting to note that the intraneuronal staining pattern in human cases AD resembled the pattern in 5XFAD mice (FIG. 4). 4G8 (against Aβ17-24) stained Aβ in blood vessels, a typical feature of cerebral amyloid angiopathy (CAA) in healthy controls and AD cases. 9D5H6 staining however was most prominently detected in AD cases. Non-demented control cases exhibited CAA staining with 9D5H6 only weakly. Interestingly, all FAD cases showed also abundant 9D5H6 positive plaques. The FAD cases having an APP Swedish (APP swe) or APP arctic (APP arc) mutation demonstrated a similar extent of Aβ plaque load. The Presenilin-1 case with P264L mutation had only a minor amount of 9D5H6 positive plaques, whereas in the case harboring the PS1Δexon9 mutation only intraneuronal 9D5H6-immunoreactivity was detected (FIG. 5).

Example 8

Antibody 9D5H6 Recognizes a Highly Specific Pattern in 5xFAD Brain

APP/PS1KI (Casas, C., et al. *Am J Pathol* 165, 1289-1300 (2004)) and 5XFAD (Oakley, H., et al. *J. Neurosci.* 26, 10129-10140 (2006)) female bigenic mice have been described previously. The 5xFAD bigenic mice (purchased from Jackson Laboratories, USA) express five FAD mutations three in APP K670N/M671L (770 residue isoform numbering), 1716V and V717I and two in PS1 (M146L and L286V) introduced into APP(695). Both constructs are under the Thy1 promoter. All mice were backcrossed for more than 10 generations on a C57BL/6J genetic background and housed at a 12-h day/12-h night cycle with free access to food and water. All animals were handled according to German guidelines for animal care. All research involving animals have been conducted according to guidelines of the German animal protection law. According to that the local committee for animal welfare at the University Medicine of Göttingen approved the experiments before the mice were sacrificed.

Figure 4:
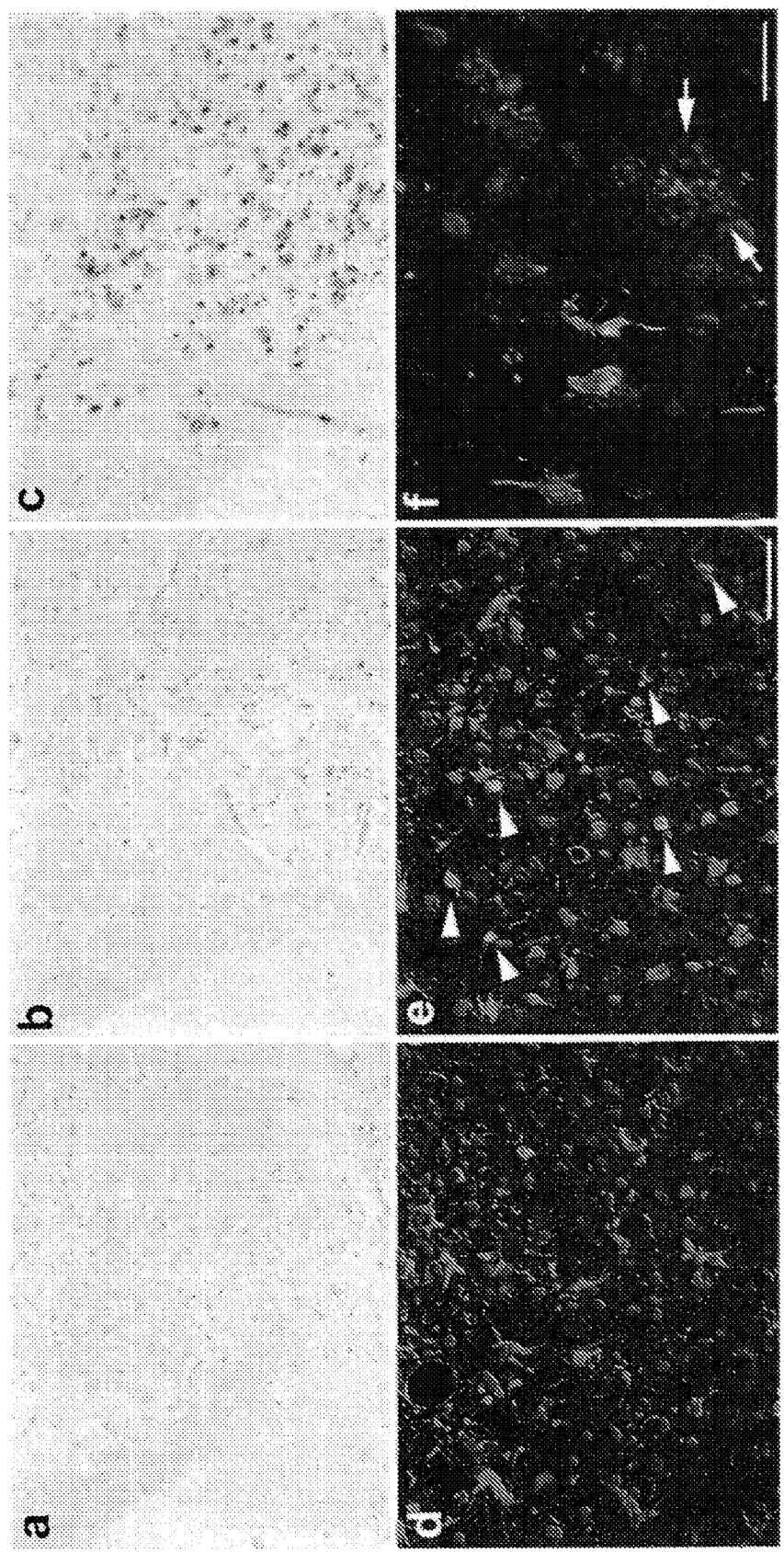
FIG. 4: Intracellular age-dependent staining of AβpE3 oligomers and passive immunization with 9D5 is therapeutically effective in 5XFAD mice. Staining with 9D5 in the subiculum of (a) 3-, (b) 6- and (c) 12-month-old 5XFAD mice showing that the signal starts to appear at 6 months. (d) Double-staining using 9D5 (red) and the astrocytic marker GFAP (green) in the subiculum of a 12-month-old 5XFAD mouse revealed no co-localization in astrocytes. (e) In contrast, double-staining using 9D5 (red) and the microglia/macrophage marker Iba-1 (green) showed a strong co-localization in the subiculum of a 12-month-old 5XFAD mouse (arrowheads). (f) Strong intraneuronal 9D5-immunoreactivity could be demonstrated in the pons of a 12-month-old 5XFAD mouse. There was a significant therapeutic effect on behavioral deficits following passive immunization with 9D5 for six weeks in 5XFAD mice (age at analysis six months). Scale bar: a: 200 μm, b: 100 μm, c-d: 50 μm.
Figure 5:
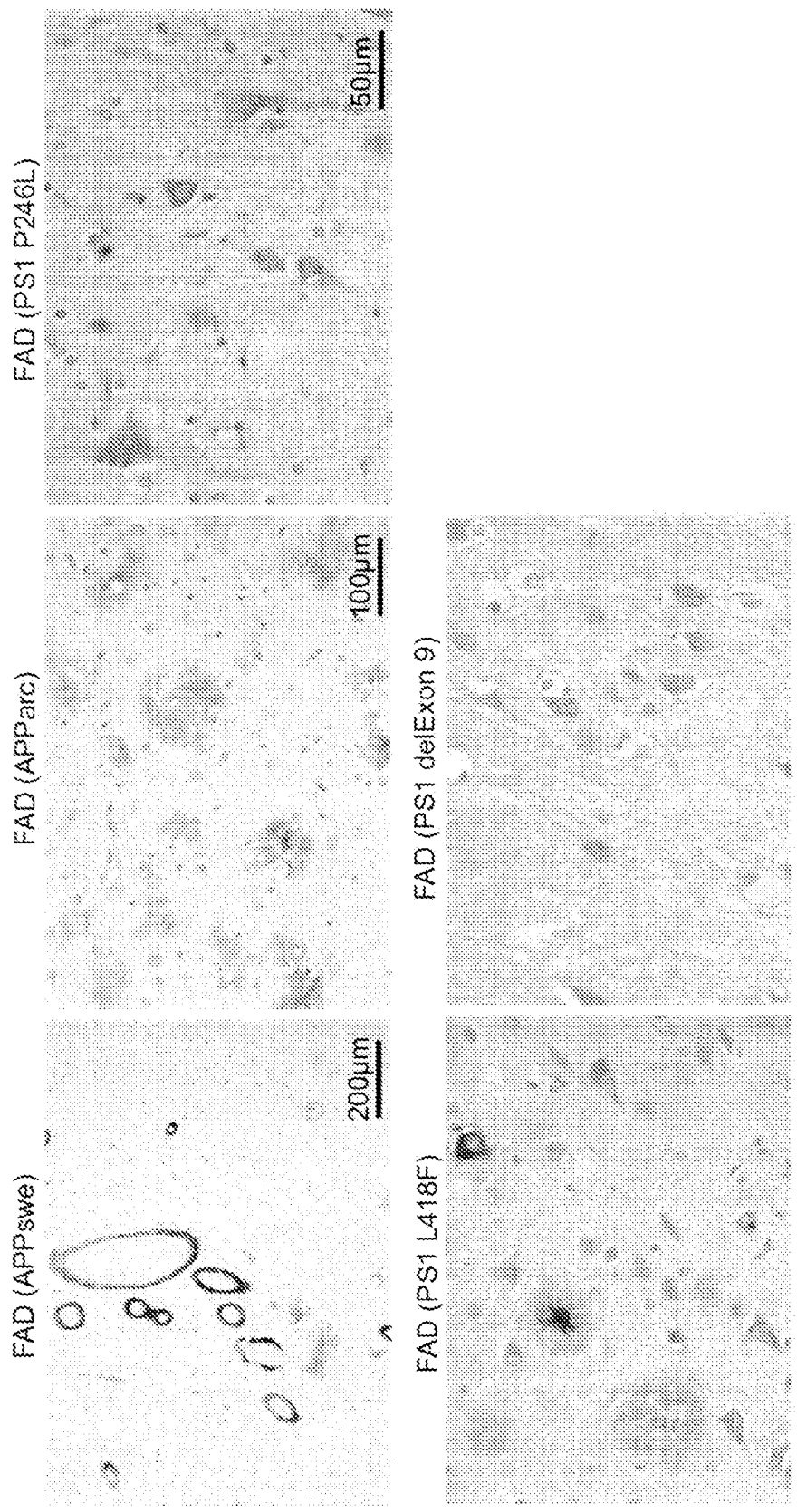
FIG. 5: Immunostaining of patient samples. FAD cases with mutations in the APP gene (Swedish or arctic mutation) reveal abundant 9D5 immunoreactivity. Of interest, all FAD cases harboring mutations in the Presenilin-1 gene (P264L, L418F, PS1Δexon9) showed prominent intraneuronal 9D5 immunoreactivity.

Staining of 3-month-old 5XFAD mice using 9D5H6 did not show any immunoreactivity (FIG. 4, a), whereas considerable staining was detected in the subiculum of 6-month-old 5XFAD mice (FIG. 4, b), showing a dramatic increase at the age of 12 months (FIG. 4, c). In addition, other brain areas like cortex, pons or brain stem nuclei stained strongly positive at that time point (not shown).

Figure 13:
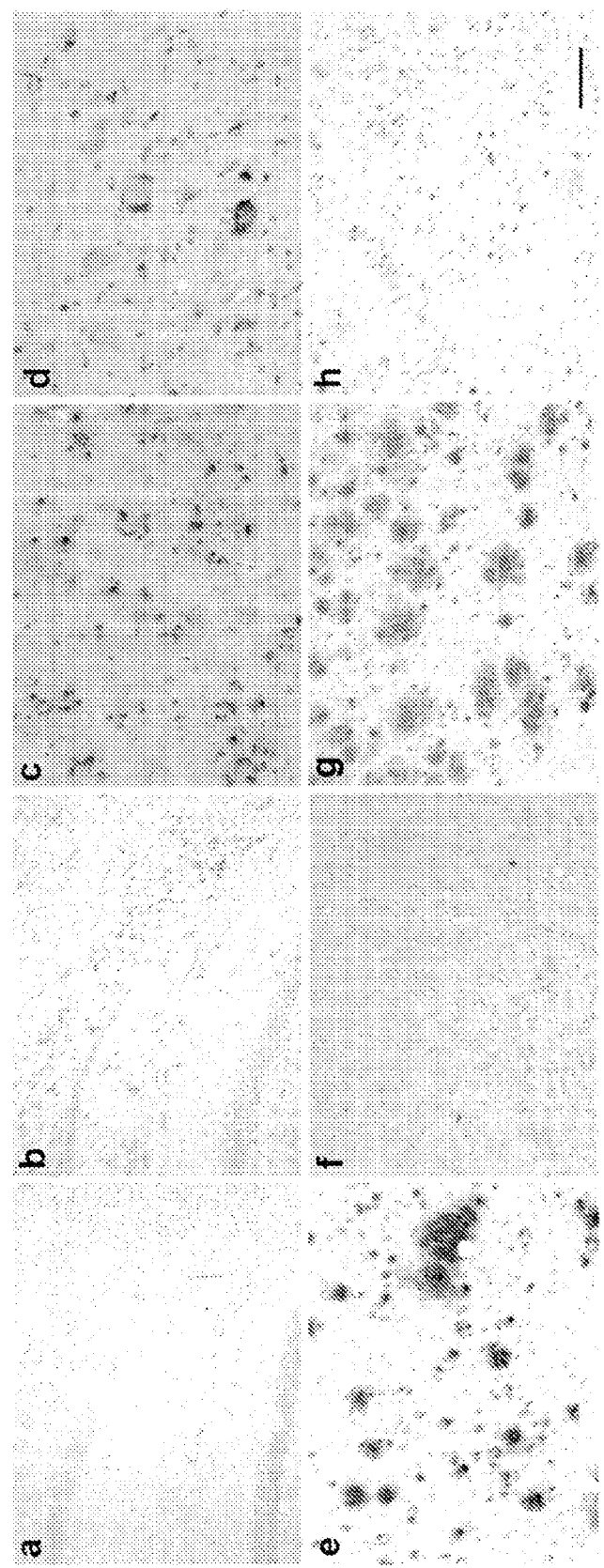
FIG. 13: 9D5 immunoreactivity APP/PS1KI and APP single transgenic mice. In 2-month-old APP/PS1KI did not show any 9D5 immunoreactivity in the subiculum (a), whereas in 10-month-old APP/PS1KI mice abundant 9D5-staining could be detected (b). In cortical regions, abundant 9D5 staining could be detected already at the age of 6 month (c). In addition, strong intraneuronal 9D5 staining could be detected in spinal cord motor neurons at 12 months of age (d). 10-month-old APP single transgenic mice showed abundant 4G8 staining (e) and only minor 9D5-immunoreactivity (f). Age-matched APP/PS1KI bigenic mice harbouring mutant PS1 on a homozygous knock-in background showed strong 4G8 staining (g), as well as abundant 9D5 immunoreactivity (h). Scale bars: a,b: 200 μm, e-h: 100 μm, c,d: 50 μm.

A very similar age-dependent accumulation of AβpE3 was also observed in APP/PS1KI mice, another model with robust neuron loss and associated behavioral deficits (Casas, C., et al. *Am J Pathol* 165, 1289-1300 (2004). Wirths, O. et al. *Neurobiology of Aging* 29, 891-901 (2008)) (FIG. 13).

In addition, double-staining using 9D5H6 (red) and the astrocytic marker GFAP (green) in the subiculum of a 12-month-old 5XFAD mouse revealed almost no co-localization in astrocytes (FIG. 4, d). On the other hand, double-staining using 9D5H6 (red) and the microglia/macrophage marker Iba-1 (green) showed a strong co-localization in the subiculum of a 12-month-old 5XFAD mouse, leading to the suggestion that there is an uptake of 9D5H6-positive material by microglia cells (FIG. 4, e (arrowheads), f). In addition, strong intraneuronal 9D5H6-immunoreactivity could be demonstrated in the pons of a 12-month-old 5XFAD mouse (FIG. 4, f, arrows).

Example 9

Sandwich ELISA of Plasma Samples

To assess the potential of oligomeric AβpE3 variants and antibody 9D5 in diagnosis, the inventors established a novel ELISA and tested plasma of AD patients and healthy controls (HC).

For ELISA analysis ninety-six-well plates (maxisorp, Nunc) were coated overnight with 3 µg/ml of monoclonal antibody 9D5H6 in carbonate buffer pH 9.6 at 4° C. Subsequently, the plates were washed three times with PBS and blocked for 2 hr with PBS containing 5% w/v milk powder and 0.05% Tween 20 at room temperature. Plates were washed three times with PBS and 20 µl of 0.1% azide in PBS were added for blocking of serum including peroxidases. Undiluted human sera were added (50 µl each) and incubated for 1 hr at 37° C. The plates were again washed three times with PBS and incubated with biotinylated anti AβpE3 2-48 (Synaptic Systems) at 1 µg/ml in PBS/1% BSA for 1 hr at 37° C. Plates were washed three times with PBS and Streptavidin HRP (BD Pharmigen) was added at 1:4000 dilution in PBS/1% BSA and then incubated for 1hr at 37° C. The plates were washed three times with PBS and subsequently developed with TMB peroxidase substrate (Sigma) for 10 min. As a negative control the same procedure, with the exception of coating of 9D5H6, was used. The demographic data of individuals for the plasma assay was as follows: age; AD patients (78±1.8) and HC (69±1.4); MMSE; AD (11.4±3.2) and HC (29±0.3); sex; AD (3 male/13 female) and HC (5 male/5 female).

Figure 6:
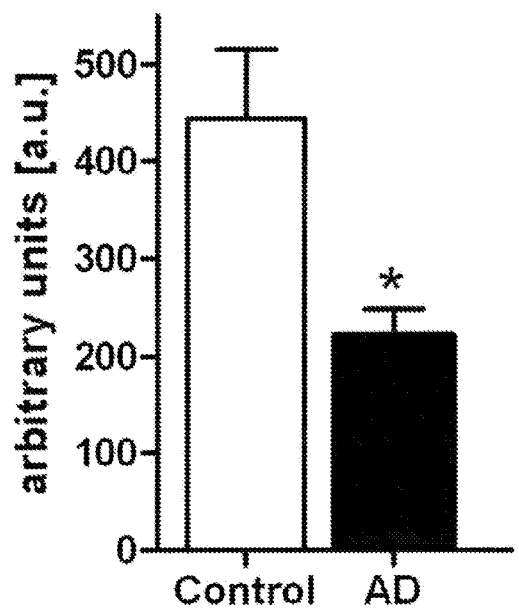
FIG. 6: Plasma levels of AβpE3 in patient samples. Plasma levels of AβpE3 oligomers. Sandwich ELISA with 9D5 as capture antibody and 2-48 as detector antibody demonstrating reduced plasma levels of AβpE3 oligomers in AD patients as compared to non-demented controls (unpaired t-test, P<0.05). The demographic data of individuals for the plasma assay was as follows: age; AD patients (n=16; 78±1.8) and non-demented controls (n=10; 69±1.4); MMSE; AD (11.4±3.2) and controls (29±0.3); sex; AD (3 male/13 female) and controls (5 male/5 female).

A small pilot study on oligomer levels in plasma of AD patients (n=16) and healthy controls (HC, n=10) revealed that AD patients had significantly lower levels of AβpE3 oligomers (P<0.05) (FIG. 6). AD patients had a significantly reduced (−46%) level of ELISA signal.

TABLE 1

Demographic data of sporadic (AD) and familial (FAD) Alzheimer disease patients with APP (arc, artic; swe, Swedish) and PS1 mutations ((P264L, L418F, Δexon9) and non-demented controls. Oligomeric AbpE staining in sporadic and familial AD cases was observed in pyramidal neurons and blood vessels (CAA) of the hippocampus and frontal cortex. Minor plaque staining was only seen in some AD cases.

|  | sex | age | Oligomeric AβpE3 | | | Braak stage | ApoE |
|---|---|---|---|---|---|---|---|
|  |  |  | iAβ | CAA | Plaques |  |  |
| control | m | 73 | − | − | − | 0 | 33 |
| control | f | 82 | − | − | − | I | 33 |
| control | m | 78 | − | (+) | − | I | 43 |
| control | m | 84 | − | − | − | I | 33 |
| control | m | 91 | − | − | − | I | 33 |
| control | m | 70 | − | − | − | 0 | 43 |
| control | f | 78 | − | − | − | I | 33 |
| control | m | 70 | − | − | − | 0 | 32 |
| control | f | 90 | − | (+) | − | I | 22 |
| control | f | 88 | − | − | − | I | 33 |
| AD | f | 79 | + | + | + | IV | 43 |
| AD | m | 93 | − | + | − | IV | 33 |
| AD | f | 86 | − | + | − | IV | 43 |
| AD | f | 86 | − | − | − | IV | 33 |
| AD | m | 86 | − | (+) | + | IV | 33 |
| AD | m | 92 | − | − | − | IV | 33 |
| AD | f | 92 | − | (+) | − | IV | 33 |
| AD | f | 88 | − | − | − | IV | 33 |
| AD | f | 85 | + | − | − | IV | 22 |
| AD | f | 88 | − | (+) | − | IV | 43 |
| AD | m | 81 | − | + | + | IV |  |
| AD | f | 84 | + | − | + | IV | 32 |
| AD | f | 84 | + | + | − | IV | 43 |
| AD | m | 91 | − | + | − | IV | 42 |
| AD | f | 88 | − | − | + | IV | 33 |
| AD | f | 91 | − | + | − | IV | 43 |
| AD | f | 87 | − | + | − | IV | 43 |
| AD | f | 92 | + | (+) | − | IV | 42 |
| AD | f | 91 | − | (+) | − | IV | 43 |
| AD | f | 93 | − | − | − | IV | 33 |
| FAD arc | m | 64 | (+) | + | + | na | na |
| FAD swe | f | 61 | (+) | ++ | + | na | na |
| FAD PS1 (P264L) | m | 54 | + | + | + | na | na |
| FAD PS1 (L418F) | m | 38 | ++ | − | ++ | na | na |
| FAD PS1 (Δexon9) | m | 61 | ++ | + | − | na | na |
| FAD PS1 (Δexon9) | m | 64 | ++ | + | − | na | 33 |
| FAD PS1 (Δexon9) | m | 69 | ++ | + | − | na | 33 |

Abbreviations: iAb, intraneuronal Ab; CAA, cerebral amyloid angiopathy; m, male; f, female; na, not analyzed.

There is accumulating evidence to suggest that intraneuronal Aβ is a major risk factor for neuron loss and a trigger for the β-amyloid cascade of pathological events. Extracellular Aβ deposition has long been challenged to be a correlate for the striking region specific neuron loss, like the layer two pyramidal neurons in the entorhinal cortex and the CA1 neurons in the hippocampus. Interestingly, a link between the β-amyloid hypothesis and neuron loss in the hippocampus has recently been demonstrated in several mouse models expressing familial APP and PS-1 variants and the TBA2 mice. Intracellular Aβ detection in transgenic mice is well documented. The inventor's present work clearly demonstrates that AβpE3-42 forms SDS stable low molecular oligomers that can be detected with the novel antibody 9D5H6. The antibody is a valuable tool to differentiate between non-demented healthy controls and sporadic AD patients, as they do not stain plaques even in those control cases with abundant plaque load. In sporadic AD cases only a minor portion of plaques was labeled. Most strikingly strong intraneuronal staining was observed in sporadic and familial AD cases with different APP and PS1 mutations. This staining pattern indicates that the oligomeric-specific antibodies recognize a distinct Aβ species that strongly aggregates within large pyramidal neurons in hippocampus and cortex of AD cases. Moreover, since CAA is frequently observed with the antibodies, it is tempting to speculate that the oligomers cannot cross the blood brain barrier and trigger vessel pathology in AD. In 5XFAD and APP/PS1KI mice, the staining is absent in young mice. It appears within neurons and microglia cells at a time point coinciding with the onset of behavioural deficits synaptic dysfunction and neuron loss. The staining in reactive microglia cells might reflect the fact that in mouse models the pathology is ongoing for several months whereas in human AD patients the duration is many years prior to death. The microglia staining however indicates reactive microglia is involved in the disease process. Whether it is part of a clearing process getting rid of potentially toxic oligomers or part of the pathological process needs to be studied in greater detail.

The occurrence and relevance of intraneuronal Aβ accumulations in AD have been a matter of controversial scientific debate. First reports showing that Aβ is initially deposited in neurons before occurring in the extracellular space date back roughly 20 years. More recently it has been shown that neurons in AD-vulnerable regions accumulate Aβ42 and it has been further suggested that this accumulation precedes neurofibrillary tangle formation and extracellular Aβ deposition. Consecutively a variety of reports have been published demonstrating Aβ in neurons of AD (D'Andrea M R, et al. (2002) *Neurosci Lett* 323(1):45-49; D'Andrea M R, et al. (2001) *Histopathology* 38(2):120-134; Fernandez-Vizarra P, et al. (2004) *Histol Histopathol* 19(3):823-844; Mochizuki A et al. (2000) *Lancet* 355(9197):42-43) and Down syndrome (DS) patients (Gyure K A, et al. (2001) *Arch Pathol Lab Med* 125(4):489-492; Mori C, et al. (2002) *Amyloid* 9(2):88-102; Busciglio J, et al. (2002) *Neuron* 33(5):677688). On the contrary, a more recent study described intracellular Aβ immunoreactivity during the entire life span in control subjects and DS patients, leading to the suggestion that this represents rather a feature of normal neuronal metabolism than a pathological alteration. As the authors found the strongest intraneuronal Aβ in brain structures that are not highly vulnerable to AD-associated changes, they believe that intraneuronal Aβ immunoreactivity is not a predictor of brain amyloidosis or neurofibrillary degeneration. Aoki and colleagues investigated whether Aβ levels are changed in CA1 pyramidal neurons of AD hippocampus, using laser capture microdissection to isolate neurons and enzyme-linked immunosorbent assay for quantification. The results showed increased Aβ42 levels and an elevated Aβ42/Aβ40 ratio in neurons from sporadic as well as from familial AD cases, whereas Aβ40 levels remained unaffected (Aoki M, et al. (2008) *Neuroreport* 19(11):1085-1089). The presence of one or two ApoE4 alleles strongly correlated with an increased accumulation of intraneuronal Aβ detected with an antibody against the N-terminal aspartate of full-length Aβ. However this was true also in nondemented controls. In another study, it was shown that using laser capture microdissection microscopy for isolation of Purkinje neurons and CA1 hippocampal neurons from AD cases and controls, and quantified the low levels of intracellular Aβ using a novel and highly sensitive ELISA. The intracellular levels of AβX-42, as well as the AβX-42/AβX-40 ratio, were increased in neurons from sporadic AD cases as compared to controls (Hashimoto M, et al. (2010) *Acta Neuropathol* 119(5):543-554).

The inventors have previously demonstrated that intraneuronal AβpE3-42 expression is highly toxic in vivo, and that the induced neuron loss is associated with a lethal neurological phenotype in TBA2 transgenic mice (Wirths (2009) Acta Neuropathol 118: 487-496). The severity of the neurological phenotype observed in TBA2 mice, accompanied by Purkinje cell loss and premature mortality reflects the in vivo toxicity of AβpE3-42. Interestingly, 85% of Aβ peptides in the APP/PS1KI mice terminated at position 42, the N-terminus shows a large heterogeneity including AβpE3. The time point of high levels of AβpE3-42 coincided with the onset of behavioural deficits in both mouse models. By six month, the APP/PS1KI mice exhibit a neuron loss in CA1 of the hippocampus, the frontal cortex, and in distinct cholinergic nuclei. Overall, the pathological events seen in the APP/PS1KI mouse model might be at least partly triggered by AβpE3-42 accumulation.

It has been suggested that the removal of N-terminal amino acids 1 and 2 of Aβ☐ could be carried out by a hypothetical peptidase, and very recently it has been shown that aminopeptidase A may be responsible for the N-terminal truncation of full-length Aβ peptides. A subsequent glutamate cyclization by a glutamate cyclase leading to pE formation may protect the peptide from degradation and even make it more prone to accumulate. In in vitro experiments it has been shown that cyclization of glutamate at position 3 of Aβ can be driven enzymatically by glutaminyl cyclase (QC). In addition, it has been demonstrated that QC inhibition significantly reduced AβpE3 formation, emphasizing the importance of QC-activity during cellular maturation of pyroglutamate-containing peptides.

N-truncated AβpE3 peptides have been identified by several groups in AD brains. N-terminal deletions in general enhance aggregation of β-amyloid peptides in vitro. AβpE3 has a higher aggregation propensity, and stability, and shows an increased toxicity compared to full-length Aβ. It has been suggested that N-truncated Aβ ☐peptides are formed directly by BACE and not through a progressive proteolysis of full-length Aβ1-40/42.

The inventors have previously published that the level of IgM autoantibodies in plasma directed against AβpE3 was significantly decreased in AD patients as compared to healthy controls. In good agreement with these observations, the signal of AβpE3 oligomers detected by 9D5 was significantly lower in plasma of AD patients again pointing out that 9D5 can be used as a biomarker tool for AD diagnosis.

Example 10

Dot Blot Competition and ELISA Competition

PVDF membrane (Millipore) was activated in methanol for 3 seconds, washed with ddH$_2$O and equilibrated in transfer buffer (25 mM Tris, 192 mM glycine, 20% methanol).

Serial 1:2 dilutions of the human AβpE3-38 corresponding to 1 μg, 500 ng and 250 ng in H$_2$O were spotted on the wet PVDF membrane and left to dry for 10 minutes. After blocking of the membrane by 5% non-fat dry milk TBST solution the competitor antibodies 9D5H6/"9D5" (IgG2b subclass) and 8C4D2 (IgG1 subclass) were diluted in 5% non-fat dry milk TBST solution (10 μg/ml) and incubated with the membrane over night at 4° C. while gently shaking. Then the corresponding detector antibody (8C4D2 after pre-incubation with 9D5H6 and vice versa) was added (at 10 μg/ml) to each competitor antibody solution and incubated by gently shaking for two hours. After washing the membrane three times in 1×TBST for 15 minutes, IgG2b and IgG1 subclass-specific secondary antibodies conjugated to Cy3 (Jackson Immunoresearch) were diluted 1:200 in 5% non-fat dry milk TBST and used to cover the membrane probed with the 9D5H6 and 8C4D2 respectively with gentle shaking for one hour. Then the membrane was washed three times by 1×TBST for 15 minutes. Fluorescent dots were scanned using a Fuji CCD camera LAS-4000 mini and a fluorescence filter. Preincubation of the membrane with 9D5H6 prior detection with 8C4D2 significantly reduced the 8C4D2 associated signal strength indicating a blocking of the 8C4D2 binding site. The same is true for the inverse experiment. Preincubation with 8C4D2 significantly reduced binding of 9D5H6; see also FIG. 7. This suggests an epitope shared by both antibodies.

In ELISA competition assay 9D5H6 or 8C4D2 (3 μg/ml) was coated over night in carbonate buffer pH 9.6 in 96 well plates (Nunc Maxisorp) and blocked next day with PBS containing 5% w/v skimmed milk powder and 0.05% Tween 20 at room temperature for 2 h. 2 μg of Peptide AβpE 3-38 was pre incubated with 5 μg or 3 μg of 9D5 or 8C4 in PBS 1% BSA (100 μl per well) for 30 min at 37° C. Subsequently, 9D5 pre treated peptides were added on 8C4 coated wells and 8C4 pre treated peptides were incubated in 9D5 coated wells and incubated for 1 h at 37° C. Plates were washed three times with PBS and incubated with biotinylated detection antibody 2-48 (1 μg/ml, Synaptic Systems) for 1 h at 37° C. Plates were washed three times with PBS and incubated with Streptavidin HRP at 1:4000 dilution in PBS/1% BSA incubated for 1 h at 37° C. The plates were washed three times with PBS and subsequently developed with peroxidase substrate (TMP, Pierce).

Preincubation of the AβpE 3-38 with 9D5H6 prior detection with 8C4D2 abolished the 8C4D2 associated signal indicating a blocking of the 8C4D2 binding site (data not shown). The same is true for the inverse experiment (data not shown). Preincubation AβpE 3-38 with 8C4D2 blocked binding of 9D5H6. This suggests an epitope shared by both antibodies.

Example 11

Immunostaining Competition

Figure 8:
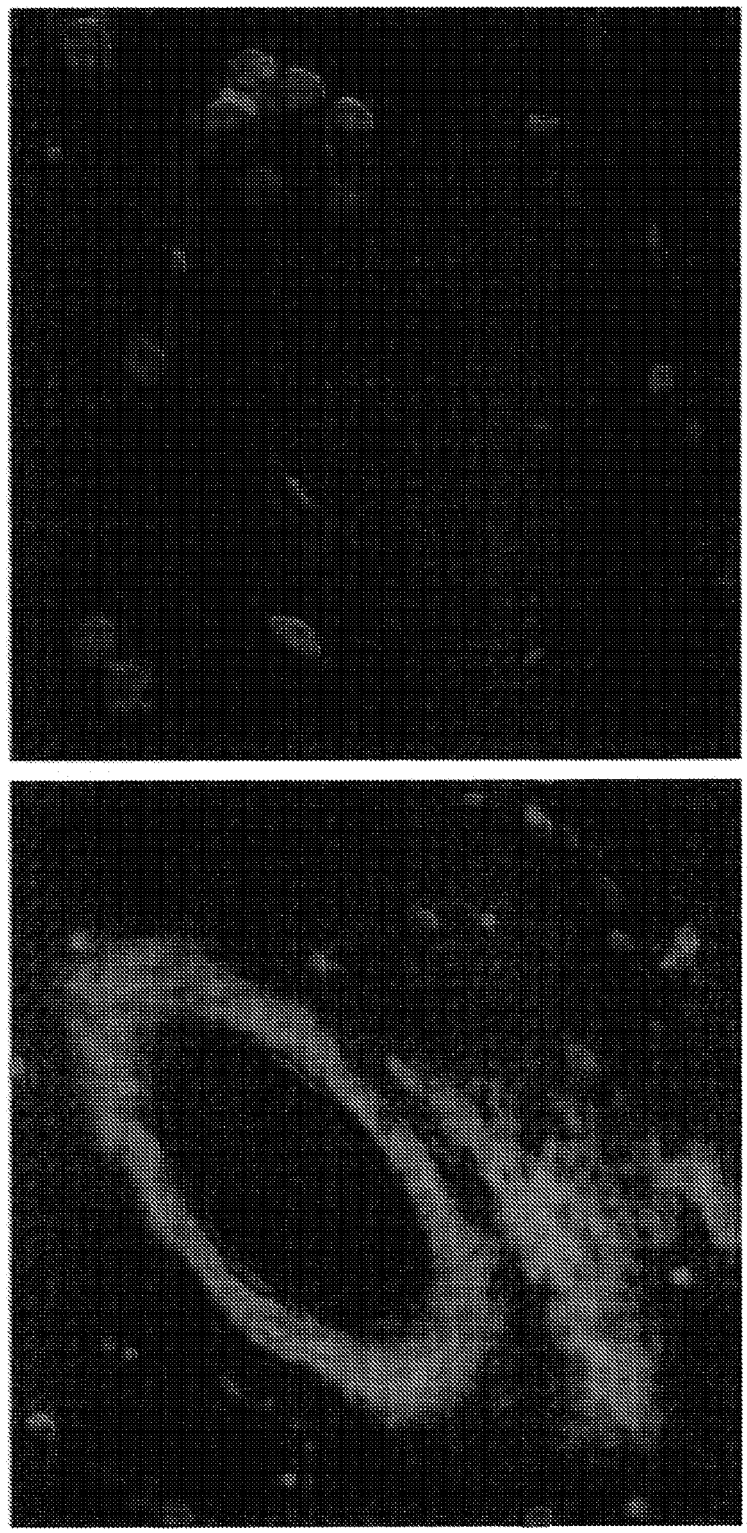
FIG. 8: Immunostaining competition assay. Competition of 8C4D2 signal by application of 9D5H6/"9D5" competitor antibody in human brain from a patient with sporadic AD. 8C4D2 staining in red (left side) demonstrated abundant blood vessel staining, which was blocked by competition with 9D5H6 (right side). DAPI staining against nuclei (blue).

Immunostaining on paraffin embedded sections was performed on 4 μm sagital paraffin sections, as described above. In order to study competition between 8C4D2 and 9D5H6, the specific binding sites of 8C4D2 (IgG1 subclass; 10 μg/ml) were blocked by application of the competitor antibody 9D5H6 (IgG2b subclass) (0.04 μg/ml) together with the non-specific treatment with skim milk and fetal calf serum in PBS, prior to the addition of the primary antibodies. Primary antibody 8C4D2 (10 μg/ml) was incubated overnight in a humid chamber at room temperature, followed by incubation with a IgG1 subclass specific secondary antibodies conjugated to Cy3 (Jackson Immunoresearch) diluted 1:200 in 5% non-fat dry milk TBST. Results are shown in FIG. 8. Preincubation of the brain section with 9D5H6 prior detection with 8C4D2 abolished the 8C4D2 associated signal indicating a blocking of the 8C4D2 binding site. This suggests an epitope shared by both antibodies; see also FIG. 10.

Figure 7:
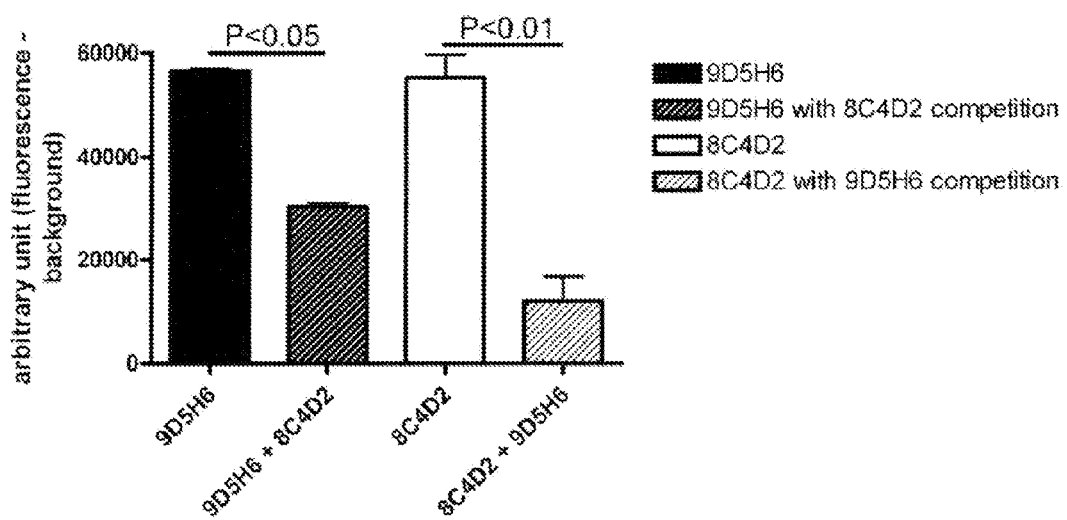
FIG. 7: Dot blot competition assay. Significant lower 9D5H6/"9D5" signal was detected after competition with 8C4D2 (P<0.05). That same was observed for the 8C4D2 signal after competition with 9D5H6/"9D5" (P<0.01) by t-testing (ANOVA demonstrated significant differences across all groups, P<0.01). Arbitrary unit is fluorescence minus background. Quantification is shown for 500 ng AβpE3-38 spotted on nitrocellulose membrane.

9D5 and 8C4 were competing for the same epitope in dot blot analysis and showing an indistinguishable staining pattern using immunohistochemistry (FIG. 7, 8, 10).

Example 12

Size-Exclusion Chromatography (SEC) Followed by Dot Blot

In order to analyze the binding properties of the oligomeric AβpE3 antibody (9D5), size exclusion chromatography (SEC) was performed under native conditions with N-terminally truncated and modified AβpE3-42 and wild-type Aβ1-42 peptides followed by dot blot analysis.

Prior to experiments, synthetic Aβ peptides (PSL) were monomerized in 98% formic acid (Rohrer, D. C. et al. *Cell Transplant* 5, 57-68 (1996)). After immediate evaporation of the solvent, peptides were dissolved to 1 mg/ml in 0.1% ammonia following ultrasonic treatment. Size-exclusion chromatography was performed using a Superdex 75 (10/30HR) column (Amersham Bioscience). Aliquots of freshly dissolved 0.2 mg synthetic peptide were loaded and 0.5 ml fractions were eluted with 1×PBS (137 mM NaCl, 2.7 mM KCl, 10 mM Na$_2$HPO$_4$, 2 mM KH$_2$PO$_4$) at a flow rate of 0.5 ml/min. For detection of Aβ peptides by dot blot, fractions were spotted on 0.2 μm Nitrocellulose and either detected by monoclonal W0-2 (the Genetics Company) or 9D5 antibody. Different batches of Aβ peptides were used to exclude individual differences which were not observed throughout all studies.

Figure 11:
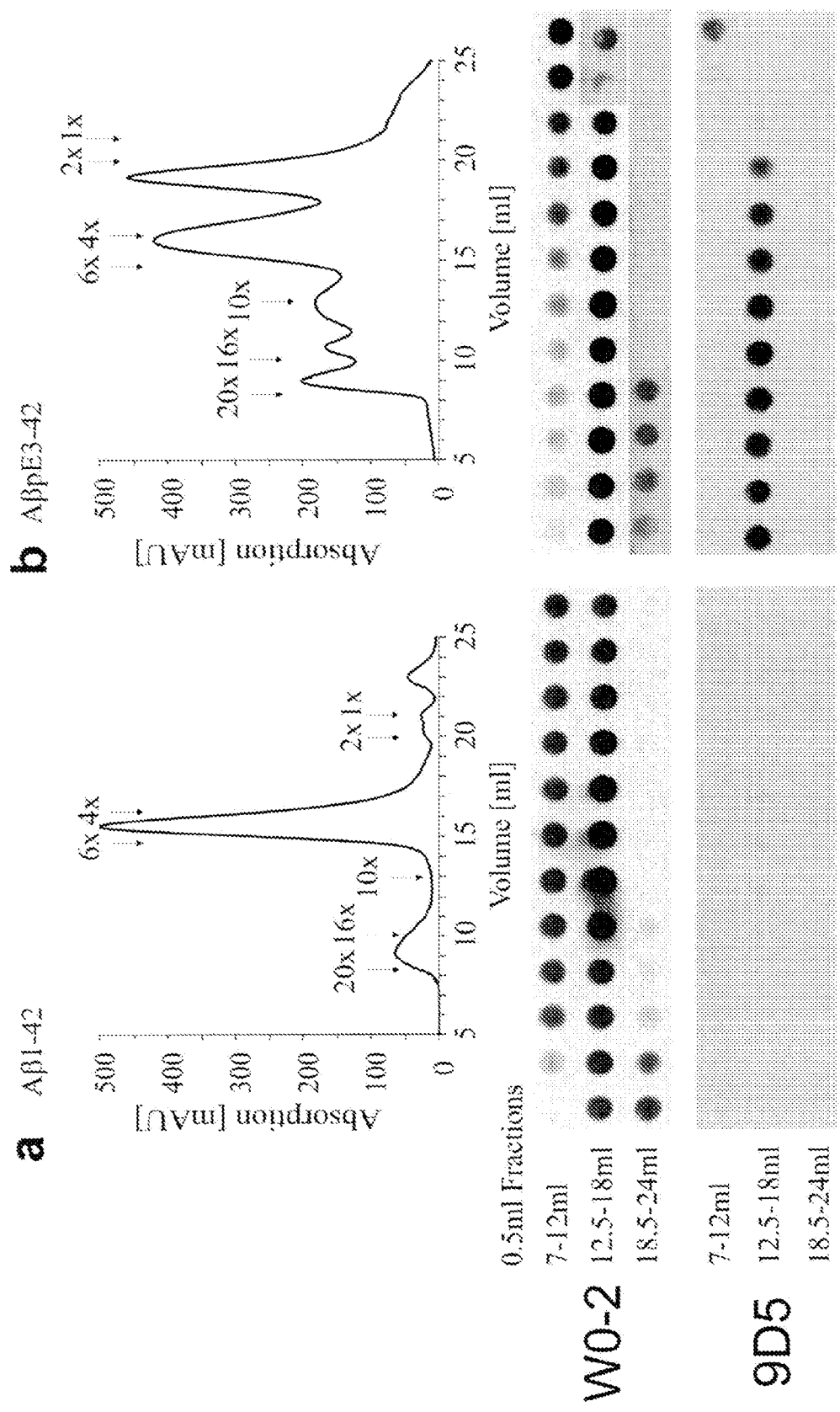
FIG. 11: 9D5 recognized AβpE3 oligomers and inhibited AβpE3 aggregation in vitro. (a) Aβ1-42 peptides formed mainly low-n oligomers (4×-6×) and only minor amounts of higher aggregates (10×-20×) and monomers and dimers (1×-2×). All Aβ1-42 forms were detectable by dot blot with W0-2, while 9D5 did not show any signal. (b) The separation profile of AβpE3-42 peptides showed high amounts of monomers to hexamers (1×-6×) and lower amounts of higher aggregates (10×-20×). Again, W0-2 recognized all aggregation forms of AβpE3-42 with different sensitivity (Note, longer exposure of AβpE3-42 fractions 17-24 ml). 9D5 however solely detected low-n oligomers (4x-10x) and no smaller or larger oligomers.

SEC of Aβ1-42 showed the well known distribution of low-n oligomers (4×-6×) with some higher (16×-20×) and few smaller (1×-2×) aggregates. SEC of AβpE3-42 yielded high levels of smaller forms (1×-2×), low-n oligomers (4×-6×) and lower levels of higher oligomeric aggregates (10×-20×), indicating differential aggregation characteristics of Aβ1-42 and AβpE3-42. All Aβ1-42 and AβpE3-42 SEC fractions were recognized by the generic Aβ antibody W0-2 in a dot blot analysis. In contrast the 9D5 antibody detected only low-n oligomeric fractions (4×-10×) of AβpE3-42, whereas no signal was obtained using the Aβ1-42 fractions (FIG. 11a,b). Under denaturing conditions 9D5 detected one single band of low molecular weight (LMW) AβpE3-42 without any cross reactivity for Aβ1-42. As expected, W0-2 detected a range of aggregation states of Aβ1-42 peptides as well as monomeric Aβ1-42 (FIG. 2). Together, these data demonstrate that 9D5 is highly selective for lower oligomeric variants of AβpE3-42.

Example 13

Thioflavin T Aggregation Assay

The aggregation of monomeric Aβ1-42 and AβpE3-42 peptides (55 μM) was investigated using a ThT fluorescence assay. Aggregation of Aβ1-42 and AβpE3-42 was also analyzed by real-time ThT fluorescence.

Peptides were solubilized in 10 mM NaOH at a concentration of 1 mg/ml, sonicated for 5 min, frozen in liquid nitrogen, and stored at −80° C. until use. Aggregation of Aβ peptides was investigated online using ThT aggregation assay (Varian fluorescence spectrophotometer) using an excitation wavelength of 446 nm and emission wavelength of 482 nm.

Samples contained 55 µM of Aβ, 50 mM sodium phosphate buffer (pH 7.4), 50 mM NaCl, 20 µM ThT and 0.01% sodium azide. The samples were incubated at 37° C. in a peltier adapter with stirring. Data points were recorded every 10 min during the assay.

Figure 12:
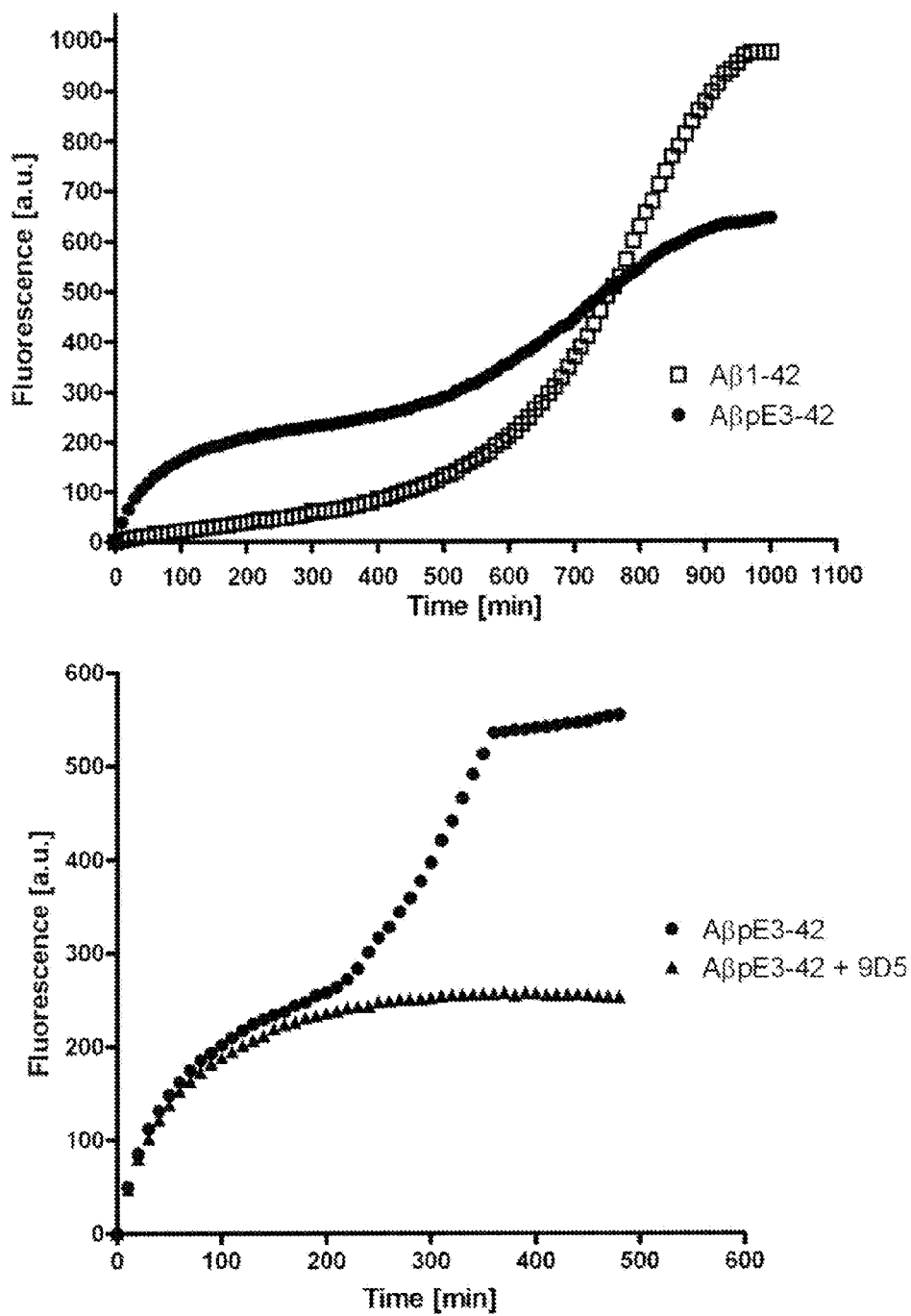
FIG. 12: Aggregation kinetics of Aβ1-42 and AβpE3-42 monitored by ThT fluorescence. (a) Aggregates were very rapidly generated from AβpE3-42, indicating an instant seeding of the aggregation process. Aβ1-42 showed a typical lag phase, i.e. the phase in which oligomers and protofibrils are slowly formed, whereas AβpE3-42 rapidly formed intermediate oligomeirc assemblies, but has decreased propensity to form larger fibrils, a behaviour that clearly differs from that of that of Aβ1-42. (b) Accelerated increase after the inflection point at 200 min was efficiently blocked by addition of 9D5 together with AβpE3-42.

While Aβ1-42 showed the expected aggregation behaviour with a pronounced lag phase before fibril growth, AβpE3-42 showed very rapid formation of intermediate oligomeric assemblies. Interestingly, elongation rates of AβpE3-42 were much slower as that of Aβ1-42. These data indicate that AβpE3-42 rapidly formed intermediate oligomeric assemblies, but has decreased propensity to form larger fibrils, a behavior that clearly differs from that of that of Aβ1-42 (FIG. 12a). Notably, presence of antibody 9D5 efficiently decreased the formation of higher aggregates of the AβpE3-42 peptide at a 1:76 (9D5:A13), but not the rapid formation of lower oligomers, further demonstrating the specificity of this antibody for lower oligomeric species of AβpE3 and its efficiency in the inhibition of further peptide aggregation (FIG. 12b). This observation suggests that 9D5 inhibits with the formation of higher Aβ aggregates by binding to LMW oligomers as indicated in SEC and Western blot experiments.

Example 14

Antibodies of the Invention Rescue Behavioural Deficits

The antibodies of this invention have been administered to a mouse model of Alzheimer Disease (5xFAD). 5xFAD bigenic mice have been described previously. These mice overexpress the 695 amino acid isoform of the human β amyloid precursor protein (APP695) carrying the "Swedish"-/"London"-/and "Florida" mutation. The 5xFAD bigenic mice (purchased from Jackson Laboratories, USA) express five FAD mutations three in APP K670N/M671L (770 residue isoform numbering), I716V and V717I and two in PS1 (M146L and L286V) introduced into APP(695). Both constructs are under the Thy1 promoter. All mice were backcrossed for more than 10 generations on a C57BL/6J genetic background. All animals were handled according to German guidelines for animal care. All research involving animals have been conducted according to guidelines of the German animal protection law. According to that the local committee for animal welfare at the University Medicine of Goettingen approved the experiments before the mice were sacrificed.

In an elevated plus maze, these mice show reduced anxiety behavior.

Spontaneous alternation rates were assessed using a cross-maze as described previously (Jawahr, S., et al. *Neurobiol Aging* (2010)). The alternation percentage was calculated as the percentage of actual alternations to the total number of arm entries. Anxiety levels were assessed using an elevated plus maze as described previously (Jawahr et al., supra). The elevated plus maze has the shape of a "+" with 2 alternate open and 2 alternate closed arms extending from a central platform. The whole maze is raised 75 cm above the floor. The open and enclosed arms of the plus maze generate exploratory behaviour and the avoidance of elevated open arms is an indication of the intensity of anxiety. During the test the mouse is placed onto the centre field and is allowed to explore the maze for 5 min. Anxiety can be measured by the time spent in the open arms, with lower anxiety levels corresponding to more time spent in open arms (Karl et al., 2003). The percentage of the time spent in the open arms to the overall time and the ratio of the open arms to the total arms entries were measured using an automatic video tracking system (VideoMot2, TSE-Systems, Germany).

Figure 9:
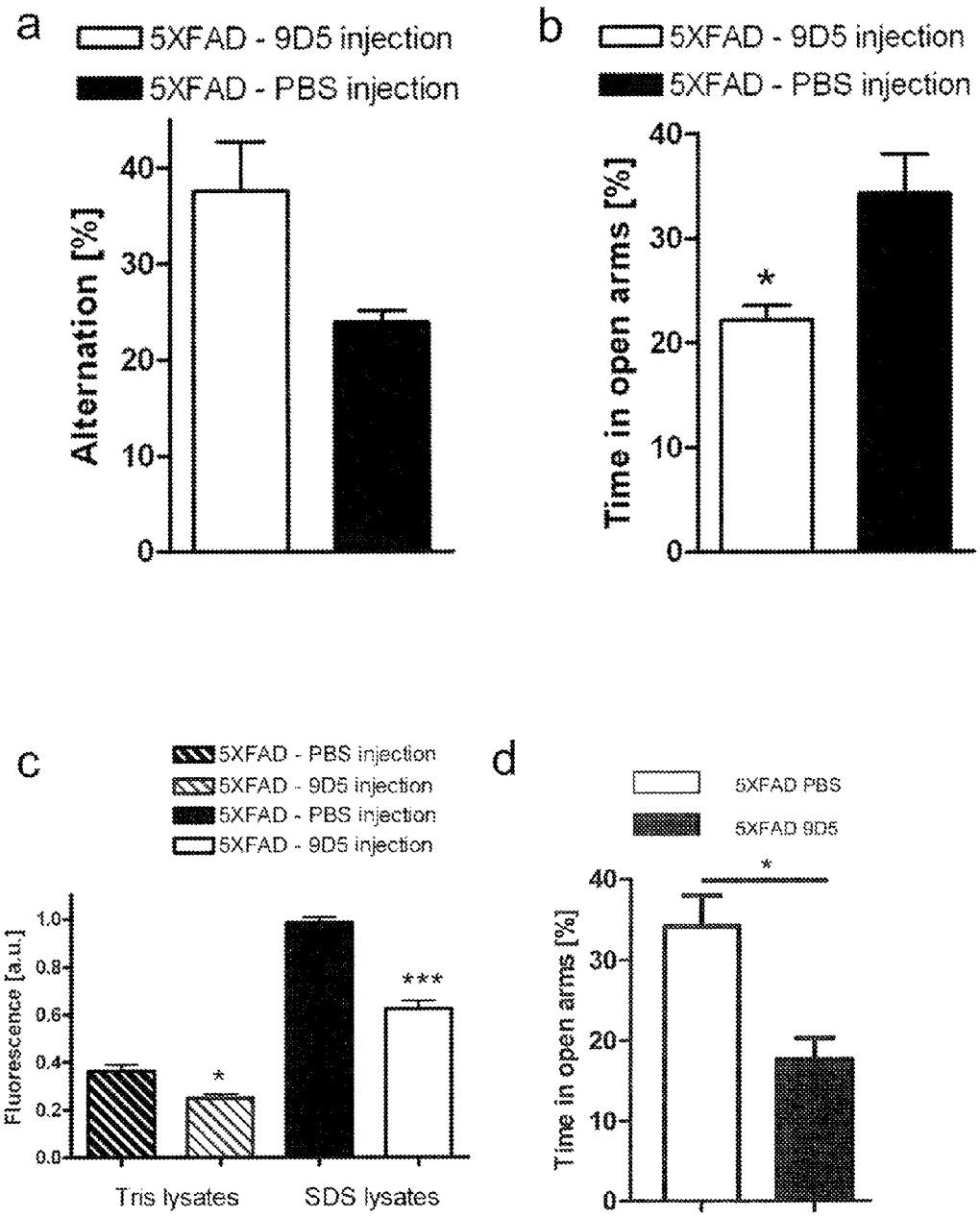
FIG. 9: Reduced behavioral deficits. (a) The cross-maze an alternation task monitoring working memory showed a trend to improvement (P=0.06), (b) whereas the elevated plus maze demonstrated normalized anxiety levels after 9D5 treatment (first cohort of 5XFAD mice) (P=0.03). (c) ELISA analysis of Tris and SDS lysates of PBS and 9D5 injected 5XFAD mice showing that 9D5 immunization reduced AβpE levels in both fractions significantly. In Tris lysates 9D5 immunization resulting in 31% reduced levels (P=0.0115) and SDS lysates resulting in 36% reduced levels (P=0.0001). (ANOVA of all groups; P=0.0001). (d) Second cohort of 6-month old 5XFAD mice tested for re-evaluation in the elevated plus maze, control (PBS-inj.) n=3. 9D5-inj. n=4.

4.5 months-old 5XFAD (female) mice were weekly injected with 250 µg 9D5 intraperitoneally for six weeks. 9D5 treatment normalized behavioral deficits in an alternation task (cross-maze (FIG. 9a), and in the elevated plus maze (FIG. 9b). A significant reduction of AβpE3 levels was observed in both the Tris and SDS fraction of brain lysates after 9D5 immunization of 5XFAD mice (FIG. 9c) supporting the rescue of behavioral deficits.

The Elevated plus maze task which is used to analyze anxiety levels of the tested mice revealed that a second cohort of 6-month old 5xFAD mice which had been treated with the 9D5 antibody spent significantly less time in the open arms of the maze (17.70±2.636 (n=4)) than the control group (34.27±3.741 (n=3)) (FIG. 9d). In fact, 6-month old immunized mice showed anxiety behavior similar to that of 4.5-month old untreated 5xFAD mice (23.47±6.019 (n=4)). This indicates that 9D5 treatment significantly stabilized performance in terms of anxiety levels. These results are in accordance with the previous data of a first cohort shown in FIG. 9b, which also showed that 9D5-immunized mice spent significantly less time in the open arms of the paradigm (22.13±1.398 (n=3)) and thus showed significantly higher anxiety levels than age-matched control mice (34.27±3.741 (n=3)). Here, too, immunized 6-month old mice performed like 4.5-month old untreated 5xFAD mice (23.47±6.019 (n=4)). This indicates that the immunization with 9D5 antibody improved/prevented the phenotype of 6-month old 5XFAD mice in terms of anxiety.

Soluble oligomers (also described as ADDLs and/or protofibrils) of Aβ have been discussed to be causally involved in synaptic and cognitive dysfunction in the early stages of AD. However, there is no consensus on which aggregation state is the most toxic pathogen in AD. Nanomolar concentrations of small diffusible Aβ oligomers (17-27 kDa) cause neuronal death in hippocampal slice cultures (Lambert, M. P., et al. *Proc Natl Acad Sci USA* 95, 6448-6453. (1998)). Aβ dimers that were either cell-derived or extracted from AD brains impair synaptic plasticity (Walsh, D. M., et al. *Nature* 416, 535-539. (2002)). Dodecameric Aβ56* oligomers extracted from the brain of APP transgenic mice interfere with learning and memory performance in rat (Lesne, S., et al. *Nature*. 440, 352-357. (2006)). Analysis of neurotoxicity of oligomers ranging from monomers to tetramers of synthetic Aβ peptides demonstrated that tetramers have the strongest effect (Ono, K., et al. *Proc Natl Acad Sci USA* 106, 14745-14750 (2009)). The conclusion that oligomers are more potent candidates as pathogens is based primarily on experimental evidence demonstrating that natural and synthetic Aβ oligomers impair synaptic plasticity, memory and inducing loss of synapses when applied exogenously into rat cerebral ventricle, cultured brain slices, or dissociated neurons. It has been shown that soluble oligomeric Aβ42 and not plaque-associated Aβ correlate best with cognitive dysfunction (McLean, C. A., et al. *Ann Neurol* 46, 860-866 (1999); Naslund, J., et al. *Jama* 283, 1571-1577. (2000)). Aβ oligomers are formed preferentially intracellularly within neuronal processes and synapses rather than within the extracellular space (Takahashi, R. H., et al. *J. Neurosci.* 24, 3592-3599. (2004); Walsh, D. M., et al. *Biochemistry* 39, 10831-10839. (2000)). Tomiyama et al. generated APP transgenic mice expressing the E693Δ mutation, which causes neuronal cell death and cognitive impairment by enhanced Aβ oligomerization without fibrillization. The mice displayed age-dependent accumulation of intraneuronal Aβ oligomers from 8 months but no extracellular amyloid deposits even at 24 months. Hippocampal synaptic plasticity and memory were impaired at 8 months of age (Tomiyama, T., et al. *J. Neurosci.* 30, 4845-4856 (2010)). Aβ protofibril levels correlate with spatial learning in AD transgenic mice expressing human APP with the arctic mutation (Lord, A., et al. *Febs J* 276, 995-1006 (2009)) facilitating early intraneuronal Aβ aggregation (Lord, A., et al. *Neurobiol Aging* 27, 67-77. Epub 2005 February 2017. (2006)). Despite the difficulty to compare the different studies on oligomeric Aβ species there seems to be converging evidence that they (1) are primarily formed within neurons, Oligomeric Aβ species are more neurotoxic than monomeric or fibrillar Aβ in vitro. (3) Oligomeric Aβ species decrease synaptic activity. (4) Generation of intraneuronal Aβ oligomers in transgenic mice induces neuron loss without plaque formation. (5) While Aβ42 levels decrease in CSF during AD progression, oligomeric Aβ species are increasing.

In the present study, the inventors have identified LMW AβpE3 oligomers, which can be detected by 9D5, a novel mouse monoclonal antibody. 9D5 did not cross react with any Aβ1-42 species indicating that these oligomers present a unique and novel epitope. The therapeutic potential of 9D5 was demonstrated in passively immunized 5XFAD mice as behavioral deficits were rescued. In an ELISA using 9D5 as capture antibody, the inventors could show that the signal was significantly lower in plasma of AD patients as compared to non-demented controls, indicating that 9D5 has diagnostic properties as well likely reflecting lack of clearance via the blood brain barrier.

Example 15

Passive Immunization with Antibodies of the Invention Leads to Reduction of Aβ Peptides in Plaques Extracellular Aβ load (4G8, 2-48) was evaluated in cortex and hippocampus using an Olympus BX-51 microscope equipped with an Olympus DP-50 camera and the ImageJ software (V1.41, NIH, USA). Serial images of 40× magnification (hippocampus) and 100× (cortex) were captured on six sections per animal which were 30 μm afar from each other. Using ImageJ the pictures were binarized to 16-bit black and white images and a fixed intensity threshold was applied defining the DAB staining. Measurements were performed for a percentaged area covered by DAB staining. Unpaired t-test was used to compare age-dependent changes in plaque load for each antibody.

Human and mouse tissue was processed as described previously (Wirths, O., et al. J Neural Transm 117, 85-96 (2010)). In brief, 4 μm paraffin sections were pretreated with 0.3% $H_2O_2$ in PBS to block endogenous peroxidases and antigen retrieval was achieved by boiling sections in 0.01 M citrate buffer pH 6.0, followed by 3 min incubation in 88% formic acid. Primary antibodies were incubated overnight, followed by incubation with biotinylated secondary antibodies (DAKO) before staining was visualized using the ABC method with Vectastain kit (Vector Laboratories) and diaminobenzidine as chromogen.

Figure 14:
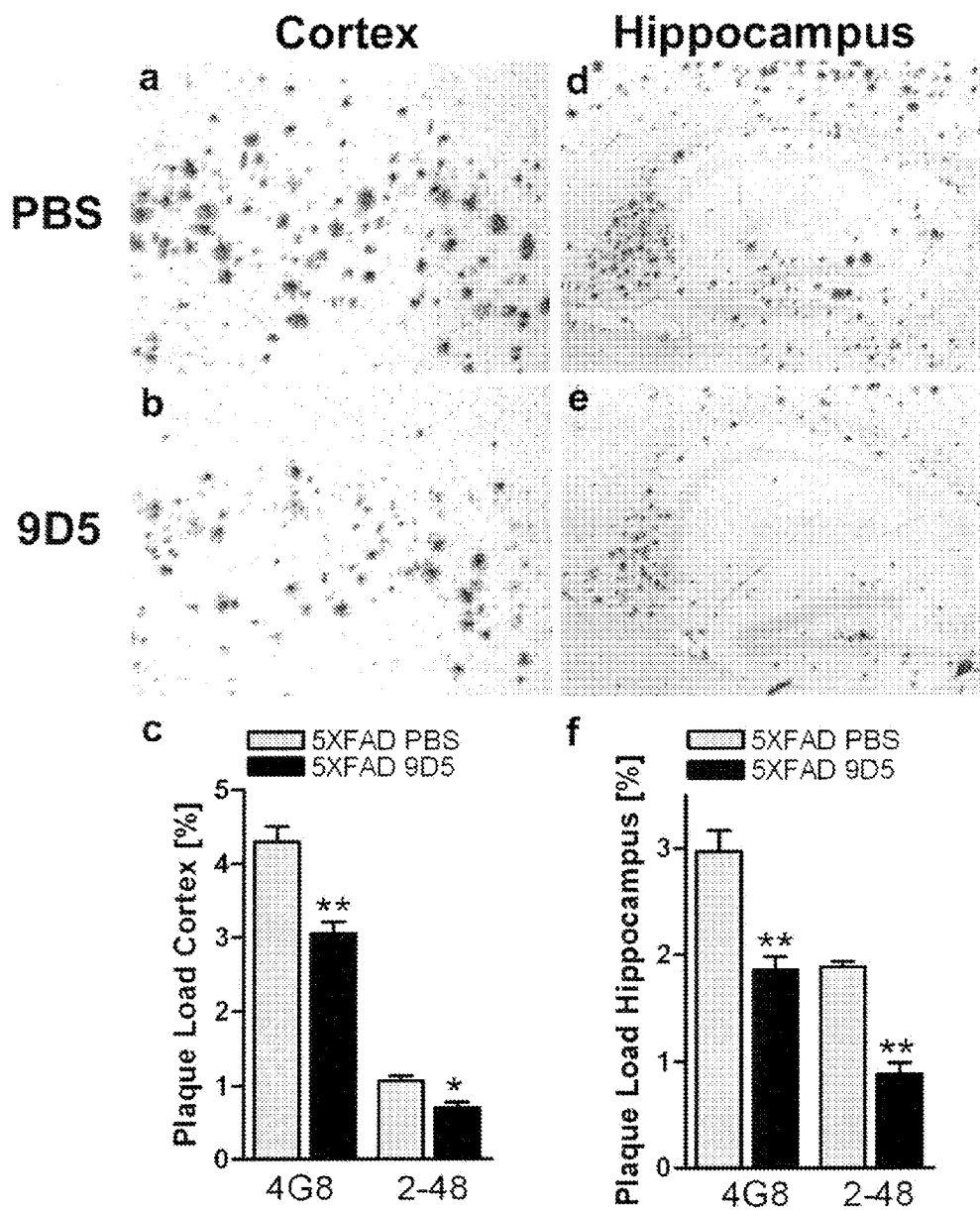
FIG. 14: Plaque-load quantification showed a significant decrease for both total Aβ (4G8) and pyroglutamate-modified Aβ (2-48) in 9D5-injected mice compared to PBS-injected mice in both cortex (a-c) and hippocampus (d-f). Representative images of 4G8-stained sections of PBS-injected (a, d) and 9D5-injected (b, e) 6-month-old 5XFAD mice are shown. *P<0.05; **P<0.01.
Figure 15:
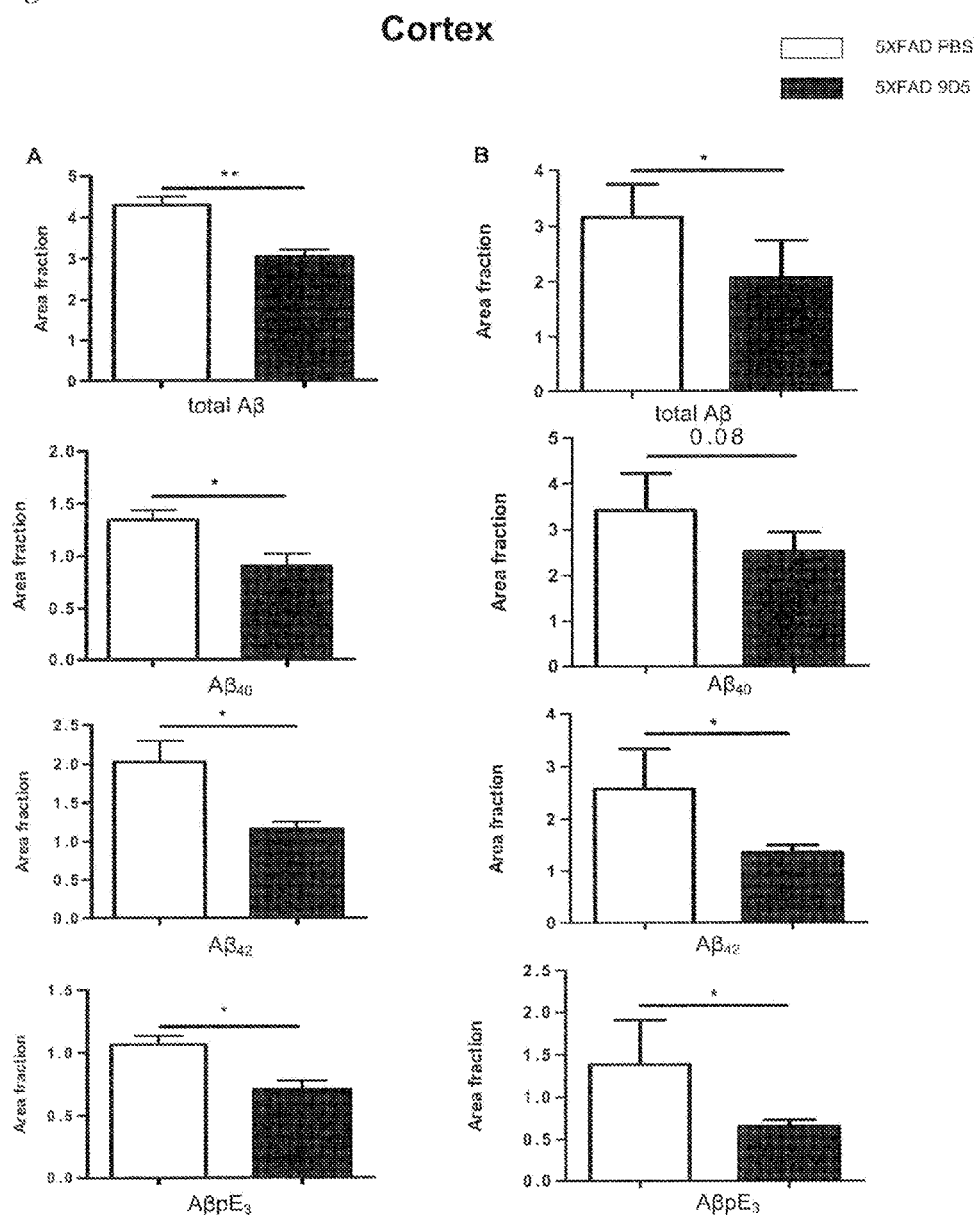
FIG. 15: a Cortex Therapeutic effect of 9D5 passive immunization in 5XFAD mice (cortex). Sections were stained against total Aβ (4G8), $Aβ_{X-40}$ (G210), $Aβ_{X-42}$ (G211), AβpE3 (2-48) (see also FIG. 14). A First cohort of immunized mice. Plaque-load quantification showed a significant decrease for total Aβ (4G8), pyroglutamate-modified Aβ (2-48), Aβ40 (G2-10), and Aβ42 (G2-11) in 9D5-injected mice compared to PBS-injected mice. B Second cohort of immunized mice. Immunization with 9D5 proved to reduce plaque load in the cortex of 6-month old 5XFAD mice when compared to age-matched controls. *P<0.05; **P<0.01.
Figure 15:
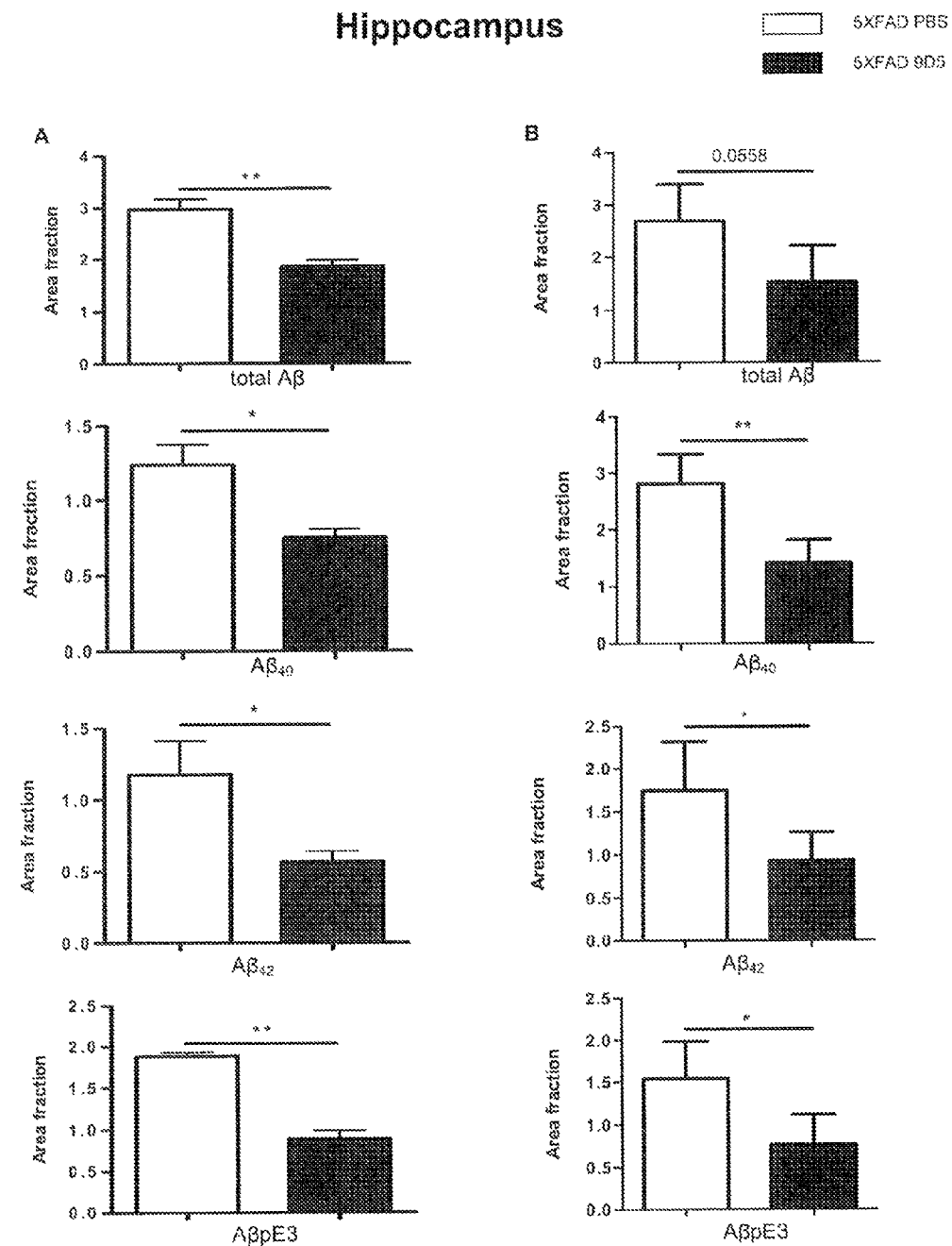

Plaque-load quantification showed a significant decrease for both total Aβ (4G8) and pyroglutamate-modified Aβ (2-48) in 9D5-injected mice compared to PBS-injected mice in both cortex (a-c) and hippocampus (d-f). Representative images of 4G8-stained sections of PBS-injected (a, d) and 9D5-injected (b, e) 6-month-old 5XFAD mice are shown in FIG. 14 and FIG. 15. *P<0.05; P<0.01. The data has been confirmed by tests using a second cohort of mice as shown in FIG. 15 Ab and FIG. 15** Bb.

Passive immunization of 5XFAD mice leads to reduction of Aβ peptides in plaques and rescue of behavioural deficits. Since 9D5 specifically recognizes only low molecular weight AβpE3 oligomers and not any Aβ1-42, the inventors hypothesize that AβpE3 oligomers are seeding other Aβ peptides that precipitate in plaques (and in Alzheimer brain in general). By reducing AβpE3 oligomer levels due to passive immunization with 9D5, plaque-associated Aβ peptides are also decreased correlating with rescue of behavioural deficits. The inventors believe that the above observation represents a novel therapeutic mechanism rescuing Alzheimer pathology and cognition. Without being bound to a specific theory, the inventors think that AβpE3 oligomers are central in the pathology and appear in the brain at a time point when behavioural deficits occur. Aβ1-42 precipitates in plaques earlier, but plaques are not toxic per se. Only when the oligomers are formed the toxic pathway is starting. Therefore, interrupting this toxic pathway by reducing specifically these oligomers also reduces other Aβ peptides. Oligomers are acting as pathological relevant seeds. It is very important that the therapy will primarily target oligomers and not other Aβ peptides as they mostly precipitate in plaques, which is a safe place and are not involved in toxicity. Once the toxic oligomers are reduced due to 9D5 therapy, as a second consequence plaque formation is also reduced. The secreted Aβ peptides in plaques however are no longer toxic.

9D5 Passive Immunisation Reduced Aβ40 and Aβ42 Plaque Load

Extracellular Aβ load using C-terminal specific anti-Aβ antibodies (G2-10 against Aβ40, G2-11 against Aβ42; The Genetics company Switzerland;) was evaluated in cortex and hippocampus using an Olympus BX-51 microscope equipped with an Olympus DP-50 camera and the ImageJ software (V1.41, NIH, USA). Serial images of 40× magnification (hippocampus) and 100× (cortex) were captured on six sections per animal which were 30 μm afar from each other. Using ImageJ the pictures were binarized to 16-bit black and white images and a fixed intensity threshold was applied defining the DAB staining.

9D5 treatment reduced Aβ40 and Aβ42 plaque load in cortex and hippocampus significantly (cf. FIG. 15). These data demonstrate that Aβ peptides ending at position 40 and 42 are affected by 9D5 treatment. ANOVA over all groups (P<0.0001). *P<0.05. The data has been confirmed by tests using a second cohort of mice as shown in FIG. 15 Ab and FIG. 15 Bb.

Example 16

AD-Like Pathology in Non-Human Primates

For many years now, non-human primates (NHP) have also been used as animal models to study Alzheimer's disease, demonstrating a different form of AD pathology than transgenic mice used in AD research. Since NHPs are not genetically modified, they rather represent sporadic AD-like pathology as opposed to transgenic mice which, due to their genetic mutations, mimic AD pathology.

Tissue from NHP such as from Common Marmoset (*Callithrix jacchus*), Tree Shrew (*Tupaia belangeri*) and Rhesus Macaque (*Macaca mulatta*) was kindly provided from the German Primate Centre (DPZ) in Göttingen, Germany. Tissue has been preserved in formalin before being embedded in paraffin the same way as murine tissue which is described above, and stained with the following antibodies: NT78 (generic Aβ), 2-48 (AβpE3), pyroGlu (AβpE3), 9D5 (oligomeric AβpE3-42), G210 ($Aβ_{X-40}$), G211 ($Aβ_{X-42}$), Aβ[N] ($Aβ_{1-X}$), AT8 (hyperphosphorylated Tau).

Samples from three male Tree shrews aged 7.5-9 years did not reveal any of the aforementioned proteins. Samples from three 2 female and 5 male Rhesus Macaque aged 7-10 years and 3-7 years, respectively, also did not show any AD-like pathology when stained with the aforementioned antibodies. Also, tissue samples from 3 female and 10 out of 11 male Common Marmosets aged 2-12.5 years and 3-12 years, respectively, were free of AD-like pathology. The only specimen to show AD-like pathology was the oldest Marmoset (M5, 23 years old). It showed scattered AD-like pathology like extracellular Aβ-plaque, CAA and even some intracellular Aβ-staining localized mainly in the cortex. Total Aβ, as detected by antibody NT78, could be identified in sporadic dense plaques. However, no blood vessels were stained positive for total Aβ. $Aβ_{40}$ could be detected within dense plaques as well as within vessel walls. $Aβ_{42}$ was found in diffuse extracellular depositions, yet not within vessel walls. $Aβ_{1-X}$ could be detected within dense plaques as well as within vessel walls. Distinct plaques consisting of N-terminally truncated Aβ with pyroglutamate at position 3 were distributed numerously all over the cortex and the same Aβ species was also found within vessel walls. Oligomeric $AβpE3_{3-42}$, as detected with antibody 9D5, was also detected sporadically and appears to lie intracellular as well as within vessel walls. Thioflavin S staining which detects aggregated β-sheet structures confirmed the presence of Aβ being accumulated within vessel walls. Staining for phosphorylated tau protein, as detected by antibody AT8, was also carried out yet did not reveal any signal for this epitope.

Apart from brain tissue, several different organs were tested for cross-reactivity with the 9D5 antibody. Since 9D5 is applied as both a diagnostic and therapeutic tool, cross-reactivity with organs other than the brain has to be ruled out to make sure those organs remain unharmed. The tissue samples that have been tested included heart, liver, spleen, colon, jejunum, caecum, kidney, adrenal, testicle, muscle. However, none of the organs revealed a specific staining when treated with 9D5.

In the present study, paraffin-embedded tissue from Common Marmoset, Rhesus Macaque and Tree Shrew were examined with regard to Aβ deposition using antibodies staining for generic (NT78), AβpE3 (2-48 and pyroGlu), oligomeric AβpE3-42 (9D5), $Aβ_{X-40}$ (G210), $Aβ_{X-42}$ (G211), $Aβ_{1-X}$(Aβ[N]), and hyperphosphorylated Tau (AT8). None of the tissue from the three Rhesus Macaques showed any staining with the abovementioned antibodies. Since it was previously shown that naturally occurring Aβ deposits could not be detected in 5-year old animals but only in 25-30 year old ones, the Rhesus Macaques used for the present study might have simply been too young (3-10 years) to show any Aβ deposition. The tissue of the three Tree Shrews used in the present study (7.5-9 years) did not show any signal with the antibodies applied. Although it was previously shown that Aβ immunoreactivity was shown to be present in 6.5-7.5 year old Tree Shrews, this study confirms previous findings that due to relative scarcity of Aβ-immunoreative structures it might be difficult to detect Aβ staining. Out of 14 specimens of Common Marmoset used in the present study, only tissue from one animal was found to be positive for almost all antibodies that had been applied except for AT8 (hyperphosphorylated Tau). AD-like pathology could only be detected in M5, a 23-year old male Marmoset. All other animals, aged 2-12 years, are considered to be too young for Aβ deposition to be detected. M5 showed a similar distribution of specific Aβ species as reported in previous studies with $Aβ_{40}$ detecting CAA and $Aβ_{42}$ being mainly found in plaques. Interestingly, this study is the first one to show the existence of oligomeric $AβpE_{3-42}$ in non-human primates. Pyroglutamate Aβ oligomers were shown to be the most abundant form in sporadic AD in humans. Therefore, the Common Marmoset appears to be a model for the analysis of sporadic AD.

Example 17

Microglia Cell in Alzheimer Brain Visualized with 9D5 Immunostaining

Sections of the gyrus temporalis superior from 99 AD patients were stained with an antibody specific for pyroglutamate Aβ oligomers (9D5 antibody). Data was available for each patient on diagnosis, gender, age, Braak stage, ApoE genotype and plaque deposition in the brain. The cohort used in this study consisted of samples of 76 females and 23 males with a mean age of 77.08±12.23 years. Braak stages ranged from 4 to 6 with a mean of 5.1. 57 of the patients were carriers for the ApoE4 allele whereas 46 patients had one ApoE4 allele and 11 patients harbored two copies of the ApoE4 allele.

The majority of the samples showed a robust plaque load deposition with generic Aβ antibody NT244. Only 9 patients had a minor plaque deposition in the brain. The staining intensity and pattern of the 9D5 antibody was analyzed for each of the 99 samples. 13 of 99 patients demonstrated a high abundance of cerebral amyloid angiopathy (CAA) staining with the 9D5 antibody. In addition 57 of 99 of the samples also showed 9D5 positive immunoreactivity in microglia cells. Statistical analysis revealed no correlation of 9D5-positive cerebral amyloid angiopathy staining with gender, age, Braak stage, ApoE genotype and plaque deposition. Furthermore there was also no correlation of the 9D5-positive microglia staining with any of these parameters. Interestingly, there was a correlation of 9D5 positive microglia with 9D5 CAA staining (Chi-Quadrat-Test p=0.034). Out of the 13 cases positive for 9D5 CAA, 10 samples showed microglial immunoreactivity in addition (cf. FIG. 16).

This observation is well in line with abundant 9D5-positive microglia staining in Alzheimer mouse models 5XFAD and APP/PS1KI indicating that low molecular weight AβpE3 oligomers can in principle be phagocytosed by microglia in mouse and man. Immunotherapy with 9D5 is likely helping microglial-dependent clearance of AβpE3 oligomers, which are seeding species for Aβ aggregation.

Example 18

Passive Immunization with N-Terminal Specific Monoclonal Antibody 2-48

Male 5XFAD mice were treated with 10 mg/kg 2-48 antibody for 4 months (3 to 7 months of age treatment period) by a weekly intraperitoneal injection.

Tissue was processed as described above. In brief, 4 μm paraffin sections were pretreated with 0.3% H2O2 in PBS to block endogenous peroxidases and antigen retrieval was achieved by boiling sections in 0.01 M citrate buffer pH 6.0, followed by 3 min incubation in 88% formic acid. Primary antibodies were incubated overnight, followed by incubation with biotinylated secondary antibodies (DAKO) before staining was visualized using the ABC method with Vectastain kit (Vector Laboratories) and diaminobenzidine as chromogen.

IBA1, a marker for microglia cells (IBA1 (rabbit) antisera from Wako Pure Chemicals), NT78 (against generic Aβ1-16, Synaptic Systems and University Medicine Goettingen) and 2-48 (against N-terminal AβpE3, Synaptic Systems and University Medicine Goettingen) were used.

Extracellular Aβ load was evaluated in cortex using an Olympus BX-51 microscope equipped with an Olympus DP-50 camera and the ImageJ software (V1.41, NIH, USA). Serial images of 40× magnification (hippocampus) and 100× (cortex) were captured on six sections per animal which were 30 µm afar from each other. Using ImageJ the pictures were binarized to 16-bit black and white images and a fixed intensity threshold was applied defining the DAB staining.

Passive immunization with a weekly injection of 2-48 antibody revealed a trend in plaque load reduction (cf. FIG. 17). Both, staining with the generic Aβ antibody NT78 and AβpE3-specific antibody 2-48 showed a trend in reduced plaque load in cortex of immunized mice. The 2-48 treatment effect was clearly smaller as the 6-week long treatment with 9D5. Nevertheless, as AβpE3 peptides are the precursor of the AβpE3-derived low molecular oligomers (as detected by 9D5), the results are interesting. They demonstrate that reducing the monomeric AβpE3 has some effects in reducing generic Aβ and AβpE3 plaques.

LIST OF REFERENCES

US 2009/0258009 A1
U.S. Pat. No. 4,816,567
U.S. Pat. No. 5,525,711
U.S. Pat. No. 4,711,955
U.S. Pat. No. 5,792,608
EP 302175
Aoki M, et al. (2008) *Neuroreport* 19(11):1085-1089.
Billman-Jacobe (Current Opinion in Biotechnology 7 (1996), 500-4).
Bitter et al. (Methods in Enzymology 153 (1987), 516-544.
Boche et al. (2010), Acta Neuropathol 120: 369-384.
Bosman F T. Histochem J. 1983 March; 15(3):189-200.
Breyhan (2009) Acta Neuropathol 117: 677-685.
Burnette, W. N. (1981), Anal. Biochem. 112: 195-203.
Busciglio J, et al. (2002) *Neuron* 33(5):677688).
Butler (1986) Mol Immunol. 23:971-982.
Casas (2004) Am J Pathol 165: 1289-1300.
Christensen (2008) Acta Neuropathol 116: 647-655.
Christensen (2008) Neurobiol Aging 31: 1153-1163.
Coloma et al. (1992) J. Imm. Methods 152: 89-104.
D'Andrea M R, et al. (2001) *Histopathology* 38(2):120-134.
D'Andrea M R, et al. (2002) *Neurosci Lett* 323(1):45-49.
Engvall, E. & Perlman, P. (1971), Immunochemistry. 8, 871-874.
Fernandez-Vizarra P, et al. (2004) *Histol Histopathol* 19(3):823-844.
Gersten and Marchalonis (1978) J. Immunol. Methods 24:305-309.
Goldsby, R. A., Kindt, T. J., Osborne, B. A. & Kuby, J. Enzyme-Linked Immunosorbent Assay. In: Immunology, 5th ed., pp. 148-150. W. H. Freeman, New York, 2003. Griffiths et al., (Methods in Molecular Biology 75 (1997), 427-440).
Gurtu et al. (1996) Biochem. Biophys. Res. Comm. 229: 295-298.
Gyure K A, et al. (2001) *Arch Pathol Lab Med* 125(4):489-492.
Harmeier (2009) J Neurosci 29: 7582-7590.
Hashimoto M, et al. (2010) *Acta Neuropathol* 119(5):543-554.
He (1999) Biochem 38: 10871-10877.
Hockney (Trends in Biotechnology 12 (1994), 456-463).
Holcomb (1999) Behav Genet 29: 177-185.
Jawahr et al., Neurobiol Aging (2010): doi:10.1016/j.neurobiolaging.2010.05.027.
Karl et al., (2003) Exp Toxicol Pathol 55, 69-83.
Kessler (1975) J. Immunol. 115:1617-1623.
Klein (2002) Neurochem Int 41: 345-352.
Kohler, G. et al., Nature 256 (1975) 495.
Lambert, M. P., et al. *Proc Natl Acad Sci USA* 95, 6448-6453. (1998).
Lesne, S., et al. *Nature.* 440, 352-357. (2006).
Lord, A., et al. *Febs J* 276, 995-1006 (2009).
Lord, A., et al. *Neurobiol Aging* 27, 67-77 (2006).
Matutes and Catovsky (1982) Clin. Exp. Immunol. 50:416-425.
McLean, C. A., et al. *Ann Neurol* 46, 860-866 (1999).
Methods in Yeast Genetics, A Laboratory Course Manual, Cold Spring Harbor Laboratory Press, 1990.
Mochizuki A et al. (2000) *Lancet* 355(9197):42-43.
Mori (1992) J Biol Chem 267: 17082-17086.
Mori C, et al. (2002) *Amyloid* 9(2):88-102.
Naslund, J., et al. *Jama* 283, 1571-1577. (2000).
Nebe-von-Caron G., et al. Journal of Microbiolgical Methods. 2000: 42:97-114.
Ono, K., et al. *Proc Natl Acad Sci USA* 106, 14745-14750 (2009).
Ormerod (2000) Flow Cytometry: A Practical Approach, 3rd edition.
Renart, J. et al. (1979), Proc. Natl. Acad. Sci. U.S.A. 76:3116-3120.
Rohrer, D. C., et al. *Cell Transplant* 5, 57-68 (1996).
Saido (1995) Neuron 14: 457-466.
Sambrook and Russell (2001), Molecular Cloning: A Laboratory Manual, CSH Press, Cold Spring Harbor, N.Y., USA.
Sawers et al. (Applied Microbiology and Biotechnology 46 (1996), 1-9.
Schägger and Jagow (1991) Anal. Biochem 199: 223-231.
Schilling (2008), Nat. Med 14:1106-1111.
Selkoe (2001) Physiol Rev 81: 741-766.
Spector and Goldmann (1998) Cells: A laboratory manual, vol. 2: Light microscopy and cell structure.
Sung et al., Methods in Enzymology 153 (1987), 385-516.
Takahashi, R. H., et al. J. Neurosci. 24, 3592-3599. (2004).
Tanaka H. et al. (2007), J Agric Food Chem.; 55(10):3783-7.
Tomiyama, T., et al. *J. Neurosci.* 30, 4845-4856 (2010).
Towbin et al. (1979) Proc. Nat. Acad. Sci. 76: 4350-4354.
Walsh, D. M., et al. *Biochemistry* 39, 10831-10839. (2000).
Walsh, D. M., et al. *Nature* 416, 535-539. (2002).
Wirths (2007) Neurobiol Aging 28: 1689-1699.
Wirths (2008) Neurbiol Aging 29: 891-901.
Wirths (2009) Acta Neuropathol 118: 487-496.
Wirths, O., et al. *J Neural Transm* 117, 85-96 (2010).

The invention claimed is:

1. An antibody molecule wherein said antibody molecule is an antibody obtainable by hybridoma as deposited under DSM ACC3056 or hybridoma as deposited under DSM ACC3066 on May 27, 2010 with the DSMZ GmbH, Braunschweig, Germany.

2. The antibody molecule according to claim 1, wherein said antibody molecule is capable of staining blood vessels, or cells, or both in a tissue sample.

3. The antibody molecule according to claim 1, wherein said antibody recognizes a conformational epitope or a discontinuous epitope formed by Aβ oligomers.

4. A hybridoma which produces the monoclonal antibody according to claim 1, wherein the hybridoma is hybridoma DSM ACC3056 or hybridoma DSM ACC3066 deposited on May 27, 2010 with the DSMZ GmbH, Braunschweig, Germany.

5. An isolated antibody molecule, wherein said antibody molecule comprises:
   (a) a variable region that comprises a H-CDR1, a H-CDR2 and a H-CDR3 as encoded by the nucleic acid sequence as shown in SEQ ID NOs: 1, 3 and 5; and a variable region that comprises a L-CDR1, a L-CDR2 and a L-CDR3 as encoded by the nucleic acid sequence as shown in SEQ ID NOs: 7, 9 and 11; or
   (b) a variable region that comprises a H-CDR1, a H-CDR2 and a H-CDR3 as encoded by the nucleic acid sequence as shown in SEQ ID NOs: 13, 15 and 17; and a variable region that comprises a L-CDR1, a L-CDR2 and a L-CDR3 as encoded by the nucleic acid sequence as shown in SEQ ID NOs: 19, 21 and 23; or
   (c) a heavy chain variable region comprising the three CDRs of SEQ ID NOs: 2, 4 and 6, and a light chain variable region comprising the three CDRs of SEQ ID NOs: 8, 10, and 12; or
   (d) a heavy chain variable region comprising the three CDRs of SEQ ID NOs: 14, 16 and 18, and a light chain variable region comprising the three CDRs of SEQ ID NOs: 20, 22, and 24,
   wherein the antibody molecule is a F(ab)-fragment, a F(ab)₂-fragment a F(v)-fragment, a single-chain antibody, a chimeric antibody, a CDR-grafted antibody, a bivalent antibody-construct, a humanized antibody, or a diabody.

6. The antibody molecule of claim 5 (a) or (c), wherein said antibody molecule comprises:
   (a) variable regions as encoded by a nucleic acid molecule comprising the nucleic acid molecules of SEQ ID NOs: 25 and 27; or
   (b) variable regions comprising the amino acid sequence of SEQ ID NOs: 26 and 28.

7. The antibody molecule of claim 5 (b) or (d), wherein said antibody molecule comprises:
   (a) variable regions as encoded by a nucleic acid molecule comprising the nucleic acid molecules of SEQ ID NOs: 29 and 31; or
   (b) variable regions comprising the amino acid sequence of SEQ ID NOs: 30 and 32.

8. The antibody molecule according to claim 5, wherein said antibody molecule is capable of staining blood vessels, or cells, or both in a tissue sample.

9. The antibody molecule according to claim 5, wherein said antibody recognizes a conformational epitope or a discontinuous epitope formed by Aβ oligomers.

10. A pharmaceutical composition comprising an antibody molecule as defined in claim 1 or claim 5, and a pharmaceutically acceptable carrier, excipient, diluent, or a combination thereof.

11. A diagnostic composition comprising an antibody molecule according to claim 1 or claim 5.

12. A kit comprising an item selected from an antibody molecule according to claim 1 or claim 5, a pharmaceutical composition thereof, and combinations thereof.

13. A method of treating an amyloid-related disorder, the method comprising administering a binding molecule to a subject suffering or prone to suffer from said amyloid-related disorder, wherein said binding molecule is an antibody molecule obtainable by the hybridoma deposited with the DSMZ under accession number DSM ACC3056 (antibody 9D5H6) or the hybridoma deposited with the DSMZ under accession number DSM ACC3066 (antibody 8C4D2).

14. The method of claim 13, wherein the binding molecule is capable of inhibiting Aβ-oligomerization as determined in a thioflavin T aggregation assay.

15. The method of claim 13, wherein said binding molecule inhibits the seeding effect of AβpE3 oligomers.

16. The method of claim 13, wherein said binding molecule recognizes a conformational epitope formed by at least two Aβ-pE3 peptides forming said soluble AβpE3 oligomers.

17. The method of claim 13, wherein the amyloid-related disorder is selected from Alzheimer disease, cerebral amyloid angiopathy, dementia, motor neuropathy, Down's syndrome, Creutzfeld Jacob disease, transmissible spongiform encephalopathies, hereditary cerebral hemorrhage with amyloidosis Dutch type, Parkinson's disease, HIV-related dementia, fronto-temporal dementia, Lewy body disease, mixed dementias, head trauma, familial Danish Dementia, familial British Dementia, inclusion body myositis (IBM), or neuronal disorder related to aging.

18. The method of claim 13, wherein the Alzheimer disease is sporadic Alzheimer disease.

19. The method of claim 13, wherein the Alzheimer disease is familial Alzheimer disease.

20. The method of claim 13, wherein the transmissible spongiform encephalopathies is selected from Gerstmann-Straussler-Scheinker syndrome, fatal familial insomnia and kuru.

21. The method of claim 13, wherein the binding molecule is an antibody molecule, selected from a monoclonal antibody, a recombinant full antibody (immunoglobulin), a F(ab)-fragment, a F(ab)$_2$-fragment, a F(v)-fragment, a single-chain antibody, a chimeric antibody, a CDR-grafted antibody, a bivalent antibody-construct, a synthetic antibody, a cross-cloned antibody, a humanized antibody, and a diabody.

22. The method of claim 13, wherein the binding molecule is in the form of a pharmaceutical composition, further comprising a pharmaceutically acceptable carrier, excipient, diluent, or a combination thereof.

23. The method of claim 22, wherein the composition is administered to said subject at a dose of 1 ng/kg body weight to 100 mg/kg body weight of said subject.

24. The method of claim 22, wherein the composition is administered via injection.

25. The method of claim 22, wherein the composition is administered directly into cerebral fluid or selected brain regions.

26. A method of inhibiting the formation or the seeding effect of oligomers of AβpE3 associated with an amyloid-related disorder in a subject, who has or is prone to form said oligomers, comprising administering a binding molecule to said subject, wherein said binding molecule is an antibody molecule obtainable by the hybridoma deposited with the DSMZ under accession number DSM ACC3056 (antibody 9D5H6) or the hybridoma deposited with the DSMZ under accession number DSM ACC3066 (antibody 8C4D2).

27. The method of claim 26, wherein said AβpE3 is AβpE (3-X), wherein X is selected from 42, 40, 38, 41, 39, and 37.

28. The method of claim 26, wherein the binding molecule is capable of inhibiting Aβ-oligomerization as determined in a thioflavin T aggregation assay.

29. The method of claim 26, wherein said binding molecule inhibits the seeding effect of AβpE3 oligomers.

30. The method of claim 26, wherein said binding molecule recognizes a conformational epitope formed by more than one Aβ-pE3 peptide forming said soluble AβpE3 oligomers.

31. The method of claim 26, wherein the amyloid-related disorder is selected from Alzheimer disease, cerebral amyloid angiopathy, dementia, motor neuropathy, Down's syndrome, Creutzfeld Jacob disease, transmissible spongiform encephalopathies, hereditary cerebral hemorrhage with amyloidosis Dutch type, Parkinson's disease, HIV-related dementia, fronto-temporal dementia, Lewy body disease, mixed dementias, head trauma, familial Danish Dementia, familial British Dementia, inclusion body myositis (IBM), or neuronal disorder related to aging.

32. The method of claim 26, wherein the Alzheimer disease is sporadic Alzheimer disease.

33. The method of claim 26, wherein the Alzheimer disease is familial Alzheimer disease.

34. The method of claim 26, wherein the transmissible spongiform encephalopathies is selected from Gerstmann-Straussler-Scheinker syndrome, fatal familial insomnia and kuru.

35. The method of claim 26, wherein the binding molecule is an antibody molecule, selected from a monoclonal antibody, a recombinant full antibody (immunoglobulin), a F(ab)-fragment, a F(ab)$_2$-fragment, a F(v)-fragment, a single-chain antibody, a chimeric antibody, a CDR-grafted antibody, a bivalent antibody-construct, a synthetic antibody, a cross-cloned antibody, a humanized antibody, and a diabody.

36. The method of claim 35, wherein the binding molecule is in the form of a pharmaceutical composition, further comprising a pharmaceutically acceptable carrier, excipient, diluent, or a combination thereof.

37. The method of claim 36, wherein the composition is administered to said subject at a dose of 1 ng/kg body weight to 100 mg/kg body weight of said subject.

38. The method of claim 36, wherein the composition is administered via injection.

39. The method of claim 36, wherein the composition is administered directly into cerebral fluid or selected brain regions.

* * * * *

SEQUENCE LISTING

```
<160> NUMBER OF SEQ ID NOS: 32

<210> SEQ ID NO 1
<211> LENGTH: 30
<212> TYPE: DNA
<213> ORGANISM: artificial sequence
<220> FEATURE:
<221> NAME/KEY: source
<223> OTHER INFORMATION: /note="Description of artificial sequence: 9D5
      heavy chain CDR1"

<400> SEQUENCE: 1
ggctacacat tcagtagcta ctggatagag                                           30

<210> SEQ ID NO 2
<211> LENGTH: 10
<212> TYPE: PRT
<213> ORGANISM: artificial sequence
<220> FEATURE:
<221> NAME/KEY: source
<223> OTHER INFORMATION: /note="Description of artificial sequence: 9D5
      heavy chain CDR1"

<400> SEQUENCE: 2

Gly Tyr Thr Phe Ser Ser Tyr Trp Ile Glu
1               5                   10

<210> SEQ ID NO 3
<211> LENGTH: 51
<212> TYPE: DNA
<213> ORGANISM: artificial sequence
<220> FEATURE:
<221> NAME/KEY: source
<223> OTHER INFORMATION: /note="Description of artificial sequence: 9D5
      heavy chain CDR2"

<400> SEQUENCE: 3
gagattttac ctggacgtgg tagtactcac tacaatgaga agttcaaggg c                   51

<210> SEQ ID NO 4
<211> LENGTH: 17
<212> TYPE: PRT
<213> ORGANISM: artificial sequence
<220> FEATURE:
<221> NAME/KEY: source
<223> OTHER INFORMATION: /note="Description of artificial sequence: 9D5
      heavy chain CDR2"

<400> SEQUENCE: 4

Glu Ile Leu Pro Gly Arg Gly Ser Thr His Tyr Asn Glu Lys Phe Lys
1               5                   10                  15

Gly

<210> SEQ ID NO 5
<211> LENGTH: 24
<212> TYPE: DNA
<213> ORGANISM: artificial sequence
<220> FEATURE:
<221> NAME/KEY: source
<223> OTHER INFORMATION: /note="Description of artificial sequence: 9D5
      heavy chain CDR3"

<400> SEQUENCE: 5
tcccctatta ctacctctga ctac                                                 24

<210> SEQ ID NO 6
<211> LENGTH: 8
```

```
<212> TYPE: PRT
<213> ORGANISM: artificial sequence
<220> FEATURE:
<221> NAME/KEY: source
<223> OTHER INFORMATION: /note="Description of artificial sequence: 9D5
      heavy chain CDR3"

<400> SEQUENCE: 6

Ser Pro Ile Thr Thr Ser Asp Tyr
1               5

<210> SEQ ID NO 7
<211> LENGTH: 48
<212> TYPE: DNA
<213> ORGANISM: artificial sequence
<220> FEATURE:
<221> NAME/KEY: source
<223> OTHER INFORMATION: /note="Description of artificial sequence: 9D5
      light chain CDR1"

<400> SEQUENCE: 7
agatctagtc agagccttct ccacagtaat ggaaacacct atttacat                48

<210> SEQ ID NO 8
<211> LENGTH: 16
<212> TYPE: PRT
<213> ORGANISM: artificial sequence
<220> FEATURE:
<221> NAME/KEY: source
<223> OTHER INFORMATION: /note="Description of artificial sequence: 9D5
      light chain CDR1"

<400> SEQUENCE: 8

Arg Ser Ser Gln Ser Leu Leu His Ser Asn Gly Asn Thr Tyr Leu His
1               5                   10                  15

<210> SEQ ID NO 9
<211> LENGTH: 21
<212> TYPE: DNA
<213> ORGANISM: artificial sequence
<220> FEATURE:
<221> NAME/KEY: source
<223> OTHER INFORMATION: /note="Description of artificial sequence: 9D5
      light chain CDR2"

<400> SEQUENCE: 9
aaagtttcca accgattttc t                                             21

<210> SEQ ID NO 10
<211> LENGTH: 7
<212> TYPE: PRT
<213> ORGANISM: artificial sequence
<220> FEATURE:
<221> NAME/KEY: source
<223> OTHER INFORMATION: /note="Description of artificial sequence: 9D5
      light chain CDR2"

<400> SEQUENCE: 10

Lys Val Ser Asn Arg Phe Ser
1               5

<210> SEQ ID NO 11
<211> LENGTH: 27
<212> TYPE: DNA
<213> ORGANISM: artificial sequence
<220> FEATURE:
<221> NAME/KEY: source
<223> OTHER INFORMATION: /note="Description of artificial sequence: 9D5
      light chain CDR3"
```

<400> SEQUENCE: 11
tctcaaagta cacatgttcc gctcacg    27

<210> SEQ ID NO 12
<211> LENGTH: 9
<212> TYPE: PRT
<213> ORGANISM: artificial sequence
<220> FEATURE:
<221> NAME/KEY: source
<223> OTHER INFORMATION: /note="Description of artificial sequence: 9D5
      light chain CDR3"

<400> SEQUENCE: 12

Ser Gln Ser Thr His Val Pro Leu Thr
1               5

<210> SEQ ID NO 13
<211> LENGTH: 30
<212> TYPE: DNA
<213> ORGANISM: artificial sequence
<220> FEATURE:
<221> NAME/KEY: source
<223> OTHER INFORMATION: /note="Description of artificial sequence: 8C4
      heavy chain CDR1"

<400> SEQUENCE: 13
gggtacacat tcagaagcta ttggatagag    30

<210> SEQ ID NO 14
<211> LENGTH: 10
<212> TYPE: PRT
<213> ORGANISM: artificial sequence
<220> FEATURE:
<221> NAME/KEY: source
<223> OTHER INFORMATION: /note="Description of artificial sequence: 8C4
      heavy chain CDR1"

<400> SEQUENCE: 14

Gly Tyr Thr Phe Arg Ser Tyr Trp Ile Glu
1               5                   10

<210> SEQ ID NO 15
<211> LENGTH: 51
<212> TYPE: DNA
<213> ORGANISM: artificial sequence
<220> FEATURE:
<221> NAME/KEY: source
<223> OTHER INFORMATION: /note="Description of artificial sequence: 8C4
      heavy chain CDR2"

<400> SEQUENCE: 15
gagattttac ctggaagagg tagtactaag tacaatgaga agttcaaggg c    51

<210> SEQ ID NO 16
<211> LENGTH: 17
<212> TYPE: PRT
<213> ORGANISM: artificial sequence
<220> FEATURE:
<221> NAME/KEY: source
<223> OTHER INFORMATION: /note="Description of artificial sequence: 8C4
      heavy chain CDR2"

<400> SEQUENCE: 16

Glu Ile Leu Pro Gly Arg Gly Ser Thr Lys Tyr Asn Glu Lys Phe Lys
1               5                   10                  15

Gly

<210> SEQ ID NO 17
<211> LENGTH: 24
<212> TYPE: DNA
<213> ORGANISM: artificial sequence
<220> FEATURE:
<221> NAME/KEY: source
<223> OTHER INFORMATION: /note="Description of artificial sequence: 8C4 heavy chain CDR3"

<400> SEQUENCE: 17
tcccctatta ctacctctga ctac                                           24

<210> SEQ ID NO 18
<211> LENGTH: 8
<212> TYPE: PRT
<213> ORGANISM: artificial sequence
<220> FEATURE:
<221> NAME/KEY: source
<223> OTHER INFORMATION: /note="Description of artificial sequence: 8C4 heavy chain CDR3"

<400> SEQUENCE: 18

Ser Pro Ile Thr Thr Ser Asp Tyr
1               5

<210> SEQ ID NO 19
<211> LENGTH: 48
<212> TYPE: DNA
<213> ORGANISM: artificial sequence
<220> FEATURE:
<221> NAME/KEY: source
<223> OTHER INFORMATION: /note="Description of artificial sequence: 8C4 light chain CDR1"

<400> SEQUENCE: 19
agatctagtc agagccttgt acacagtaat ggaaacacct atttacat                 48

<210> SEQ ID NO 20
<211> LENGTH: 16
<212> TYPE: PRT
<213> ORGANISM: artificial sequence
<220> FEATURE:
<221> NAME/KEY: source
<223> OTHER INFORMATION: /note="Description of artificial sequence: 8C4 light chain CDR1"

<400> SEQUENCE: 20

Arg Ser Ser Gln Ser Leu Val His Ser Asn Gly Asn Thr Tyr Leu His
1               5                   10                  15

<210> SEQ ID NO 21
<211> LENGTH: 21
<212> TYPE: DNA
<213> ORGANISM: artificial sequence
<220> FEATURE:
<221> NAME/KEY: source
<223> OTHER INFORMATION: /note="Description of artificial sequence: 8C4 light chain CDR2"

<400> SEQUENCE: 21
aaagtttcca accgattttc t                                              21

<210> SEQ ID NO 22
<211> LENGTH: 7
<212> TYPE: PRT
<213> ORGANISM: artificial sequence
<220> FEATURE:

<210> SEQ ID NO 22
<211> LENGTH: 6 (implied)
<212> TYPE: PRT
<213> ORGANISM: artificial sequence
<220> FEATURE:
<221> NAME/KEY: source
<223> OTHER INFORMATION: /note="Description of artificial sequence: 8C4 light chain CDR2"

<400> SEQUENCE: 22

Lys Val Ser Asn Arg Phe Ser
1               5

<210> SEQ ID NO 23
<211> LENGTH: 27
<212> TYPE: DNA
<213> ORGANISM: artificial sequence
<220> FEATURE:
<221> NAME/KEY: source
<223> OTHER INFORMATION: /note="Description of artificial sequence: 8C4 light chain CDR3"

<400> SEQUENCE: 23
tctcaaagta cacatgttcc gctcacg                                        27

<210> SEQ ID NO 24
<211> LENGTH: 9
<212> TYPE: PRT
<213> ORGANISM: artificial sequence
<220> FEATURE:
<221> NAME/KEY: source
<223> OTHER INFORMATION: /note="Description of artificial sequence: 8C4 light chain CDR3"

<400> SEQUENCE: 24

Ser Gln Ser Thr His Val Pro Leu Thr
1               5

<210> SEQ ID NO 25
<211> LENGTH: 345
<212> TYPE: DNA
<213> ORGANISM: artificial sequence
<220> FEATURE:
<221> NAME/KEY: source
<223> OTHER INFORMATION: /note="Description of artificial sequence: 9D5 VH"

<400> SEQUENCE: 25
cagctgcagc agtctggagc tgagctgatg aagcctgggg cctcagtgaa gatatcctgc      60
aaggctactg gctacacatt cagtagctac tggatagagt gggtaaagca gaggcctgga     120
catggccttg agtggattgg agagatttta cctggacgtg gtagtactca ctacaatgag     180
aagttcaagg gcaaggccac attcactgca gatacatcct ccaacacagc ctacatgcaa     240
ctcagcagcc tgacatctga ggactctgcc gtctattact gtgcaagatc ccctattact     300
acctctgact actggggcca aggcaccact ctcacagtct cctca                    345

<210> SEQ ID NO 26
<211> LENGTH: 115
<212> TYPE: PRT
<213> ORGANISM: artificial sequence
<220> FEATURE:
<221> NAME/KEY: source
<223> OTHER INFORMATION: /note="Description of artificial sequence: 9D5 VH"

<400> SEQUENCE: 26

Gln Leu Gln Gln Ser Gly Ala Glu Leu Met Lys Pro Gly Ala Ser Val
1               5                   10                  15

Lys Ile Ser Cys Lys Ala Thr Gly Tyr Thr Phe Ser Ser Tyr Trp Ile
            20                  25                  30

Glu Trp Val Lys Gln Arg Pro Gly His Gly Leu Glu Trp Ile Gly Glu
         35                  40                  45

Ile Leu Pro Gly Arg Gly Ser Thr His Tyr Asn Glu Lys Phe Lys Gly
     50                  55                  60

Lys Ala Thr Phe Thr Ala Asp Thr Ser Ser Asn Thr Ala Tyr Met Gln
 65                  70                  75                  80

Leu Ser Ser Leu Thr Ser Glu Asp Ser Ala Val Tyr Tyr Cys Ala Arg
                 85                  90                  95

Ser Pro Ile Thr Thr Ser Asp Tyr Trp Gly Gln Gly Thr Thr Leu Thr
            100                 105                 110

Val Ser Ser
       115

<210> SEQ ID NO 27
<211> LENGTH: 321
<212> TYPE: DNA
<213> ORGANISM: artificial sequence
<220> FEATURE:
<221> NAME/KEY: source
<223> OTHER INFORMATION: /note="Description of artificial sequence: 9D5
      VL"

<400> SEQUENCE: 27
gatgttgtga tgacccaaac tccactctcc ctgcctgtca gtcttggaga tcaagcctcc      60
atctcttgca gatctagtca gagccttctc cacagtaatg gaaacaccta tttacattgg     120
tacctgcaga agccaggcca gtctccaaag ctcctgatct acaaagtttc caaccgattt     180
tctggggtcc cagacaggtt cagtggcagt ggatcaggga cagatttcac actcaagatc     240
agcagagtgg aggctgagga tctgggagtt tatttctgct ctcaaagtac acatgttccg     300
ctcacgttcg gtgctgggac c                                               321

<210> SEQ ID NO 28
<211> LENGTH: 107
<212> TYPE: PRT
<213> ORGANISM: artificial sequence
<220> FEATURE:
<221> NAME/KEY: source
<223> OTHER INFORMATION: /note="Description of artificial sequence: 9D5
      VL"

<400> SEQUENCE: 28

Asp Val Val Met Thr Gln Thr Pro Leu Ser Leu Pro Val Ser Leu Gly
 1               5                  10                  15

Asp Gln Ala Ser Ile Ser Cys Arg Ser Ser Gln Ser Leu Leu His Ser
             20                  25                  30

Asn Gly Asn Thr Tyr Leu His Trp Tyr Leu Gln Lys Pro Gly Gln Ser
         35                  40                  45

Pro Lys Leu Leu Ile Tyr Lys Val Ser Asn Arg Phe Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Phe Cys Ser Gln Ser
                 85                  90                  95

Thr His Val Pro Leu Thr Phe Gly Ala Gly Thr
            100                 105

<210> SEQ ID NO 29
<211> LENGTH: 294

<212> TYPE: DNA
<213> ORGANISM: artificial sequence
<220> FEATURE:
<221> NAME/KEY: source
<223> OTHER INFORMATION: /note="Description of artificial sequence: 8C4 VH"

<400> SEQUENCE: 29

```
gctgagctga agaagcctgg ggcctcagtg aagatatcct gcaaggctac tgggtacaca      60
ttcagaagct attggataga gtgggtaaag cagaggcctg acatggcct tgagtggata      120
ggagagattt tacctggaag aggtagtact aagtacaatg agaagttcaa gggcaaggcc     180
acattcactg cagatacatc ctccaacaca gccaacatgc aactcagcag cctgacatct     240
gaggactctg ccgtctatta ctgtgcaaga tcccctatta ctacctctga ctac            294
```

<210> SEQ ID NO 30
<211> LENGTH: 98
<212> TYPE: PRT
<213> ORGANISM: artificial sequence
<220> FEATURE:
<221> NAME/KEY: source
<223> OTHER INFORMATION: /note="Description of artificial sequence: 8C4 VH"

<400> SEQUENCE: 30

```
Ala Glu Leu Lys Lys Pro Gly Ala Ser Val Lys Ile Ser Cys Lys Ala
1               5                   10                  15

Thr Gly Tyr Thr Phe Arg Ser Tyr Trp Ile Glu Trp Val Lys Gln Arg
            20                  25                  30

Pro Gly His Gly Leu Glu Trp Ile Gly Glu Ile Leu Pro Gly Arg Gly
        35                  40                  45

Ser Thr Lys Tyr Asn Glu Lys Phe Lys Gly Lys Ala Thr Phe Thr Ala
    50                  55                  60

Asp Thr Ser Ser Asn Thr Ala Asn Met Gln Leu Ser Ser Leu Thr Ser
65                  70                  75                  80

Glu Asp Ser Ala Val Tyr Tyr Cys Ala Arg Ser Pro Ile Thr Thr Ser
                85                  90                  95

Asp Tyr
```

<210> SEQ ID NO 31
<211> LENGTH: 258
<212> TYPE: DNA
<213> ORGANISM: artificial sequence
<220> FEATURE:
<221> NAME/KEY: source
<223> OTHER INFORMATION: /note="Description of artificial sequence: 8C4 VL"

<400> SEQUENCE: 31

```
tcttgcagat ctagtcagag ccttgtacac agtaatggaa acacctattt acattggtac     60
ctgcagaagc caggccagtc tccaaagctc ctgatctaca agtttccaa ccgattttct      120
ggggtcccag acaggttcag tggcagtgga tcaggacag atttcacact caagatcagc     180
agagtggagg ctgaggatct ggagttat ttctgctctc aaagtacaca tgttccgctc       240
acgttcggtg ctgggacc                                                    258
```

<210> SEQ ID NO 32
<211> LENGTH: 86
<212> TYPE: PRT
<213> ORGANISM: artificial sequence
<220> FEATURE:

```
<221> NAME/KEY: source
<223> OTHER INFORMATION: /note="Description of artificial sequence: 8C4
      VL"

<400> SEQUENCE: 32

Ser Cys Arg Ser Ser Gln Ser Leu Val His Ser Asn Gly Asn Thr Tyr
1               5                   10                  15

Leu His Trp Tyr Leu Gln Lys Pro Gly Gln Ser Pro Lys Leu Leu Ile
            20                  25                  30

Tyr Lys Val Ser Asn Arg Phe Ser Gly Val Pro Asp Arg Phe Ser Gly
            35                  40                  45

Ser Gly Ser Gly Thr Asp Phe Thr Leu Lys Ile Ser Arg Val Glu Ala
        50                  55                  60

Glu Asp Leu Gly Val Tyr Phe Cys Ser Gln Ser Thr His Val Pro Leu
65                  70                  75                  80

Thr Phe Gly Ala Gly Thr
                85
```